US009521966B2

(12) United States Patent
Schwartz

(10) Patent No.: US 9,521,966 B2
(45) Date of Patent: Dec. 20, 2016

(54) LOCALIZATION OF THE PARATHYROID

(71) Applicant: Alan N. Schwartz, Edmonds, WA (US)

(72) Inventor: Alan N. Schwartz, Edmonds, WA (US)

( * ) Notice: Subject to any disclaimer, the term of this patent is extended or adjusted under 35 U.S.C. 154(b) by 166 days.

(21) Appl. No.: 13/897,322

(22) Filed: May 17, 2013

(65) Prior Publication Data

US 2014/0288412 A1 Sep. 25, 2014

Related U.S. Application Data

(60) Provisional application No. 61/648,425, filed on May 17, 2012.

(51) Int. Cl.
| | | |
|---|---|---|
| *A61B 5/00* | (2006.01) | |
| *A61B 90/00* | (2016.01) | |
| *A61B 5/11* | (2006.01) | |
| *A61B 6/00* | (2006.01) | |
| *A61B 6/03* | (2006.01) | |

(52) U.S. Cl.
CPC ............ *A61B 5/1114* (2013.01); *A61B 5/1112* (2013.01); *A61B 5/415* (2013.01); *A61B 5/4227* (2013.01); *A61B 5/4887* (2013.01); *A61B 5/686* (2013.01); *A61B 5/6811* (2013.01); *A61B 34/20* (2016.02); *A61B 34/30* (2016.02); *A61B 90/361* (2016.02); *A61B 90/39* (2016.02); *A61B 6/037* (2013.01); *A61B 6/507* (2013.01); *A61B 2034/2048* (2016.02); *A61B 2090/3995* (2016.02)

(58) Field of Classification Search
CPC . A61B 19/5244; A61B 5/1114; A61B 5/6811; A61B 5/686; A61B 5/4227; A61B 5/1112; A61B 5/4887; A61B 5/415; A61B 90/39; A61B 90/361; A61B 2090/3995; A61B 34/30; A61B 34/20; A61B 2034/2048; A61B 6/037; A61B 6/507
See application file for complete search history.

(56) References Cited

U.S. PATENT DOCUMENTS

| | | | | |
|---|---|---|---|---|
| 5,377,678 A | * | 1/1995 | Dumoulin et al. | ........... 600/424 |
| 6,285,902 B1 | * | 9/2001 | Kienzle et al. | ............... 600/427 |

(Continued)

FOREIGN PATENT DOCUMENTS

| | | |
|---|---|---|
| DE | 10241071 | 1/2010 |
| JP | 4716119 | 7/2011 |

(Continued)

*Primary Examiner* — Long V Le
*Assistant Examiner* — Angela M Hoffa
(74) *Attorney, Agent, or Firm* — Patrick J. S. Inouye

(57) ABSTRACT

Systems and methods are disclosed for locating the parathyroid. In one aspect, temporal variation among a plurality of images is evaluated and at least one image is enhanced according to the temporal variation. The image may be enhanced to one or both of reduce conspicuity of the thyroid gland and enhance conspicuity of the parathyroid gland. Some of the plurality of images may be adjusted in order to align representations of a target portions. Adjustments may be based locations of one or more organs or one or more artificial markers affixed to a living body in the plurality of images. A local positioning system (LPS), GPS, or other locating system may be used to position a living body, align the plurality of images, or to guide the positioning of objects relative to the living body. An elastomeric gel marker for imaging applications is also disclosed.

27 Claims, 15 Drawing Sheets

(56) References Cited

U.S. PATENT DOCUMENTS

| | | | |
|---|---|---|---|
| 6,738,656 B1* | 5/2004 | Ferre et al. | 600/426 |
| 7,015,859 B2* | 3/2006 | Anderson | 342/450 |
| 8,880,149 B2* | 11/2014 | Barbot et al. | 600/424 |
| 2003/0060702 A1* | 3/2003 | Kuth et al. | 600/424 |
| 2004/0097806 A1* | 5/2004 | Hunter et al. | 600/434 |
| 2004/0171924 A1* | 9/2004 | Mire et al. | 600/407 |
| 2006/0184003 A1 | 8/2006 | Lewin et al. | |
| 2014/0163300 A1* | 6/2014 | Rigney et al. | 600/1 |
| 2015/0032233 A1* | 1/2015 | Cheng et al. | 700/90 |

FOREIGN PATENT DOCUMENTS

| | | |
|---|---|---|
| RU | 2342172 | 12/2008 |
| RU | 2381525 | 2/2010 |
| RU | 2410136 | 1/2011 |
| RU | 2434600 | 11/2011 |
| WO | 0218967 | 3/2002 |
| WO | 2011141829 | 11/2011 |

* cited by examiner

LOCALIZATION OF THE PARATHYROID

PRIORITY CLAIM

This application claims the benefit of U.S. Provisional Application No. 61/648,425 filed on May 17, 2012, the subject matter of which is incorporated herein by reference in its entirety.

FIELD OF THE INVENTION

This application relates to imaging of internal organs and, in particular, to parathyroid gland localization or localization of other organs.

BACKGROUND OF THE INVENTION

Most people have 4 parathyroid glands (some have fewer than 4 and some have more than 4 glands). These glands lie behind the Thyroid gland in the lower neck. They are separate from the thyroid gland. The parathyroid gland controls Calcium levels in the bones and blood. There are many symptoms and problems that can be caused by an over growth or over production of one or multiple Parathyroid gland(s). Some of the most common problems caused by parathyroid abnormalities include: osteoporosis (bone loss), kidney stones, changes in Mood, fatigue, and muscle problems.

An abnormal parathyroid gland can be imaged using radioactive Sestamibi. Technecium is a radioactive isotope that is bound to the Sestamibi. Sestamibi is a molecular compound that is taken up by abnormal parathyroid glands. Unfortunately, Sestamibi is also taken up by the Thyroid gland. The thyroid uptake impedes the visualization of the parathyroid glands because of the close proximity of the parathyroid gland to the thyroid.

The systems and methods disclosed herein provide an improved approach for visualizing the parathyroid and diagnosing parathyroid abnormalities.

SUMMARY OF THE INVENTION

In some embodiments, a method for identifying a bodily structure uses nuclear medicine image information acquired and compared over different time intervals in order to compare separate images using only one isotope. Some embodiments use identified target organs to align body structures and assess their three dimensional location based on acquired data based on a two dimensional projection with a modified or modulated or subtracted Nuclear medicine image. Specifically this technique can be useful and be applied to include but not restricted to Parathyroid gland detection imaging.

In most patients the thyroid activity diminishes over time. A normal parathyroid gland will take up Sestamibi early but the activity diminishes over time. The abnormal parathyroid gland will take up Sestamibi early and continue to accumulate Sestamibi over approximately 30 to 180 minutes, after which the Sestamibi activity will also diminish.

In an attempt to separate the thyroid activity from the parathyroid activity a technique was developed in the past where both radioactive iodine and Sestamibi Technecium are injected into the blood stream. Iodine is taken up by the thyroid and not the parathyroid. The Sestamibi is taken up by both. This technique is limited by the overlapping activities of the two isotopes and has the disadvantage of subjecting the patient to added radiation.

Post processing digital subtraction techniques have been previously utilized in medicine. One example is performing a CT scan (Computerized Tomogram) and a Sestamibi exam. The two images are superimposed and anatomy is combined with Sestamibi uptake to attempt to localize the abnormal parathyroid gland. The limitation of this approach is that it increases the radiation dose to the patient significantly and the radioactive localization is not improved by the CT scan.

Nuclear Medicine SPECT imaging utilizes only the initial sestamibi injection but is limited because the sestamibi Tc is usually viewed at only one point in time with computed tomography (CT) and if more views or temporal interrogations are performed using both CT and nuclear medicine (NM), then the patient is exposed to significant amounts increasing radiation.

A technique that can digitally subtract the Sestamibi radioactivity over a time period and distinguish thyroid from parathyroid activity would be beneficial in parathyroid imaging, especially if it can be performed with mathematical post-processing without subjecting the patient to added radioactivity.

For example, in some embodiments, a sestamibi scan is performed by placing the patient under a Nuclear Medicine camera that accumulates and records the activity emitted from the body. This can then be used to create a tomographic, 3-D or 2-D image of the body. A region of interest (ROI) or field of view (FOV) refers to the part of the body that is interrogated during the study.

In addition to the thyroid and the parathyroid, other organs of the body take up sestamibi. These include salivary glands, nasal mucosa, heart, liver, the spleen. Each of these organs may lie within a different site and plane of the body. Some embodiments use the different vital organs as reference points in the body. By using these reference points, the body can be aligned using either 3-D or 2-D modeling. External reference points can also be utilized.

A patient can be repositioned on a table or kept in the same location during the scan. In either situation, the reference points can then be used to realign the patient to a similar position or to adjust patient's images and detected activity with post processing. In some embodiments, the reference points are used to both align the patient and detected images and activity of the patient.

The activity can be viewed not only as an anatomic map but also as temporal maps. The temporal and the anatomic map can be used separately or together to detect activity that diminishes over time. The thyroid activity that diminishes over time can be subtracted and the parathyroid activity that increases over time can be enhanced. Similar activity or variable activity can be modeled appropriately to reflect patterns manifested by the parathyroid and thyroid.

In some embodiments, the anatomic map will be created by aligning in successive images one or more of the salivary glands, nasal mucosa, heart, liver, the spleen and the thyroid. External markers can also be placed anterior, posterior, and on the right and left sides or any combination of the above.

The anatomic map of activity will be examined over time and the differences in activity be subtracted, added, or otherwise enhanced, using, for example, linear or nonlinear mathematical methods of analysis and correction in combination with use of one or more of internal or external sensors and radioactive or non-radioactive devices. This technique differs from other mathematical correction processes in that other techniques utilize a target organ such as the heart or brain as the primary if not the sole source for image correction. In the techniques disclosed herein, a non-target image correction may be either predominantly or equally weighted with the target image. The target organ may be one of many radioactive sites that are used to correct for image alignment and accuracy. In addition to using radioactivity, some embodiments may use radioactive and non-radioactive sources such that image alignment and correction can include but are not restricted to external or internal sensors.

In some embodiments, the thyroid and the parathyroid activity can be distinguished and separated from each other using the methods disclosed herein. Activity will decrease in the thyroid and increase in the abnormal parathyroid gland for most patients over time. The thyroid activity can therefore be identified and subtracted out. The activity that remains will be the parathyroid activity. Methods of modeling the activity subtracted can include but are not restricted to simple subtraction, modulating the value given to subtracted regions based on geometric location or activity changes or a combination of the above.

For many patients, early imaging of the parathyroid is masked by higher radioactivity count rates in the thyroid. Over time, the thyroid activity theoretically decreases to a level low enough that the parathyroid activity will become greater than the thyroid activity. Although this event occurs in this manner in many patients, this phenomenon does not occur in a significant number of patients. In about 30 to 50% of patients the thyroid and the parathyroid activity can be overlapping or the thyroid radioactivity does not reduce sufficiently to yield a confident diagnosis for a parathyroid adenoma. In order to increase the confidence of the abnormal parathyroid diagnosis and improve the conspicuity between the thyroid activity and the parathyroid activity, imaging methods disclosed herein can be applied to overcome the limitations of persistent thyroid activity.

One method uses Tc-99 Sestamibi as the diagnostic isotope. A nuclear medicine camera device assigns regions of interest (ROT) or pixels to the body. This information is collected at different points in time (a temporal data set or temporal map). These data sets can be compared. A Region of Interest (ROI) is assigned a value and depending on the increase or decrease in that ROI the pixel can include but not restricted to be amplified, remain the same, diminished or modulated by a mathematical model in relationship to but not restricted to the present, future or the past images or the adjacent pixels or data sets.

One embodiment can include but is not restricted to an activity correction method where the thyroid exhibits an increase in activity after the first few seconds to minutes after administering a radioisotope. This increase in activity can then be used to identify a region that is designated as thyroid. Over time the normal thyroid activity will then diminish. One embodiment can include but is not restricted to a method where the removal of all activity in the thyroid neck region that is diminishing at a given threshold rate or at a given time interval or period is assumed to be thyroid activity. One embodiment can include but is not restricted to a method where all or most of the diminishing activity over time can then be added or subtracted from the image in a manner to include but not restricted to all or a portion of the activity in a manner to include but not restricted to the data being altered using a mathematical model that modulates the data by a method to include but not restricted to a linear or nonlinear or a variable or non-variable manner.

A mathematical model may be used that modulates the data by a method to include but not restricted to a linear or nonlinear or a variable or non-variable manner. In some embodiments, the abnormal parathyroid activity, which increases over time either in an absolute or relative manner relative to the thyroid activity can then be better imaged after deducing the thyroid activity. One embodiment can include but is not restricted to a method where all increasing absolute or relative activity can also be amplified after a specific target threshold time in conjunction with subtracting or reducing all diminishing activity, which is assumed in this model to be thyroid activity. In this embodiment the amplification of increasing activity the parathyroid will become more conspicuous compared to the decreasing thyroid activity, which will become less conspicuous. One embodiment can include but is not restricted to a method where the relative levels at which the values amplified or diminished can be adjusted or modulated upward or downward by filters that are absolute or relative and can have variable curves to include but are not restricted to nonlinear, linear, or Gaussian, exponential curve filters, or any combination of these or other filters. The resulting temporal data map may make the assumption that the increasing activity is presumably parathyroid, and the decreasing activity is thyroid. The amplified activity when viewed in relation to the background of relative decreasing activity, presumably thyroid, may advantageously yield greater conspicuity between the parathyroid and the parathyroid glands then the raw data images.

Computer-aided drafting (CAD) software can be utilized to assist in the defining or locating of the target organ by altering or enhancing/increasing or diminishing or attenuating the intensity of the representation of information or activity and this can be performed by the computer or by a living creature in a mechanical or an automated manner. In some embodiments an area to include but not restricted to a thyroid nodule or an area of the thyroid that is thicker or has more volume than other areas within the thyroid and this may appear more intense and be confused with parathyroid activity. The computer or living creature can alter the data or the representation of the data or image by altering or increasing or enhancing or decreasing or attenuating a given area of the data.

Some imaging methods may include receiving, by a computer system, a plurality of image frames representing received radiation from a region of interest within a living body at a series of time points. The images may be received subsequent to administering a radioisotope, such as Tc99 Sestamibi. A computer system evaluates temporal variation among the plurality of image frames. The computer system may generate an enhanced frame according to the evaluation of temporal variation by modifying an original frame of the plurality of image frames effective to enhance visibility of one or more target features of the one or more features in the enhanced frame. The computer system may store, display, or transmit for display to a display device, the enhanced frame for display.

Computer systems disclosed herein may include any computer system known in the art, such as a computer system having one or more processors operable to process executable and operational data and one or more memory devices operably coupled to the one or more processors. The one or more processors may store executable and operational data effective to cause the one or more processors to perform any or all of the methods described herein.

The computer system may modify the original frame effective to enhance visibility of one or more target features by adjusting in a first manner one or more first portions of the original frame having a first temporal variation pattern relative to a reference intensity; and adjusting in a second manner one or more second portions of the original frame having a second temporal variation pattern relative to the reference intensity. The one or more first portions may correspond to parathyroid glands of the living body and the one or more second portions may correspond to a thyroid gland of the living body.

The computer system may be configured to adjust the one or more first portions in the first manner and adjust the one or more second portions in the second manner by applying a temporal filter to the plurality of image frames. For example, the temporal filter may include one or more of a linear filter, non-linear filter, Gaussian filter, and exponential curve filter. Generating the enhanced frame according to the evaluation of temporal variation may include modifying the original frame according to application of a mathematical model to the plurality of image frames.

In some embodiments, the computer system is configured to generate the enhanced frame according to the evaluation of temporal variation by modifying the original frame according to temporal variation of a reference feature in the plurality of image frames. The reference feature may include a representation of radiation emitted by an artificial or non-organic structure affixed to the living body. In some embodiments, the artificial structure has a known decay rate and modifying the original frame according to temporal variation of the reference feature of the one or more features may include correcting measured activity for one or more portions of the original frame according to measured activity for the artificial structure and the known decay rate.

In some embodiments, the computer system is configured to identify a representation of a thyroid of the living body in the plurality of image frames by identifying in the plurality of image frames portions showing an initial increase in activity relative to reference activity apparent in the plurality of image frames followed by a decrease in activity meeting a condition with respect to the reference activity. The computer system may then be configure to generate the enhanced frame according to the evaluation of temporal variation by altering the representation of the thyroid in the enhanced frame.

In some embodiments, the computer system is configured to identify representations of a thyroid gland in the plurality of image frames according to temporal variation of the representations of the thyroid gland in the plurality of image frames generates the enhanced frame by adjusting a representation of the thyroid gland in the enhanced frame effective to enhance the conspicuity of the one or more representations of the one or more parathyroid glands. This may include reducing intensity of the representation of the thyroid gland or otherwise making the representation of the thyroid gland less visibly distinct in the enhanced image.

In some embodiments, the computer system may be configured to identify the one or more representations of the one or more parathyroid glands in the plurality of image frames according to temporal variation of the one or more representations of the one or more parathyroid glands in the plurality of image frames. The computer system may further be configured to generate the enhanced frame by adjusting the representations of the one or more parathyroid glands in the selected frame to enhance conspicuity of the representations of the one or more parathyroid glands. The computer system may identify the representation of the one or more parathyroid glands in the plurality of image frames by identifying increasing activity of the representations one or more parathyroid glands relative to the reference activity represented in the plurality of image frames.

In some embodiments, the computer system is configured to identify the one or more representations of the one or more parathyroid glands in the enhanced frame, identify a representation of the thyroid gland in the enhanced frame, and evaluate one or more locations of the one or more representations of the one or more parathyroid glands relative to the representation of the thyroid in the enhanced frame. The computer system may be configured to characterize health of the one or more parathyroid glands according to the evaluation of the locations of the one or more parathyroid glands. For example, evaluating the one or more locations of the one or more representations of the one or more parathyroid glands may include evaluating asymmetry of the one or more locations of the one or more representations of the one or more parathyroid glands relative to the thyroid; atypical positioning of the one or more locations of the one or more representations of the one or more parathyroid glands relative to the thyroid; and eccentric positioning of the one or more locations of the one or more representations of the one or more parathyroid glands relative to the thyroid.

An alternative imaging method may include administering a radioisotope to a living body. A computer system may be configured to receiver from a detector, such as any of the imaging systems discussed herein, an original image representing received radiation from a region of interest within the living body subsequent to administration of the radioisotope. A first treatment may be administered to the living body subsequent to administering the radioisotope, the first treatment effective to reduce activity in one or more parathyroid glands of the living body. The first treatment may be administered after detecting the original image. Alternatively, the first treatment may be administered prior to detecting the original image such that the effect of the first treatment is not apparent in the original image.

The computer system may be configured to receive from the detector, a confirmation frame, the confirmation frame representing received radiation from the region of interest within the living body subsequent to administering the first treatment. The computer system may then be configured to compare the confirmation frame to the original frame and identify as one or more representations of the one or more parathyroid glands those portions of the enhanced frame that have high apparent activity and for which corresponding portions in the confirmation frame have reduced apparent activity. In some embodiments, one or both of the original frame and confirmation frame may be enhanced according to some or all of the methods disclosed herein. The first treatment may include a treatment effective to reduce activity of the parathyroid, such as reducing uptake of the radioisotope. For example, the first treatment may include at least one of non-radioactively labeled sestamibi, calcium, a calcium channel blocker, and An agent that alters the sensitivity of the sensing receptors or the uptake activity in the parathyroid, such as cinacalcet (Sensipar™).

In some embodiments, an imaging method includes administering a first treatment to a living body, the first treatment operable to alter functioning of a first organ of the living body. One or more images may then be generated of at least a portion of the loving body using a first imaging modality. The one or more images may be enhanced and/or analyzed according to any of the methods disclosed herein. The first treatment may be effective to enhance conspicuity of a target portion of the living body due to the altering of the functioning of the first organ. The target portion may be a second organ of the living body different from the first organ or may be the first organ. For example, the first organ may be a parathyroid gland or a thyroid gland. The first treatment may be operable to affect, e.g. increase, blood flow to the first organ. The first treatment may additionally or alternatively be operable to affect uptake of a substance, e.g. Tc-99 Sestamibi, that enhances visibility of the first organ in the first imaging modality.

In some embodiments, the first treatment is at least one of hydrochlorothiazide, calcium, calcium channel blocker, An agent that alters the sensitivity of the sensing receptors or activity or uptake in the parathyroid (e.g. cinacalcet), and an inorganic phosphate and affects blood flow in the parathyroid. In other embodiments, the first treatment affects blood flow to the thyroid and is at least one of propylthiouracil, methimazole (Tapazole), thiourea, thiouracil, and a derivative of at least one of propylthiouracil, methimazole (Tapazole), thiourea, iodine, and thiouracil. In some embodiments, the first treatment affects uptake of a first substance by the thyroid. For example, the first treatment may be a thyroid agent including at least one of propylthiouracil, methimazole (Tapazole), thiourea, thiouracil, iodine, a thyroid 2 stimulating hormone (TSH), a thyroid 2 releasing hormone (TRH), a TSH blocking agent, a TRH blocking agent, or a derivative of the thyroid agent. In some embodiments, the first treatment is effective to affect calcium uptake by the first organ. In some embodiments, the first treatment includes one of adding and withdrawing energy from the organ.

A second feature of this embodiment can include but is not restricted to a localization method where the alignment of the thyroid and the parathyroid can be improved by registering body structures that take up and transmit the radioactivity, the Tc 99 Sestamibi, to include but not restricted to the salivary glands, the heart, the liver and active radioactive markers. These structures are distributed at different locations within the body and have a three-dimensional relationship in the body. These localizing structures can be chosen to include but are not restricted to body structures that do not significantly change their relative position in the body during the course of the scan. Even though the localizing structures activity may vary during the scan, the absolute or relative activity is not the issue and it is the location of the structure and of its activity that is most pertinent to aligning the body parts using a method to include but not restricted to two dimensional (2-D) or three dimensional (3-D) modeling or a combination of both 2-D and 3-D modeling. By aligning these localizing structures a patient can thus move around or even be removed from and then returned to the scanner and the image can still be aligned even if the patient moves between scans. One embodiment can include but is not restricted to a method where the data is realigned using a mathematical correction for positioning utilizing the expected 3-D location which is then transmuted into a 2-D location of the structures to compensate for misalignments between scans. In one embodiment the liver and spleen and salivary glands and heart can be used as internal markers of alignment, An external marker can be affixed to the body. A mathematical model can be used to assess the movement or the rotation of each of these organs or markers. Mathematical modeling can utilize but is not restricted to edge detection, step detection, edge thinning, using a Kirsch operator, pixel or voxel realignment which can include but is not restricted to measuring the number of pixels or voxels or both and comparing the increase or decrease in the number of pixels or voxels in any direction and correcting the movement to align or change in position to or with the original or propositus image. This process can be performed once or more than once to fine-tune or adjust the static target locations. This method can be combined with other methods that provide for image alignment or re-alignment, including but not restricted to Computed Tomography (CT), Ultrasound (US), Photo-Acoustic imaging (PAI), Magnetic Resonance Imaging (MRI), Thermography, or other imaging and/or positioning techniques.

One embodiment can include but is not restricted to a method where the alignment can be augmented using three-dimensional mathematical modeling of either the target organs, to include but not restricted to the thyroid and parathyroid or the non-target organs to include but not restricted to the salivary glands, the heart, and the liver or active nuclear radioactive markers.

Another embodiment can include but is not restricted to a method where the radioactivity of the non-target organs can be standardized and correctional computations performed based on an increase or decrease in radioactive activity over time and then compare this increase or decrease in activity to but mot restricted to the target organ (e.g. thyroid and parathyroid glands).

Another method can use but is not restricted to the use of external radioactive markers, which can be standardized and the rate of decay measured and used to correct for target and non-target organ corrections or location and activity.

Another method can use but is not restricted to the use of external radioactive markers, which can be used as localizing markers by which alignment can be augmented or achieved and can be combined with other alignment methods to include but not restricted to alignment of the target and non-target organ corrections or location and activity.

One embodiment can include but is not restricted to a method where the radioactivity is acquired in a continuous or discontinuous method or a combination of continuous or discontinuous.

One embodiment can include but is not restricted to a method where the activity correction method, the localization method or a combination of the activity correction method and the localization method and other currently utilized methods that can use and include but is not restricted to CT, MRI, US, PAI, Thermography or other imaging techniques.

One embodiment can include but is not restricted to a method where the localization is performed with electro-magnetic radiation to include but not restricted to near infra-red, infra-red, ultraviolet and thermographic imaging device. Thermography can be used to image parathyroid locations. In one embodiment the patient can be repositioned on the table in the same position by using a method that includes but is not restricted to thermography, heat or near infra-red, infra-red imaging or a combination of the above.

One embodiment can include but is not restricted to a method where the localization is performed with kinetic or ultrasound or mechanical or electro-magnetic energy alone or in combination to include but not restricted to near infra-red, infra-red, ultraviolet and thermographic imaging device, ultrasound, mechanical localization or fixation.

In one embodiment the patient can be repositioned on the table in the same position by using a method that includes but is not restricted to thermography, heat or near infra-red, infra-red imaging or a combination of the above.

In another embodiment the heat sensitive method for localization can be applied using a superimposed thermographic acquisition or image and the nuclear medicine radioactivity image can be corrected using a method to include but not restricted to mathematical correction, filter correction, position correction.

In another embodiment the electro-magnetic sensitive method for localization can be applied using but not restricted to a superimposed thermographic acquisition or image and the nuclear medicine radioactivity image can be corrected using a combination of methods to include but not restricted to mathematical correction, filter correction, position correction and the embodiment where the patient can be repositioned on the table in the same position by using a method that includes but is not restricted to thermography, heat or near infra-red, infra-red imaging or a combination of the above.

In another embodiment a heat sensitive method to include but not restricted to thermography or near infra-red, infra-red detection can be applied for localizing abnormal parathyroid glands. Heat sensitive methods are based on the fact that pathological parathyroid glands have a high blood flow rate and an increased metabolism that produces increased heat which can be detected by instruments that include but are not restricted to thermographic or near infra-red, infra-red sensitive detection devices. These thermographic or infra-red methods and detectors can be used alone or in combinations with other imaging detection or localizing devices to be used to include but not restricted to identify the location of an abnormal dysfunctioning parathyroid or thyroid gland, assist in registration and alignment of body structure, treatment of abnormal thyroid or parathyroid structures or any combination of these organs or techniques or methods.

In another embodiment a calcium detection method to include but not restricted to NMR, Functional magnetic resonance, or magnetic resonance imaging spectroscopy detection can be applied for localizing abnormal parathyroid glands. The calcium sensitive methods are based on the fact that pathological parathyroid glands have a high blood flow rate and an increased calcium detection or binding or metabolism that produces calcium localization which is absolute or relative to surrounding tissue which can be detected by instruments that include but are not restricted to 3-D or 2-D US, MRI, Nuclear Magnetic resonance (NMR), Functional magnetic resonance, or magnetic resonance imaging spectroscopy detection sensitive detection devices and Nuclear Medicine SPECT. These NMR, Functional magnetic resonance, or magnetic resonance imaging spectroscopy detection methods and detectors can be used alone or in combinations with other imaging detection or localizing devices to be used to include but not restricted to identify the location of an abnormal dysfunctioning parathyroid or thyroid gland, assist in registration and alignment of body structure, treatment of abnormal parathyroid or thyroid or structures or any combination of these organs or techniques or methods.

In some embodiments, an imaging method may be performed by a computer system and include receiving by a computer system, a plurality of image frames, the plurality of image frames representing received radiation from a region of interest within a living body at a series of time points. Representations of one or more organs and locations thereof are identified by the computer system in the plurality of image frames. A plurality of adjusted frames based on the image frames may be generated by the computer system, where the one or more of the adjusted frames have been transformed relative to corresponding image frames of the plurality of image frames according to the locations of the representations of the one or more organs in the corresponding image frames. In some embodiments, the adjusted frames may then be enhanced according to some or all of the image enhanced methods disclosed herein. The adjustment of the image frames may advantageously facilitate evaluation of temporal variation among frames by ensuring that the portion of the adjusted images corresponding to a target area are aligned with one another.

In some embodiments, the computer system is configured to generate the plurality of adjusted frames based on the plurality of image frames by identifying expected three-dimensional locations of the one or more organs based on the plurality of image frames and calculating two-dimensional locations for the one or more organs in the plurality of adjusted image frames based on the expected three-dimensional locations.

In some embodiments, the computer system is configured to generate the plurality of adjusted frames based on each frame of the plurality of image frames by identifying first locations of the representations of the one or more organs in the each frame and identifying second locations of the representations of the one or more organs in a frame other than the each frame in the plurality of image frames. The computer system may be configured to generate the adjusted frame of the plurality of adjusted frames corresponding to the each frame according to a transformation based on the first locations and the second locations.

The one or more organs may perform uptake of a radioisotope. For example, the received radiation from the region of interest may be in response to administration of Tc99m-sestamibi to the living body. The organs may also have relatively fixed locations within the living body. For example, the one or more organs may include one or more of the salivary glands, nasal mucosa, heart, liver, and spleen of the living body.

In another imaging method, a radioisotope is administered to a living body and one or more radioactive markers are affixed relative to the living body. A computer system receives a plurality of image frames, the plurality of image frames representing received radiation from the radioactive markers and from within the living body at a series of time points. The computer system is configured to identify one or more reference features and the locations thereof in the plurality of image frames, where the one or more reference features corresponding to the radioactive markers. The computer system may be further configured to generate a plurality of adjusted frames based on the image frames wherein one or more of the adjusted frames have been transformed relative to corresponding image frames of the plurality of image frames according to the locations of the one or more reference features in the corresponding image frames.

In some embodiments the computer system may be configured to generate the adjusted frames based on the locations in the image frames of both the reference features and representations of one or more organs as described above. The methods whereby the image frames are adjusted based on the locations of the reference features, or both the reference features and the one or more organs, may be as described above with respect to using the locations of organs to generate adjusted image frames. Likewise, the adjusted frames based on the reference features may be enhanced and/or analyzed according to any of the methods described herein.

The radioactive markers may be affixed to the surface of the living body, to a frame secured to the loving body, or implanted within the living body.

One embodiment can include but is not restricted to a method where the localization and positioning of the patient is performed with a Global Positioning Satellite Tracking Device (GPS). The GPS can be positioned onto the patient in one or more locations. In one embodiment the GPS device can be affixed directly to the body using various methods to include but not restricted to adhesive, tapes, elastic, cloth, can be injected or implanted and Velcro In another method the GPS device can be affixed indirectly to the body using a method to include but not restricted to a garment, a mask, a frame, a helmet, or an apparatus designed to mold to a body part. The direct and the indirect methods can be used alone or in combinations.

One embodiment the GPS device can be used but is not restricted assist in patient positioning. This method can be used to include but not restricted to assist radioactivity and thermography correction and localization methods by more precisely superimposing the body structures and providing for more accurate image correction. The GPS can be used for correction methods and for localization method or a combination of the correction method and localization method. The GPS method can be used with currently utilized methods for image creation and quantitative and qualitative methods that can include but not restricted to CT and PET or correct quantitation to include but not restricted to Gaussian, linear or exponential curve filters.

One embodiment can include but is not restricted to a method where the localization and positioning of the patient is performed with a system that shall be referred to as a Local Positioning Tracking Device (LPS). A mobile or fixed coordinate location device replaces the transmitters and receivers or satellite-substitute coordinate locators in a space that surrounds the object or patient or body being interrogated.

LPS is an imaging system that can be isolated from the outer environment and from radiofrequency signals. On method for isolating the LPS device can include a room lined with a material that prevents the influx of electromagnetic waves to include but not restricted to radiofrequency waves (RF). One method to isolate the room and the LPS system from the outer environment can include but is not restricted to lining the room with materials that can include but are not restricted to copper that behave as a barrier to the random influx of these wave and is referred to as a Faraday cage.

In some embodiments, a method for imaging may be performed by a computer system and include receiving a plurality of image frames, the plurality of image frames representing received nuclear radiation from a region of interest within a living body at a series of time points. The method may further include receiving, by the computer system, for each frame of at least a portion of the plurality of image frames, a secondary measurement of the living body corresponding to the each frame. The computer system may generate a plurality of adjusted frames based on the plurality of image frames by transforming at least a portion of the plurality of image frames according to the secondary measurements of the living body corresponding to the at least a portion of the plurality of image frames. The adjusted images may be enhanced and/or analyzed according to the methods described herein.

In some embodiments, the computer system may be configured to transform the at least a portion of the plurality of image frames according to the secondary measurements by, for each frame of the at least a portion of the plurality of image frames identifying one or more first reference measurements from the secondary measurement corresponding to the each frame; identifying one or more second reference measurements from the secondary measurement corresponding to a frame other than the each frame in the plurality of image frames; and generating the adjusted frame of the plurality of adjusted frames corresponding to the each frame based on the first and second reference measurements.

The secondary measurements may be received from GPS or LPS positioning receivers affixed to the living body or embedded therein. Secondary measurements may be received from a camera having the region of interest in a field of view thereof. The camera may detect light in the visual spectrum, infrared (e.g. thermographic), near-infrared, or some other spectrum. In some embodiments, the secondary measurements may include measurements of translucence of the loving body for one or more wavelengths or wavelength ranges. Secondary measurements may also be performed using a mechanical measuring means, magnetic resonance imaging, ultrasound, PAI, X-ray, computed tomography, positron emission tomography, single-photon emission computed tomography, or some other imaging modality.

The local LPS coordinate location works similar to ones used in a satellite position in that it is set by the position of the locator in space and the position and distance from each other is a known entity. Each locator has the capacity to send and/or receive and small be referred to as a locator. By knowing the position of each locator a coordinate system can be created relative to the space created by said locators. When an object is placed in the coordinate system the precise location of that object can be determined relative to that coordinate system by placing locators onto the target object or body or body part.

An LPS receiver calculates its position by precisely timing the signals sent by LPS devices strategically placed around the target which can include but is not restricted to the patient being imaged. Each LPS device continually transmits messages that include, the time the message was transmitted and the precise positional information of the LPS device that substitutes for the ephemeris in a GPS device. The LPS receiver or receivers which are positioned relative to the target that can include but is not restricted to the patient's body or a body part of the patient uses the signals it receives to determine the transit time of each signal and computes the distance from each LPS transmission device. These distances along with the LPS transmission devices locations are calculated using an algorithm to include but not restricted triangulation, trilateration, depending on which algorithm is used, to compute the position of the receiver. The position to include but not restricted to the body or body part is then displayed on a display that can include but is not restricted to a body profile, a schematic of the body, a moving map, a Cartesian map, a display with latitude and longitude and elevation, a display with cranial caudal and anterior-posterior position, The display can include but is not restricted to displaying animated information, an x-ray, CT, PET scan, Nuclear Medicine, Ultrasound, PAI, Thermographic or optical image or imaging system and that image can display information to include but not restricted to anatomic information, physiologic information, radioactivity, instrumentation information, human information to include but not restricted to receivers or transmitters on the hands, fingers, surgical tools and the information displayed can include but is not restricted to movement, speed, direction, and change in position.

In some embodiments four LPS transmission devices are optimal but the number of LPS transmission devices can be more than or fewer than four LPS transmission devices. Fewer than four LPS transmission devices can be used if the LPS receiver knows its position which can include but is not restricted to a fixed receiver on or in the body or body part that serves as an absolute or relative position in reference to the body.

One embodiment, can include but is not restricted to determining a location using a mathematical method such as lateralization using the LPD transmitters that can be on the body in the body, external to the body or any combination of on the body in the body, and external to the body.

In one embodiment a method is used for correcting for the speed of light which is a large value to include but not restricted to a method using an atomic clock that is as accurate as can be manufactured. In another method a solution for correcting for clock error can include but are not restricted to using additional antenna or transmitters whose spheres or signals intersect to include but are not restricted to a control signal or sphere or surface or computational or constructed fixed coordinate or coordinates.

In another embodiment, the receiver can be constructed to exceed standard bit speeds of 4,800 bit/sec and can use protocols that do not require large ranges but can focus on small areas. By not utilizing standard GPS this would provide a method that was in compliance with US Government controls. Also by placing the transmitters below the ionosphere one of the major causes of delay can be bypassed.

Another embodiment can include but is not restricted to one or multiple LPS devices. Another embodiment can include but is not restricted to one or multiple GPS devices. Another embodiment can include but is not restricted to a combination of one or multiple LPS and GPS devices.

Another embodiment can include a method for correcting for error if a GPS device is used. An error can occur secondary to delay in signal transmission through the ionosphere. More than one transmitting frequency can be used to correct for ionosphere error by comparing capture rates for each frequency.

Another embodiment can include but is not restricted to using a more precise method called Carrier-Phase Enhancement (CPGPS), which correct for any incongruity between the phase and can use an additional clock using a method to include but not restricted to the L1 carrier wave which can correct for non-instantaneous imperfect correlation of transmitter-receiver correlation.

Another embodiment can include a method for precision that can include but is not restricted to Relative Kinematic Positioning (RKP).

Another embodiment can include a method for precision that can include but is not restricted to using a clock that is not synchronized to Coordinated Universal Time (UTC), a method that is synchronized to GPS time, a method that is independent of GPS time and UTC (Non-UTC and non-GPS; independent coordinated time (ITC); International Atomic Time (TAI) or any combination of TAI, UTC and GPS and ITC.

In one embodiment ITC can be a time that is set independent of all standards and is used only for the local LPS.

Another embodiment can include a method for precision that can include but is not restricted to knowing the precise distance between the transmitters, receivers or a combination of transmitters and receivers. This precise distance can be determined using methods to include but not restricted to lasers, ultrasound, and electromagnetic measuring devices and other methods for measurement to include but not restricted to kinetic physical measuring techniques to include but not restricted to rulers.

Knowledge of the fixed distance between transmitters, receivers or combination of transmitters and receivers can be used to set the clock or distance or precision of location more precisely and can be used to eliminate or reduce errors to include but not restricted to the partial wavelength, wavelength off-set, time incongruence, mathematical assumptions or any combination of these errors.

Another embodiment to include but not restricted to synchronizing the receiver and the transmitter clocks using methods to include but not restricted to one or multiple wavelength sampling and correlation and comparing these wavelengths, tuning the clocks using a method to include but not restricted to using the known distance between the fixed receivers and transmitters to synchronize and correlate time and distance using one or multiple wavelengths, lasers, or other electromagnetic or non-electromagnetic measuring tools. Some embodiments may include but is not restricted to triple differencing which subtracts the receiver differences from Time A compared to that of Time B. In one embodiment the triple difference method can use three independent time pairs to solve for a receivers location position.

The LPS can be positioned onto the patient in one or more locations. In one embodiment the LPS device can be affixed directly to the body using various methods to include but not restricted to adhesive, tapes, elastic, cloth and Velcro. In another method the GPS device can be affixed indirectly to the body using a method to include but not restricted to a garment, a mask, a helmet, or an apparatus designed to mold to a body part to include but not restricted to caps, frames, bands, garments. An external source can also be attached to the body using methods of attachment to include but not restricted to adhesives, bandages, membranes, injections into the skin, sutures in the skin, bands and Velcro and straps, earrings, tattoos, and skin-piercings or internal and external methods can be used and combined to include but not restricted to swallowed, inhaled, injected, place onto, into or through the skin or mucosa or an orifice.

One embodiment the LPS device can be used but is not restricted assist in patient positioning. This method can be used to include but not restricted to assist radioactivity and thermography correction and localization methods by more precisely superimposing the body structures and providing for more accurate image correction. The LPS can be used for correction methods and for localization method or a combination of the correction method and localization method. The LPS method can be used with currently utilized methods for image creation and quantitative and qualitative methods that can include but not restricted to CT and PET or correct quantization to include but not restricted to Gaussian, linear or exponential curve filters.

In some embodiments, an LPS system includes a plurality of static components distributed in fixed locations relative to one another about a living body and at least one locator component affixed relative to the living body, the plurality of static components and locator components being operable to communicate effective to define a location of the at least one locator component. A computer system is in data communication with at least one of the plurality of static components and the at least one locator component. The computer system may be configured to determine a location of the locator components from one or more outputs of one or both of the plurality of static components and the at least one locator component.

In some embodiments, the one or more outputs include at least one static component output from the plurality of static components and the at least one locator component is operable to transmit signals. The plurality of static components may be operable to detect the signals and produce the static component output representing a location of the at least one locator component.

In some embodiments, the one or more outputs include at least one locator component output from the at least one locator component; wherein the plurality of static components are operable to transmit signals; and wherein the at least one locator component is operable to detect the signals and produce the locator component output representing a location of the at least one locator component.

In some embodiments, the plurality of static components and the at least one locator component are both operable to communicate with one another by transmitting and receiving signals.

In some embodiments, the plurality of static components and the at least one locator component are positioned within a device that can shield a body or body part or space from external electromagnetic signals or energetic or mechanical signals that can interfere with the precision of the LPS system and in one embodiment can be composed of copper and in this embodiment can be referred to as a faraday cage. The faraday cage may conform to a head of the living body. In some embodiments, the faraday cage is coextensive with a plurality of walls of a room.

In some embodiments, the at least one locator component is fastened to a surface of the living body.

In some embodiments, the computer system may be configured to direct an instrument to administer a treatment to the living body based on the location of the at least one locator component.

In some embodiments, the at least one locator component has enhanced detectability in a non-visual imaging modality. The LPS system may include an imaging system operable to image the living body in the non-visual imaging modality. The computer system may be operably coupled to the imaging system and be configured to relate a first portion of an image generated according to an output of the imaging system to the location of the at least one locator component based on at least one second portion of the image corresponding to the at least one locator component.

In some embodiments, the at least one locator component is at least one first locator component and the LPS system further includes at least one second locator component affixed to an object and in data communication with the computer system. In some embodiments, the computer system is configured to detect a relative position of the at least one first locator component relative to the at least one second locator component according to the one or more outputs.

In some embodiments, the computer system is further configured to control positioning of the object relative to the living body using the relative position of the at least one first locator component to the at least one second locator component.

In some embodiments, the object is an implantable device and the at least one first locator component is positioned proximate an engagement point of the implantable device within the living body. In some embodiments, the computer system is further configured to periodically measure the relative location of the object to the living body using one or more outputs subsequent to placing the implantable device within the living body. In some embodiments, the object is a surgical instrument.

In some embodiments, the object is affixed to a robotic mechanism operably coupled to the computer system and the computer system is further configured to control the robotic mechanism according the one or more outputs.

In some embodiments, the first locator component includes a plurality of first locator components and the second locator component includes a plurality of second locator components. The computer system may be configured to measure the orientation of the object relative to a portion of the living body engaging the second locator components based on the one or more outputs.

In some embodiments, the at least one locator component has enhanced detectability with respect to a non-visual imaging modality, such as at least two non-visual imaging modalities.

In some embodiments, the at least one first locator component is within the living body. In some embodiments, the at least one first locator component is further configured to detect at least one parameter of the living body.

In some embodiments, the plurality of static components are affixed within a man-made confined space.

In some embodiments, an LPS system includes a plurality of static components affixed relative to one another about a living body and at least one first locator component positioned affixed to the living body and operable to receive signals from the plurality of static components. The system further includes at least one second locator component affixed to an object, the plurality of static components and at least one first component operable to communicate effective to establish locations of the at least one first locator component and at least one second locator component. The computer system may be in data communication with the at least one first locator component and the at least one second locator component and configured to detect one or more outputs of at least one of the plurality of static components, the at least one first locator component, and the at least one second locator component. The computer system may further be configured to measure a position of the second locator components relative to the first locator components according to the one or more outputs.

In another embodiment the methods for localization described above can be applied to an organ or structures other than the parathyroid or thyroid and can include but is not restricted to the musculoskeletal system to include but not restricted to ACL graft placement, hardware surgical placement and kidney, heart and neuro-endocrine tumors diagnosis and treatment.

In another embodiment the methods for image correction can be applied to an organ other than the parathyroid and can be used for diagnosis, treatment or a combination of diagnosis and treatment and include but is not restricted to the parathyroid, thyroid, other endocrine organs, the musculoskeletal system, the reproductive systems, the kidney, heart and neuro-endocrine organs or tumors.

Another embodiment can include but is not restricted to a sensing device or method for parathyroid identification to include but not restricted to thermography, heat sensitivity and near infra-red, infra-red detection or imaging or a combination of imaging and detection where these methods can be used to identify and diagnose the location of the abnormal parathyroid gland which is more vascular and exudes more heat than other less vascular thyroid and other local tissue. This can be used for diagnosis or treatment or a combination of diagnosis and treatment to include but not restricted to the use of near infra-red, infrared other electromagnetic wavelength analysis.

Another embodiment can include but is not restricted to a heat sensing parathyroid identification method where the thyroid tissue is suppressed and the vascularity reduced which reduces the heat generated by the thyroid and provides greater conspicuity between the parathyroid and the thyroid and allows the parathyroid to be more easily detected. One method for reducing thyroid activity can include but is not restricted to propylthiouracil and methimazole (Tapazole) and thiourea and thiouracil and their derivatives.

Another embodiment can include but is not restricted to a heat sensing parathyroid identification method where the parathyroid gland is hyper-stimulated using methods to include but not restricted to the administration of thiazide derivatives such as hydrochlorothiazide, or inorganic phosphates. The stimulation of the abnormal parathyroid increases the heat production and blood flow of the parathyroid gland thyroid and provides greater conspicuity between the parathyroid and the thyroid and allows the parathyroid to be more easily detected.

One embodiment can include but is not restricted to a method where the standard Tc-99 Sestimibi is used in conjunction with a method where the thyroid tissue is suppressed and the vascularity reduced which reduces the radioactive uptake by the thyroid. This can provide greater conspicuity between the parathyroid and the thyroid and allows the abnormal parathyroid gland to be more easily detected. One method for reducing thyroid activity can include but is not restricted to elemental iodine and potassium iodine administration to include but not restricted to lugol solution doses in the range of approximately 15 mg/day for infants, 65 mg/day for children and 130 mg/day for adults, propylthiouracil and methimazole (Tapazole) and thiourea and thiouracil and their derivatives and perchlorate, pertechnetate and thiocyanate. This can be given prior to the Tc-99 Sestimibi injection and imaging. This represents a new use for these thyroid suppression medications.

Another embodiment can include but is not restricted to a method where the standard Tc-99 Sestimibi is used for detection and localization of the abnormal parathyroid gland in conjunction with a method where the parathyroid gland is hyper-stimulated. The stimulation of the abnormal parathyroid increases the uptake and radioactivity of the parathyroid gland and provides greater conspicuity between the parathyroid and the thyroid and allows the abnormal parathyroid gland to be more easily detected. One method for hyper-stimulating the parathyroid gland can include bit is not restricted to the administration of thiazide derivatives such as hydrochlorothiazide, or inorganic phosphates. Methods to alter uptake by the parathyroid can also include but are not restricted to administration of medications prior to the Sestamibi exam to include but not restricted to calcium and calcium derivatives such as calcium carbonate.

One embodiment can include a method where the electromagnetic light spectrum is used to localize an organ to include but not restricted to a parathyroid adenoma, A parathyroid adenoma because of its unique cellular make-up and its blood supply is orange. Using a method where a specific wavelength in the electromagnetic spectrum is assigned to the parathyroid to include but not restricted to a central range approximating 590 to 625 nm the reflection, translucence, transducing capacity or the absorption of this wavelength can be used to detect and localize a parathyroid adenoma. Depending on the size and vascularity of the parathyroid adenoma the specific wavelength may vary from this range. The method can be used to distinguish the parathyroid tissue from the adjacent supportive tissue and the thyroid, which have a reflection, translucence, transducing capacity or the absorption of this wavelength different from the parathyroid adenoma. Other specific electromagnetic wavelengths can be used to identify other organs or body tissues. This method can include but is not restricted to incorporating photospectroscopy and PAI and optical and endoscoptic methods.

In another embodiment the methods and uses and devices described in this embodiment can be used on living creatures to include but not restricted to humans.

In another embodiment frames or frame like devices can be used to but are not excluded to being used to fix in place the radioactive sources, the positioning devices, surgery and surgical assistance devices, and to fix a structure in a fixed or relatively fixed mechanical position.

The application of these methods and embodiments can include but is not restricted to integrating these methods and processes and embodiments with or into a Computer Assisted/Aided Device (CAD) or platform or program.

The same methods for acquiring data for target localization can include but are not restricted to parathyroid, thyroid and other body parts can use but are not restricted to radioactivity.

The localization methods can be used to assist treatment of parathyroid gland dysfunction. Surgical. Percutaneous, Tightly Targeted minimally invasive, and non-invasive and non-surgical approaches to parathyroid treatment can benefit from precise localization of the abnormal parathyroid gland and localization techniques described in this patent can be combined with surgical and invasive, minimally invasive and non-invasive treatment techniques to include for both localization and treatment techniques to include but not restricted to energy that can include but is not restricted to Radiofrequency ablation (RF) and microwave (MW) and laser (L), Ultrafast Laser (UL), Cryotherapy (CryT), High Intensity Focused Ultrasound (HIFU), Radioactive Therapy (Brachytherapy: BrT), Irreversible, Electroporation (IRE), Electrical Current Therapies, Electrocautery, Magnetic Resonance (MR), Ultrasound, (US), Cautery and kinetic or mechanical energy, Thermal energies both heat and cold and mechanical or kinetic energies and with adjuvant combinations that can include but are not restricted to medication delivery, Medication packets, blood flow reduction, Chemical and Medication Ablation, Activation and Deactivation and Modulation Therapy, Adhesives and Glues and Molecular Crystal and Lattice therapies, Target Tissue Delivery Device Therapies, Peptide and Biological Conversion Therapies, MR and RF and Magnetic External Heating Therapies, Hyperthermia with Adjuvant Therapy, Hypothermia with Adjuvant Therapy, Local protective therapy in the Vicinity of the Target Organ Therapy, Suction and Expansion Therapy, Positive Pressure and Expansion Therapy, Mechanical Ablation Therapy and Combinations of therapies. One embodiment can include but is not restricted to a percutaneous placement method of a device can be guided using imaging or LPS systems of locators and the device can be placed adjacent to the parathyroid and an energy activating substance such as but not restricted to a photo or acoustic sensitive substance can be inserted into or around the parathyroid or a parathyroid blood vessel and then the activating energy can be initiated which can result in but not restricted to ablating all or a portion of the parathyroid and the energy or activating substance can be created to have variable amounts of ablating or stimulating or treatment capacities which are dependent on but not restricted to the energy intensity or wavelength or periodicity or pulsatility, which is serve as a control of the treatment and also control the exposure of the local environment to that treatment to minimize undesired side-effects of the treatment.

In another method the ultrasound transducer is combined and/or incorporated with a positioning or locator device such that the ultrasound transducer position can be identified and recorded within the coordinates of the GPS or LPS coordinate system.

In some embodiments, a method for measurement includes providing an object having one or more first markers affixed thereto and affixing one or more second markers to a living body. The one or more first markers and one or more second markers are then detected, by a computer system using a non-visual imaging modality. The computer system may measure a relative location of the object to the living body using the one or more first markers and one or more second markers. For example, in some embodiments, the method may include controlling positioning of the object relative to the living body using the relative location.

In some embodiments, the object is a prosthesis and the one or more second markers are positioned proximate an engagement point of the prosthesis with the living body. The prosthesis may be configured to conform to the engagement point. In some embodiments, the method may monitoring a position of the prosthesis relative to the engagement point subsequent to embedding of the prosthesis in the living body.

In other embodiments, the object is a surgical instrument. The object may be affixed to a robotic mechanism and the computer system may be configured to actuate the robotic mechanism according to the relative locations of the one or more first markers and the one or more second markers.

In some embodiments the one or more first markers and one or more second markers include GPS receivers or LPS receivers, such as the GPS and LPS receivers described herein. The GPS or LPS receivers may transmit data to the computer system to enable the computer system to determine the locations of the GPS or LPS receivers.

In some embodiments, the one or more first and second markers have enhanced detectability with respect to the non-visual imaging modality. The one or more first and second markers may have enhanced detectability with respect to the non-visual imaging modality and at least one other non-visual imaging modality.

In some embodiments, the one or more first markers include a plurality of first markers. The plurality of first markers may be secured to a surface of the living body or implanted in the living body. The computer system may be configured to measure an orientation of the object relative to a reference direction established by the plurality of second markers. In some embodiments, the one or more second markers include a plurality of second markers. The computer system may be configured to determine the reference direction according to the plurality of first markers and determine the orientation of the object, e.g. relative to the reference direction, according to the plurality of second markers.

In some embodiments, at least one of the one or more second markers includes at least one sensor configured to detect at least one parameter of the living body. The one or more second markers may further include transmitters for transmitting data representing the at least one parameter.

In some embodiments, the object is a portion of an imaging device. The portion of the imaging device may be configured to be insertable within the living body.

In some embodiments, an imaging system is operably coupled to the computer system. The computer system may be programmed to detect locations of the first and second markers in an output of the. As noted above, the first and second markers may have enhanced detectability in one or more non-visual imaging modalities, such as any of the imaging modalities described herein.

Elastomeric Gel MRI Markers:

The use of skin markers is important in Magnetic Resonance Imaging (MRI). Skin markers have two primary functions. First markers can be placed at the site of a patient's pathology. This provides a method by which the radiologist and technician can reliably identify and scan the area being evaluated. The second use of skin markers is to provide a reference point to enable the technician and radiologist to number the vertebral bodies. This is particularly important in the thoracic spine region where distinctive bone landmarks are often absent or less reliable than in the lumbar or cervical regions.

Criteria for an optimal marker should include (1) reliable visualization on all appropriate sequences, (2) minimal to no artifacts, (3) a variety of sizes and shapes appropriate for the multiple anatomic sites being investigated and the various applications being performed (4) minimal to no distortion of the local anatomy, (5) ability to conform to the contours of the local anatomy, (6) easy to use and adhere to skin, (7) biologically safe and non-toxic with MRI use, (8) preferably not a liquid which can spill (9) inexpensive to produce, and (10) a shape that can be produced that is not confused with anatomic shaped structures and (10) in some embodiments can be used with multiple imaging modalities to include but not restricted to MR, CT and Ultrasound.

The most common markers in use today include peanuts, soy sauce packages, fish capsules. Other markers that have been described in the literature but which are not in daily routine usage are Lipiodol markers, Gadolinium-DTPA filled tubes, non-magnetic wires inserted into the skin for breast biopsy and discs of an un-hydrated co-polymer of vinyl pyrrolidone and phenyl methacrylate subsequently hydrated in a solution of copper sulfate. Each of the above has one or more significant limitations.

Many of the above are seen well on some but not on other sequences. Markers such as fish oil capsules and gadolinium filled tubes that contain predominantly fat or T1 shortening materials are easily detected on T1 weighted sequences but are poorly visualized or not seen at all on T2 weighted sequences. For markers that contain primarily water-based materials the reverse is true. They are seen well on T2 weighted sequences but are poorly or not seen on T1 weighted sequences.

Additional limitations occur with the various markers because they have to be packed in firm or hard or poorly or non-conforming coatings or capsules and these can confuse the interpretation between distorted anatomy and pathology. Fish oil capsules and peanuts distort the local anatomy in superficial masses. Soy sauce packages, which contain abundant amounts of water may generate artifacts on T2 weighted sequences. Also, soy sauce packages and fish oil capsules can and do leak.

Other limitations include the inability to use the same or a similar marker for different imaging modalities. For example MR markers such as fish oil capsules can be difficult to see with CT and ferro magnetic or strongly paramagnetic substances or metals and wires placed onto the skin for CT are not practical for routine non-invasive MRI usage. Additional limitations of current markers include but are not restricted to unreliable visualization of the marker on all appropriate sequences, many and variable artifacts, limitations in sizes and shapes appropriate for the multiple anatomic sites and the various application being investigated, distortion of the local anatomy, inability to conform to the contours of the local anatomy, and shapes that are confused with anatomic and biological structures, biologically unsafe and toxic and usefulness with only one imaging modality and not able to be seen or used with multiple imaging modalities.

In some embodiments, an elastomeric gel MRI marker utilizes a block copolymer with plasticizing oils. Although these gels can be manufactured with many possible combinations of polymers depending on the T1 and T2 weighted imaging characteristics desired, the current embodiment employs a triblock copolymer composed of 25 to 50% (plasticizing oils). In the current embodiment the gel can include but is not restricted to be encapsulated fully or partially with a membrane or coating that can include but is not restricted to a firm or flexible or plastic or wax covering. The gel markers can be produced with no membrane or the gel marker can have no coating or membrane.

In some embodiments, a marker for imaging applications includes a flexible structure conformable to a part of a living body, the flexible structure formed of a gelatinous elastomer. The flexible structure further includes one or more materials effective to provide enhanced detectability in a plurality of imaging modalities in addition to the human visible spectrum. In some embodiments, at least one surface of the flexible structure at least one of is tackified and has an adhesive material secured thereto.

In some embodiments, the flexible structure is secured to a rigid frame, the frame having at least one surface configured to conform to a portion of the living body. In other embodiments, the flexible structure is secured to a wearable item configured to fit over a portion of the living body. In some embodiments, the flexible structure secures to a portion of a hook-and-loop fastening system.

The one or more materials of the marker may each have a signature in the plurality of imaging modalities that is distinguishable from tissue adjacent the flexible structure in the living body. The plurality of imaging modalities may include at least two of ultrasound, x-rays, computer tomography, magnetic resonance imaging, and nuclear medicine imaging. In some embodiments, the plurality of imaging modalities include at least two magnetic resonance imaging sequences selected from: T-1 spin echo, T-2 spin echo, gradient echo, turbo spin echo, spectroscopy and inversion recovery, fluid attenuated inversion recovery, and short T-1 inversion recovery.

The one or more materials may be substantially homogenously mixed with one another and may be homogeneously mixed with the gelatinous elastomer. In some embodiments, the flexible structure defines a cavity and at least one of the one or more materials is positioned within the cavity. In some embodiments, an electronic device is positioned within the cavity. The electronic device may include at least one sensor operable to detect at least one of an environmental factor and a biological process of the living body, and a transmitter coupled to the sensor and operable to transmit a representation of at least one output of the at least one sensor. The marker may include a radiation exposure sensor.

In some embodiments, the flexible structure has a non-natural perimeter shape. For example, the non-natural perimeter shape may be at least one of a circle, triangle, square, and ellipse. In some embodiments, the flexible structure defines an annular shape having a void providing accessibility to skin of the living body to which the marker is secured. In some embodiments, the gelatinous elastomer is resiliently deformable.

In another embodiment, a marker for imaging applications includes a flexible structure conformable to a part of a living body. The flexible structure may incorporate first and second materials. The first material may be at least one of a hydrophilic and a water-like material at least one of a lipophilic material, lipid, oil, and fat-like material. The second material may be at least one of a hydrophilic and a water-like material. The first and second materials may be mixed together, such as homogeneously mixed. In some embodiments, the flexible structure includes a gelatinous elastomer, such as a resiliently deformable gelatinous elastomer. The gelatinous elastomer may incorporate the first material and second material in a block copolymer. In some embodiments, the first material has a T-1 weighted sequence result having an intensity at least as great as fat of the living body and the second material has a T-2 weighted sequence result at least 25% as great as that of cerebrospinal fluid of the living body. In some embodiments, the second material has a T-2 weighted sequence result that is one of 10% as great, 25% as great, 50% as great, 75% as great, 90% as great, and 100 percent of that of cerebrospinal fluid of the living body. But depending on the local tissue environment the T1 marker difference from the T2 or the T2 marker difference from the T1 environment can be reduced to less than 10 percent or greater than 100 percent of absolute values.

In some embodiments, the marker has enhanced detectability in an imaging modality other than the human visible spectrum, the imaging modality including at least one of ultrasound, x-rays, computer tomography, and nuclear medicine imaging.

A method for diagnosing a condition may include applying one or more markers to a living body, each of the one or more markers having a different marker signature in a first imaging modality. The method may further include generating an image of at least a portion of the living body including the one or more markers using the first imaging modality and comparing a tissue signature of a representation of tissue in the living body in the image to the marker signatures of a representation of the one or more markers in the image. A condition of the tissue may then be diagnosed according to the comparison. The steps of comparing and diagnosing may be performed by a computer system. In some embodiments, the one or more markers may include a plurality of markers each having a different combination of T-1 weighted compounds and T-2 weighted compounds.

Diagnosing the condition of the tissue according to the comparison may include determining at least one of bone marrow composition, extent of fatty liver condition, extent of fibrotic liver condition, extent of osteoporosis, presence of diabetes, degree of pancreatic fatty replacement, presence of adenomas, presence of tumors, presence of aggressive tumors, body fat calculations, and presence of metabolic replacement diseases.

DETAILED DESCRIPTION OF THE PREFERRED EMBODIMENT

Figure 1:
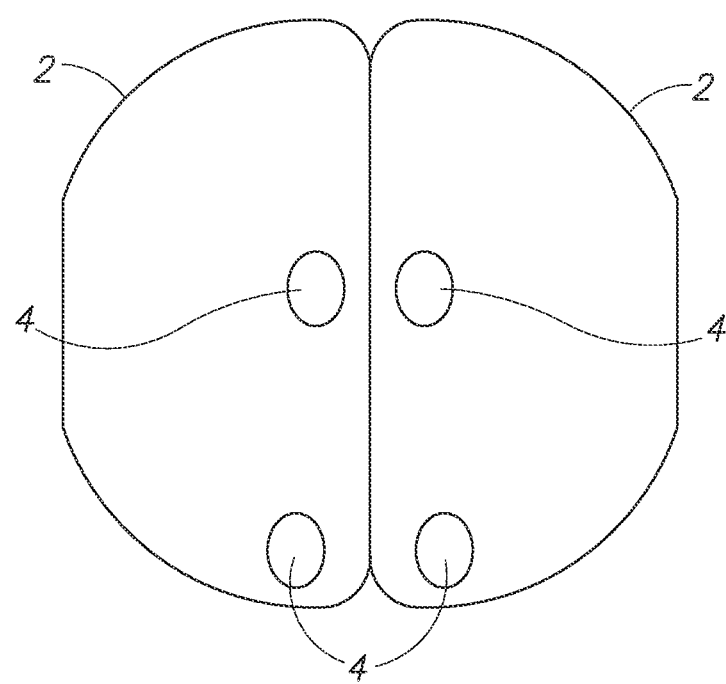
FIG. 1 depicts the anatomic relationship of the four parathyroid glands in their general relationship to the thyroid.

FIG. 1 depicts the anatomic relationship of the four parathyroid 4 glands in their general relationship to the thyroid 2. Most people have four parathyroid 4 glands (some have fewer than four and some have more than four parathyroid 4 glands). These parathyroid 4 glands lie (behind) the Thyroid 2 gland in the lower neck. They are separate from your thyroid 2 gland. The parathyroid 4 gland controls Calcium levels in the bones and blood. Despite this general description of the parathyroid 4 glands location 66 in reality Parathyroid 4 glands are variable in location 66 and can reside as craniad as the submandibular glands and as caudad as the lower mediastinum. Although most individuals have one abnormal parathyroid 4 gland some individuals can have two or more abnormal parathyroid 4 glands. The accurate pre-surgical and intra-operative identification of the location 66 of the normal and abnormal parathyroid 4 glands is paramount to successful treatment of hypercalcemia and hyperparathyroidim with the fewest complications.

Figure 2:
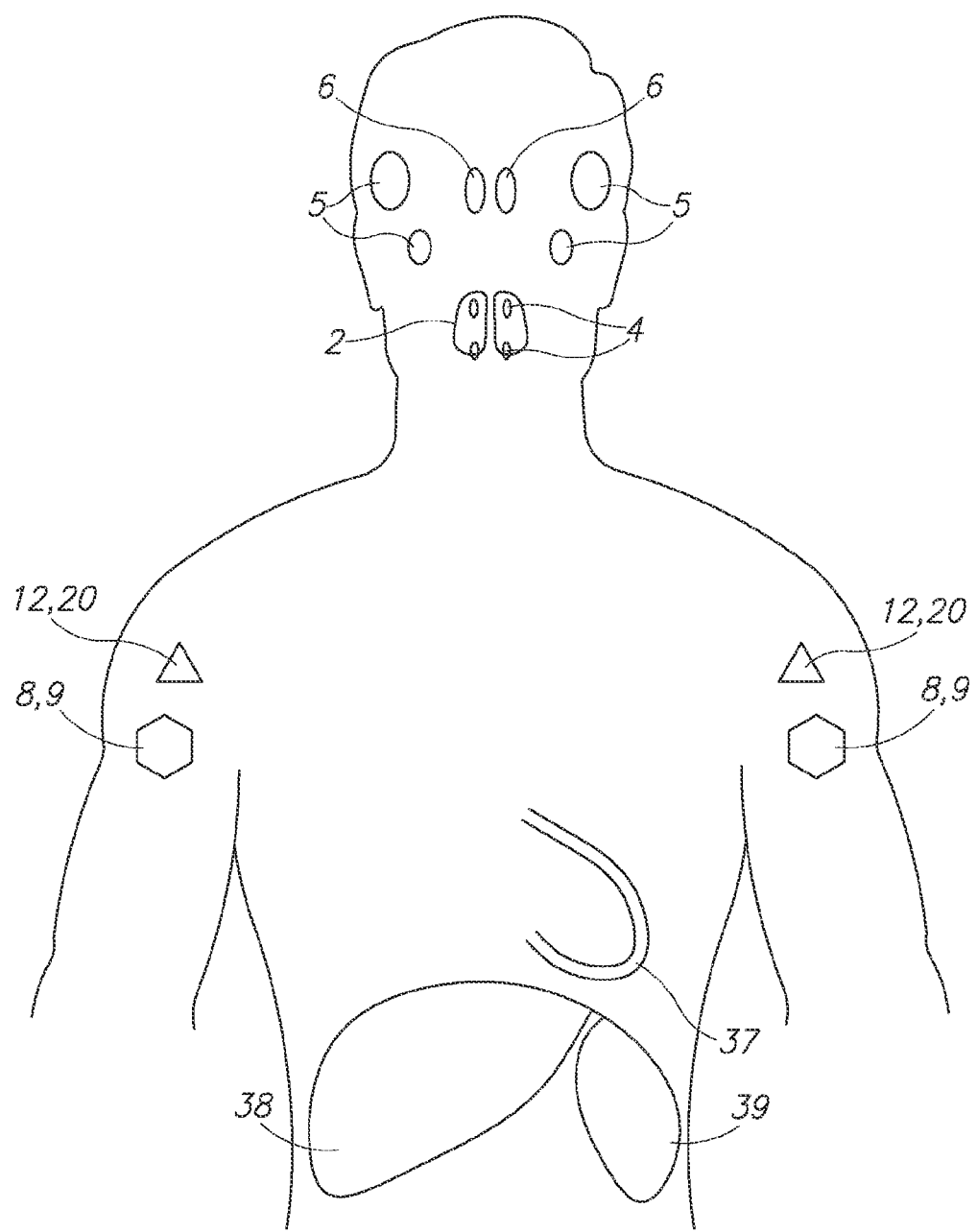
FIG. 2 depicts the four parathyroid glands and thyroid in relationship to other organs that take up radioactive Sestamibi in the body and can be used to realign and to improve parathyroid imaging through temporal mapping and realignment, such as by using external markers can be used to assist alignment.

FIG. 2 depicts the four parathyroid 4 glands and thyroid 2 in relationship to other organs 7 of the body 7 that take up radioactivity in the body 7, such as sestamibi or some other radioisotope or other substance for enhancing detectability of an organ in a non-visual imaging modality. The organs 7 and can be used to realign and to improve parathyroid 4 imaging through temporal mapping and realignment. In the region of the head and neck the salivary glands 5 and the nasal and oral and nasal mucosa 6 take up activity and retain radioactivity 9. In the torso, other body parts 7 that can be used as references to realign the images include the heart 37, liver 38 and spleen 39. Both the outline points 40 and one, or more than one, points 40 including an internal or center points 40 can be used to determine location 66 of the body organ part 7 when used in the realignment protocol. Radioactive external source markers 8, sensors 20, locators 12, or the like, can be used to assist alignment.

Figure 3A:
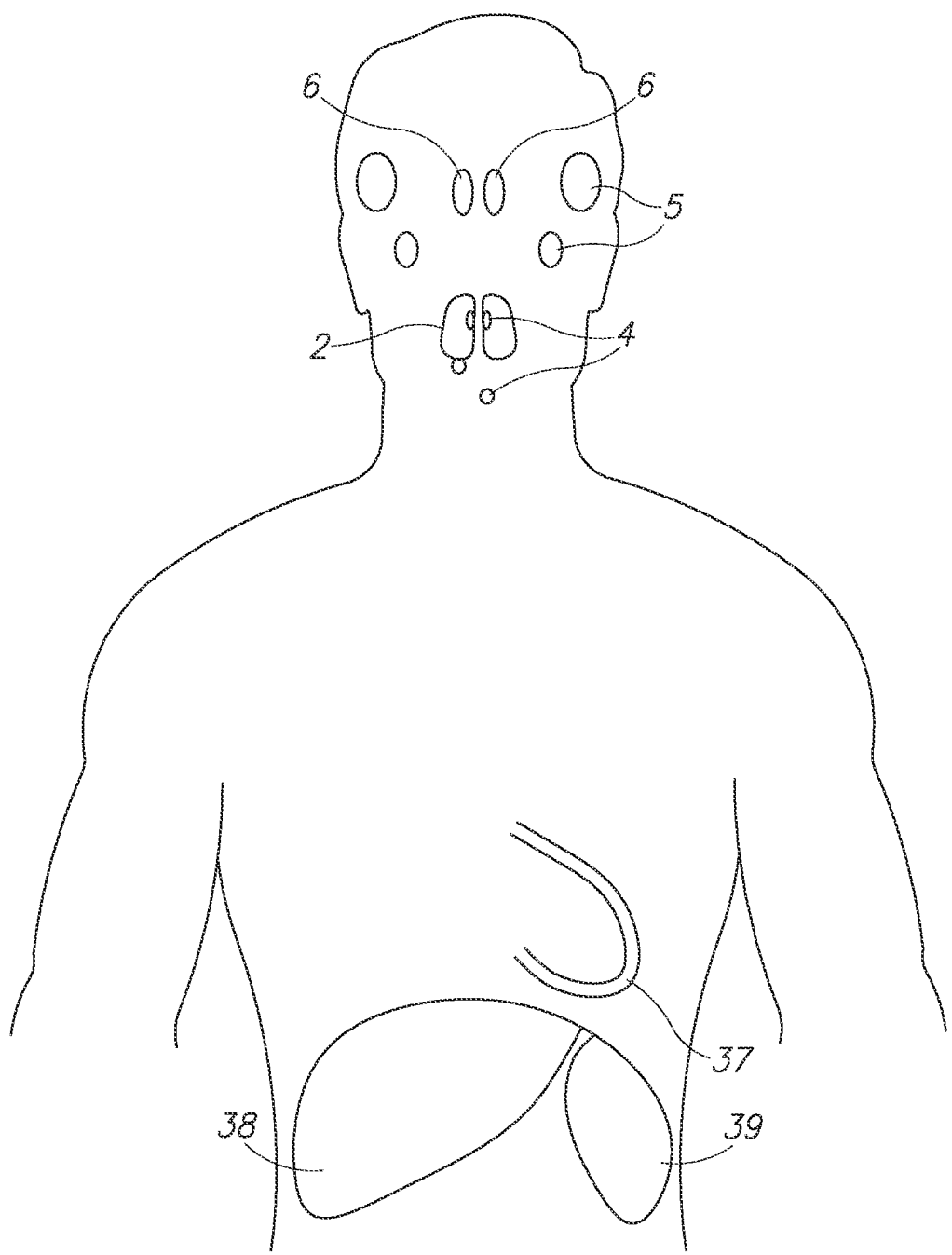
FIG. 3 depicts an example of alignment FIG. 3A and non-alignment FIG. 3B and then realignment FIG. 3C. By using the mechanical or mathematical modeling program 24, the misalignment in FIG. 3B which can be caused by a change in position from the initial position FIG. 3A can be corrected by mechanical or mathematical modeling to return to a similar position FIG. 3C as was present in the initial position FIG. 3A.
FIG. 3D is enhanced data after the alignment and/or modeling and/or enhancement programs have been applied.
Figure 3B:
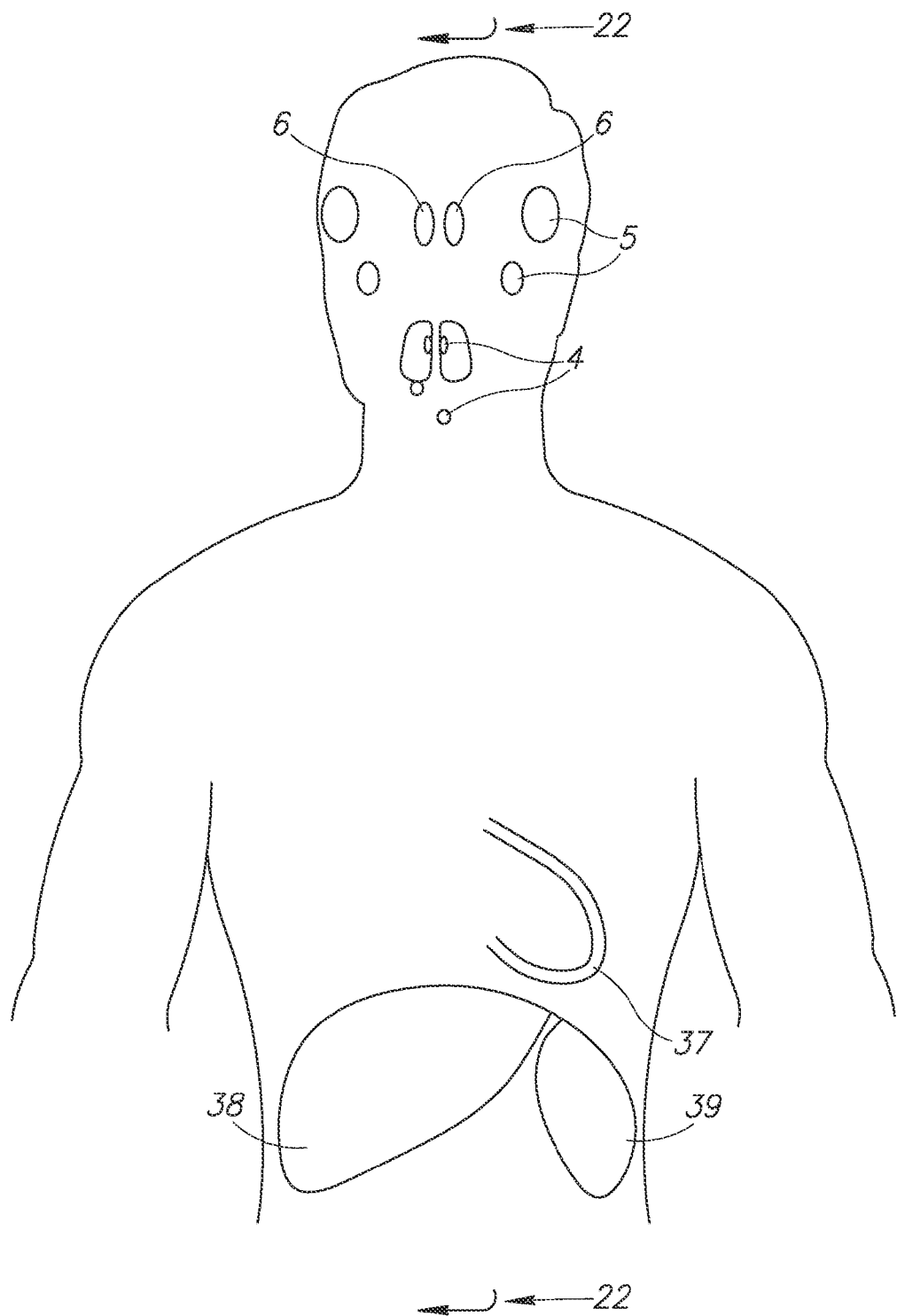
Figure 3C:
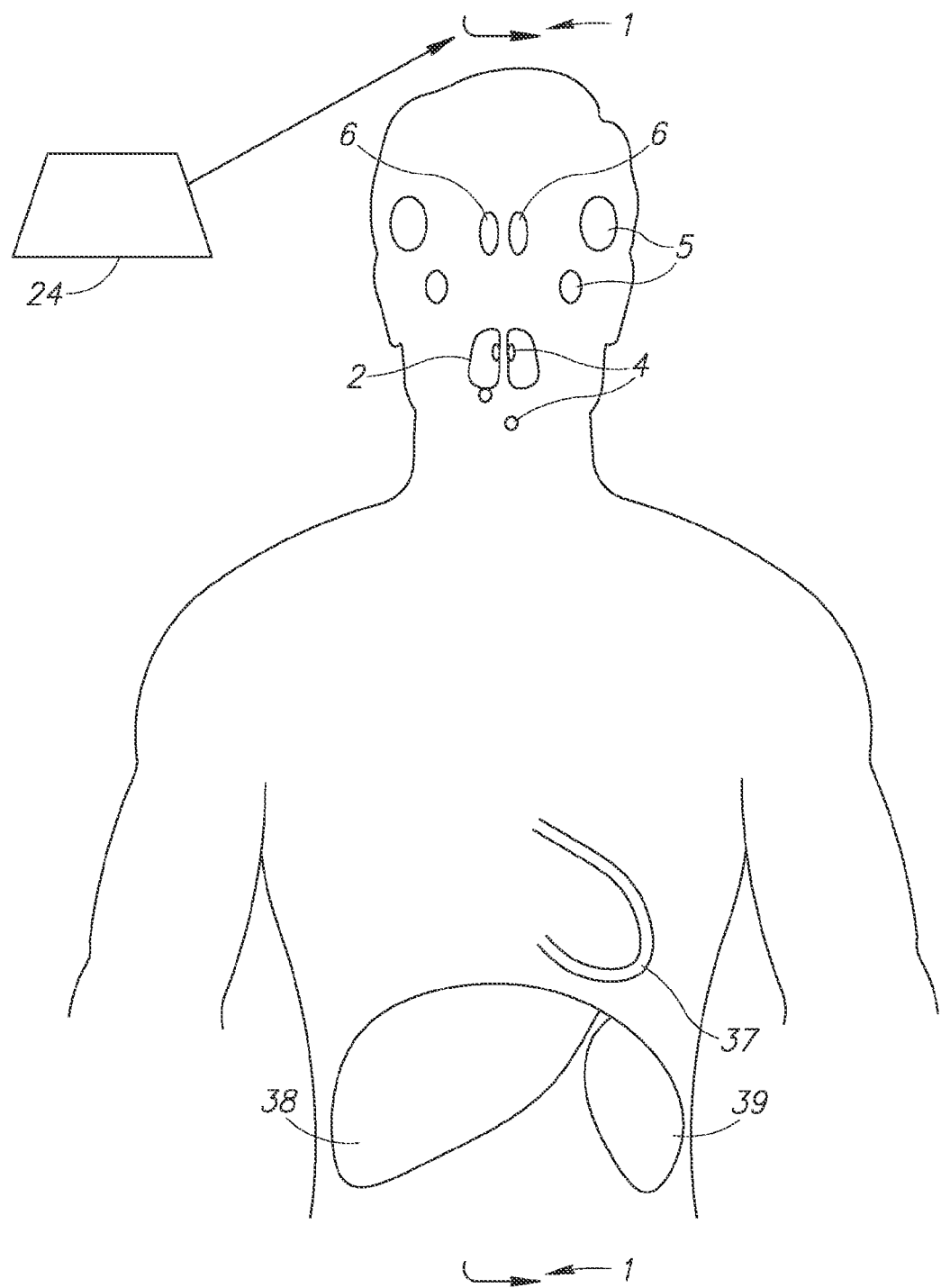

FIGS. 3A-3C depicts one embodiment method for alignment 1 and modeling 24. FIG. 3A illustrates a temporal point and corresponding image and data. FIG. 3B illustrates a later temporal point and corresponding image and data. FIG. 3C is the post processing realignment 1 image that corrects temporal point B's image such that it is returned to the alignment 1 of temporal point A's image and data. By using modeling 24 methods to include but not restricted to mechanical or mathematical data and image correction modeling programs 24, the realignment 1 in position of FIG. 3B temporal point B can be performed by modeling correction programs 24 to return FIG. 3B to a similar position/image and data point positions, which can include and are not restricted to voxels and pixels, and is now referred to as FIG. 3C which is now in the initial position of FIG. 3A. After this correction has occurred then one embodiment can include but is not restricted to supplement the new data 42 set with additional modeling 24 that can include but is not restricted to enhancing, reducing, and/or filtering the data points 40 as exemplified in FIG. 3D. In one embodiment the liver 38 and spleen 39 and salivary glands 5 and heart 37 can be used as internal markers of alignment, An external 8 marker 32 can be affixed to the body 7. A mathematical model can be used to assess the movement 22 or the rotation 22 of each of these organs 7 or markers 32. Mathematical modeling 24 can utilize but is not restricted to edge detection, step detection, edge thinning, using a Kirsch operator, pixel or voxel realignment 1 which can include but is not restricted to measuring the number of pixels or voxels or both and comparing the increase or decrease in the number of pixels or voxels in any direction and correcting the movement to align or change in position to or with the original or propositus image. This process can be performed once or more than once to fine-tune or adjust the static target locations.

Figure 4A:
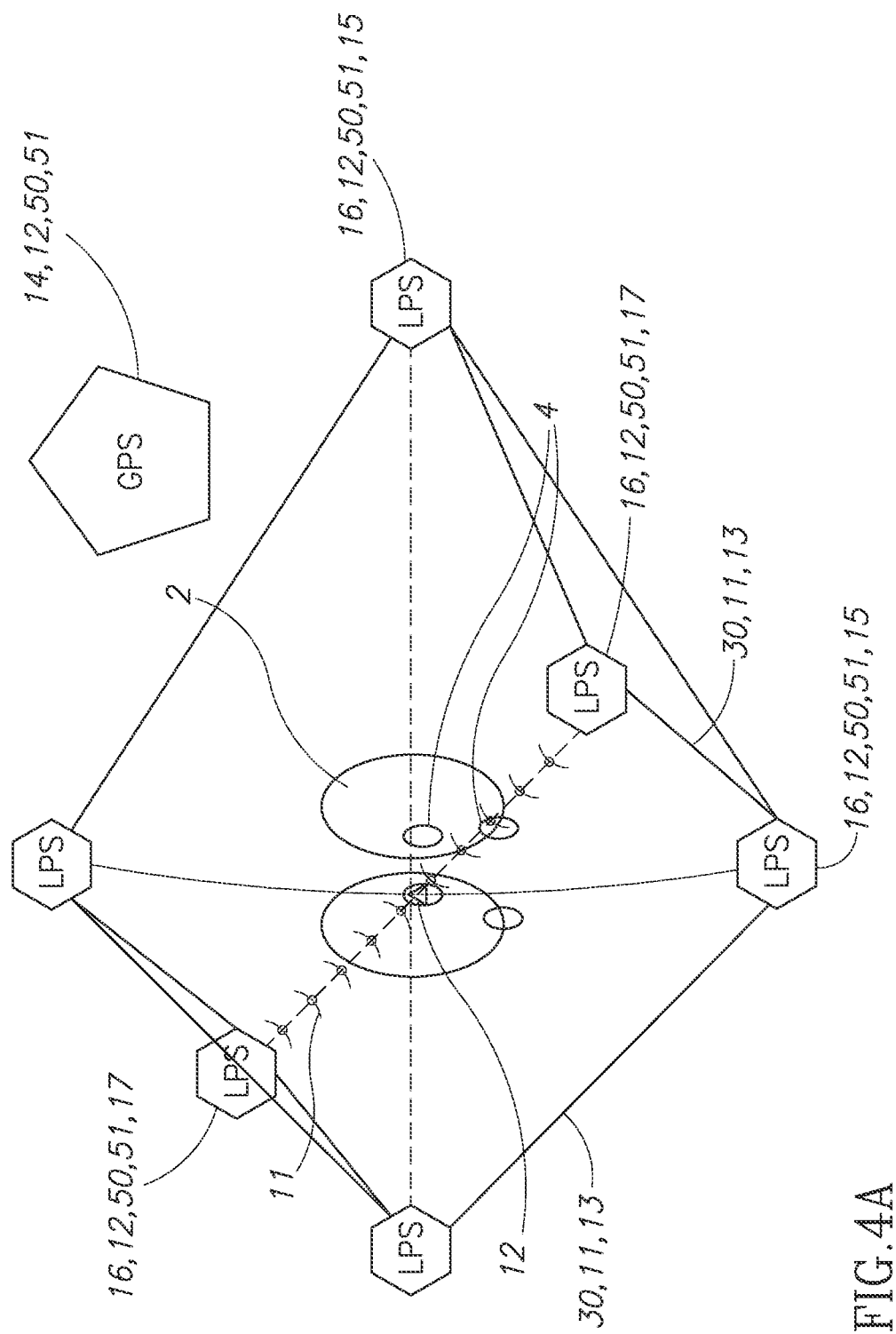
FIG. 4A depicts an external locating device or locator that can include but is not restricted to a Global Satellite Positioning Device (GPS) or a Local Positioning Device (LPS) that can be used to assess the coordinates of the target organ, the parathyroid and thyroid or other body parts with an associated locator on the target organ.
Figure 4B:
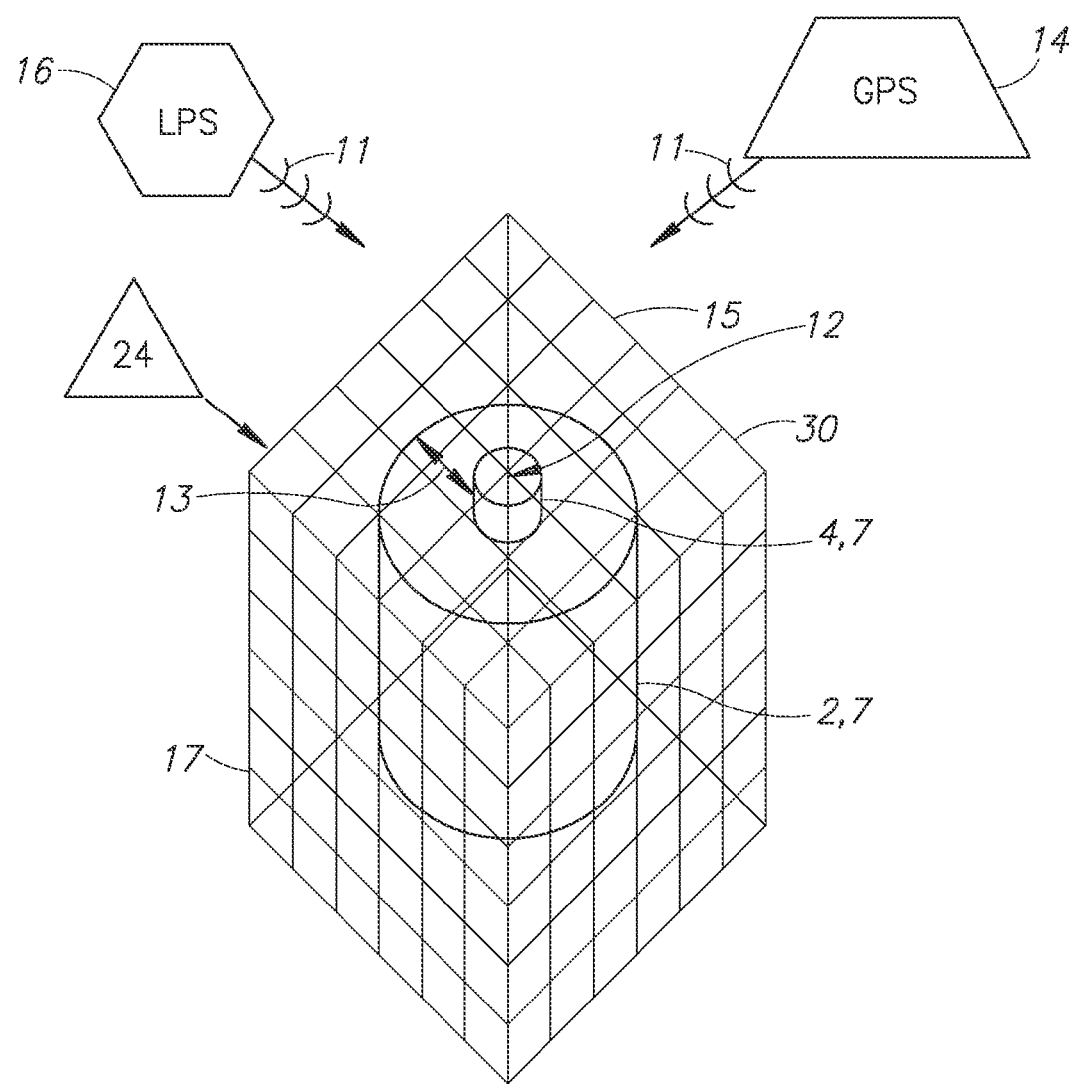
FIG. 4B depicts a coordinate system generated from the LPS or GPS or radioactive or CAD system that can be used to triangulate and locate regions of an anatomic structure.

FIGS. 4A and 4B depict an example of an external locating device 8 or locator 12 that can include but is not restricted to a Global Satellite Positioning Device (GPS) 14 or a Local Positioning Device (LPS) 16 that can be used to assess the coordinates of the target body organ 7 which in some embodiments includes but not restricted to the parathyroid 4 and thyroid 2 but can include other body parts 7 (not depicted) to include but not restricted to joints such as a knee 19, hip 18, shoulder, or body organs 7, such as the heart 37, liver 38 or spleen 39 that can use, but are not restricted to use, an internal or external locator 8 or locator device 12 to assist in localization of the target organ which in this depiction is the parathyroid 4. The GPS 14 system can use standard GPS methods which can be modified to smaller targets. In the LPS 16 method a space can be created which contains transmitters 12, 50 and receiver 12, 51 devices 12 referred to as location devices 12 or locators 12. These locator 12 devices can be positioned strategically within the said space such that their distance is assessed and by combining these locators 12 a grid or coordinate 30 system or map can be generated which can be 2-D or 3-D and in which all points 40 within the grid or coordinate system 30 can be defined or calculated. In the some embodiment there will be fixed locators 12 that create the coordinate system and there will be non-fixed or mobile locators 12 which when positioned in the coordinate system the non-fixed locators can be found or located or defined a position in the grid or map or coordinate system 30. FIG. 4B depicts the coordinates can be generated in two planes if the coordinates are 3-D to include plane one 15 and a plane 17 perpendicular to plane one 15. The non-fixed locator is like a cell phone containing GPS 14 which is located in the larger satellite generated world GPS 14 system. The GPS 14 system is useful for objects that are macro in size with resolutions of about a 12 inches/30 cm but not used for objects in the 0.1 inch/3 mm range. The advantage of the LPS 16 system is that it can more precisely resolve the position of an object in a map or grid or coordinate system 30 in the 0.1 inch or 3 mm or less range which is what is needed for medical applications.

In some embodiments, an actual LPS system may be built into a room and the LPS system defines a 2-D or 3-D grid system and enables visualization of objects smaller than permitted by GPS may be isolated from the GPS system and the environment. In one embodiment an LPS locator system can be limited to a space smaller than a room and that space can be but is not restricted to being portable such as but not restricted to a helmet that is placed over the patient's head and locators with the capacity to send and receive can be distributed about the helmet. In addition, the helmet can be composed of a material to include but not restricted to copper, which in some embodiments is external to the transmitters and receivers relative to the patient. In this embodiment the helmet serves as a Faraday Cage with the locators, transmitters and receivers internal to the Faraday cage with the locators, transmitters and receiver between the Faraday Cage and the patient. A method for signal transfer of information from the locators, transmitters and receivers to the environment, outside of the Faraday cage, can be created by insulating the external portals with sufficient RF insulation.

In one application, a superficial address or location on the body may be determined using the LPS system. This can be used in a manner to find a spot on the body to include but not restricted to find a location on the body to plan a surgery, perform a biopsy, use for treatment such as finding abnormal anatomy and treating that anatomy with methods to include but not restricted to laser light markers to mark anatomy for the biopsy or for the surgical site. The best application may be placing a locator into an Ultrasound transducer and then interrogating the anatomy from that point so that the secondary imaging system is aligned with the part of the body to be interrogated.

In some embodiments, the LPS system can be used to treat a patient with radiation such as gamma knife or external beam radiation especially for superficial lesions. Unlike current methods it does not rely on an ancillary imaging but can be used with ancillary imaging if needed.

In another application, a superficial address or location on the body may be coordinated with an imaging systems, such as a non-visual imaging modality which can include but is not restricted to CT, MR, PET, other Nuclear Medicine, ultrasound or thermography. The locators can be placed onto the patient and an imaging system used to identify the internal anatomy relative to the superficial anatomy. The imaging data and the LPS locators may be used to guide a transducer or other imaging and/or external locators.

In another application, an LPS locator system is in place and one or more than one external LPS locators can be affixed to the patient and one, or more than one locators, may be placed internally within the body. This method can be used with additional imaging systems to include but not restricted to CT, MR, PET, other Nuclear Medicine Ultrasound or thermography. One or more than one locator devices can be used internally and within the patient's body. The locator can be placed on or within a structure to include but not restricted to a prosthesis or implants or can be integrated into a surgical probe or scalpel or a measuring device including devices that measure distances or angles. The locators can be used to guide procedures in the body such as intubations, endoscopies, Nasogastric tube placement, catheters including but not restricted to vascular or hollow viscous catheterizations. In another embodiment, the locators within the body can be used to outline a tumor or infection to measure the increase or decrease in size or location of the tumor or infection.

In some applications, the locators can be placed such that the location of an implanted device that can include but is not restricted to a prosthesis or a device in which the precise location of the implanted device or structure relative to the body part is important or critical.

In some embodiments, a prosthesis such as a knee prosthesis can have locators incorporated into the prosthesis and the adjacent bone can have locators. The position of the prosthesis relative to the bone can be measured precisely This is specifically important since loosening of the prosthesis relative to the bone is difficult to image because the prosthesis is composed of metal which generates significant artifacts with CT and MR and US and MR. This technique will allow real-time analysis of the prosthesis tightness or loosening by measuring the distance between the prosthesis and the bone when it is implanted and then after the surgery when the implant needs to be analyzed for location, mechanics and loosening. Loosening is important because it can be associated with infection, damage to the cement or the bone or prosthesis, or it can be associated with a gap or movement of the prosthesis relative to the bone.

In some embodiments, a sensor can be positioned or integrated into a prosthesis or a graft. This can be used with a locator or combination including the locator. The sensor can have a transmitter and a receiver that can send and receive information as related to the object implanted into the body. In some embodiments an ACL graft can have sensors that can obtain measurements to include but not restricted to tensile strength, bloodflow, infection, inflammatory cells, chemical properties to include but are not restricted to biological properties including but not restricted to temperature, tensile strength, translucence or chemical signatures that can include but are not restricted to lactic acid, glucose, pH, sodium potassium, protein and peptides, fatty acids and carbohydrates. This information can be obtained by acquiring information from or delivering a substance to the structure being interrogated and can include but is not restricted to an energy or a solid or liquid or gas. In one embodiment the information can pertain to but is not restricted to the tensile strength or stretch of the graft, which can include measuring the distance between two locators or sensors at rest and with a stretching force placed upon the graft. Or the sensors can measure pH, oxygen, nitrogen, CO2, or glucose or any combination of these or other biological or non-biological parameters, which can change or vary in the tissue or the environment surrounding the tissue of the graft, which can vary when exposed to a damaging the situation that can include but is not restricted to an infection or breakdown of the graft which may vary one or more than one of the sensed parameters when compared to the steady state or previously measured or normal parameters of the graft to include but not restricted to one or more of pH, oxygen, nitrogen, CO2, or glucose or any combination of these or other biological or non-biological parameters as may occur but is not restricted to an infection with an aerobic or an anaerobic organism. In another embodiment, the sensor can deliver can have but is not restricted to a ceramic or semiconductor sensing chip that can measure or detect flow and can be used to determine the presence or absence of blood flow in the graph. The graft can be exposed to an external energy or substance to include but not restricted to heat or light or ultrasound and the sensory device can measure parameters related to these sensory inputs. Another embodiment can include but is not restricted to an endocrine or exocrine organ that can include but is not restricted to insulin from the pancreas, parathyroid hormone from the parathyroid, gastrin from the stomach, thyroid stimulating hormone (TSH) from the pituitary, thyroid releasing hormone (TRH) from the and thyroid hormone from the thyroid. The sensory device can transmit or receive information. Other biological tissues of the body including but not restricted to a joint graft can be interrogated by this sensing device and can include but are not restricted to joints, eye, kidney, skin, heart and other normal and abnormal body organ and can include but is not restricted to abnormal tissue to include tumors and tumor releasing hormones or peptides or metabolic normal occurring or abnormal occurring biological or non-biological by-products or biologicals of metabolism.

Figure 5:
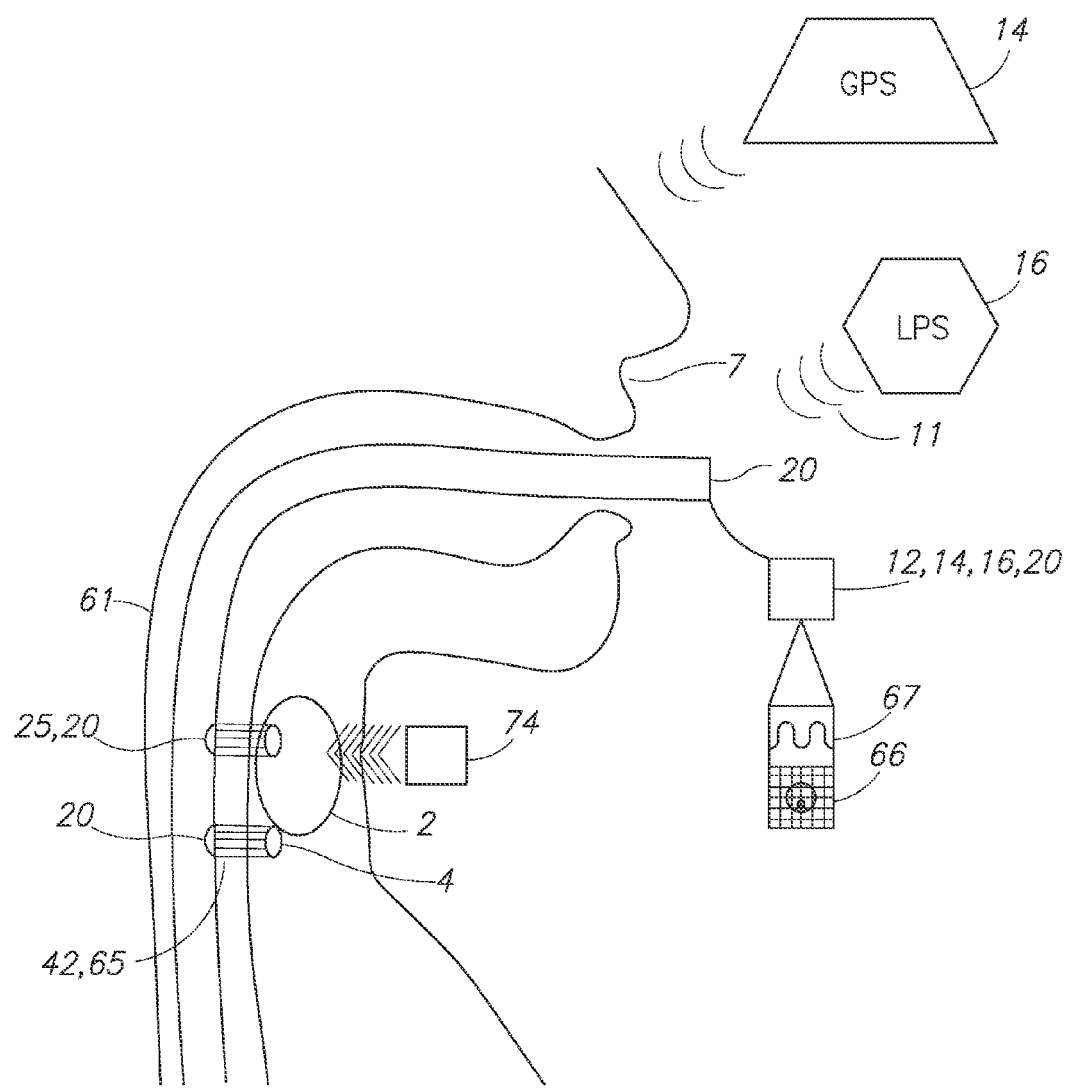
FIG. 5 depicts a sensor, detection or diagnostic or treatment assistance device that can be used in conjunction with or separate from other localizing devices or localizing methods. Sensors can be external or internal in nature as related to the body. The sensor can be put into position with methods that can include but are not restricted to being swallowed, inhaled, injected, placed onto, or put into or through the skin or mucosa or an orifice. In this depiction the sensor is a thermal sensor that can be positioned both in the skin and also in the esophagus to assist with the triangulation of the position of the abnormal parathyroid gland. The target organ can be interrogated before or after or while being excited by an energy method or source.

FIG. 5 depicts a sensor, detection or diagnostic or treatment assistance device 20 that can be used in conjunction with or separate from other localizing devices or methods using localizing devices 12, 14, 16. Sensors 20 can be external or internal in nature as related to the body. The sensor 20 can be put into position with methods that can include but are not restricted to being swallowed, inhaled, injected, placed onto, or put into or through the skin 60 or mucosa 6 or an orifice of the body. In this application, skin 60 and mucosa 6 may be used interchangeably since they are both coverings of the body 7 or body parts 7. In FIG. 5 the sensor 20 is a depiction of a thermal sensor that can be positioned both in or on the skin 60 and also on the mucosa 6 of the trachea (not depicted) or the esophagus 61 and the sensor 20 may measure a sensory output of the parathyroid 4 and or the thyroid 2, but can be used with other body parts 7 and may utilize data 42 to include but is not restricted to electromagnetic, kinetic or mechanical signals or outputs 65 that can include but are not restricted to heat, electromagnetic wavelengths, vibrations, sound, secretions, excretions, change in position to include but not restricted to flow or movements to include but not restricted to blood and urine flow, intrinsic and extrinsic solid or liquid or gel or gas within or about or associated with body organs 7. Such sensor 12 embodiments can include but is not restricted to a sensing device or method 12 for parathyroid 4 identification to include but not restricted to thermography, heat sensitivity and near infra-red, infra-red detection or imaging or a combination of imaging and detection where these methods can be used to identify and diagnose the location 66 of the abnormal parathyroid 4 gland which is more vascular and exudes more heat than other less vascular thyroid 2 and other body local tissue 7. This can be used for diagnosis or treatment or a combination of diagnosis and treatment to include but not restricted to the use of near infra-red, infrared other electromagnetic wavelength analysis. The sensor 20 can be combined with, or integrated with, a locator 12 and used to assist with the localization and also the characterization of the position of the abnormal parathyroid gland 4 in the coordinate system 30 when equipped with a locator 12. A sensor 20, locator 12, or marker 32 can include a radiation exposure sensor. A sensor 20, locator 12, or marker 32 may sense or emit radiation. These methods can assist with both triangulation or the positioning of the abnormal parathyroid gland 4 and can also assist with determining function and characterization of the parathyroid 4 and its local functional environment. Thus simultaneously providing a location 66 and a physiologic 67 status for a body part 7 which in some embodiments is the parathyroid 4 and thyroid but can be applied to other local and more distal body structures 7 such as body parts 7 to include but not restricted to nerves, vessels, organs 7 and coverings.

Figure 6:
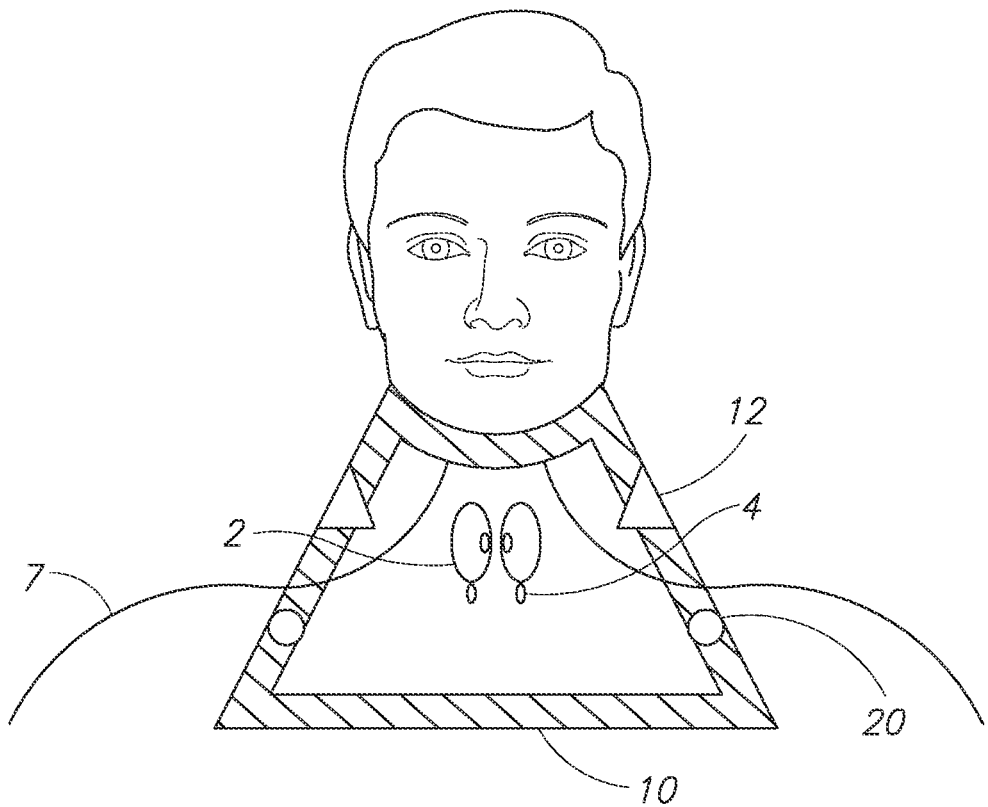
FIG. 6 depicts an example of a frame or fixation device and method that can be used to maintain or fix a location device or sensor relative to the body part or the target organ or structure or body.

FIG. 6 depicts an example of a frame 10 or fixation device 10 and method that can be used to maintain or fix the frame 10 and a location device 12 and/or sensor 20 relative to the body part 7 or the target organ or structure or body 7. The method may include affixing the frame 10 to a living body. One or more location devices 12 and/or one or more sensors 20 affixed to the frame may then be detected according to any of the methods disclosed herein to determine a position and/or orientation of a portion of the body engaging the frame. The location devices 12 and sensors 20 can be embodied as any of the markers, locators, locating devices, or sensors, disclosed herein.

FIGS. 1 through 6 illustrate methods for identifying and localizing and sensing bodily structures 7 which can be used, but are not restricted to use, in processing nuclear medicine images and radioactivity 9 information acquired and compared over one or more time intervals in order to compare separate images and radioactivity 9 using one or more isotopes. This method uses identified target organs 7 to align 1 body structures 7 and assess their two or three dimensional location 66 based on acquired data 42, such as based on a two dimensional projection with a modified or modulated or subtracted Nuclear medicine image. Specifically this technique can be useful and be applied to, but not restricted to, parathyroid gland 4 detection imaging.

The normal thyroid 2 activity 9 decreases its activity 9 over time. The abnormal parathyroid 4 activity 9 increases its activity 9 over time. Early imaging of the parathyroid 4 is masked by higher radioactivity 9 count rates in the thyroid 2. Over time the thyroid 2 activity 9 theoretically decreases to a level low enough that the parathyroid 4 activity 9 will become greater than the thyroid 2 activity 9. Although this event occurs in this manner in many patients, this phenomenon does not occur in a significant number of patients. In about 30 to 50% of patients the thyroid 2 and the parathyroid 4 activity 9 can be overlapping or the thyroid 2 radioactivity 9 does not reduce sufficiently to yield a confident diagnosis for a parathyroid 4 adenoma.

In order to increase the confidence of the abnormal parathyroid 4 diagnosis and improve the conspicuity between the thyroid 2 activity 9 and the parathyroid 4 activity 9, imaging methods can be applied to overcome the limitations of persistent thyroid 2 activity 9.

One method uses Tc-99 Sestamibi as the diagnostic isotope for generating radioactivity 9. A nuclear medicine camera device assigns regions of interest (ROI) or pixels to the body 7. This information is collected at different points 40 in time (a temporal data 42 set or temporal map). These data 42 sets can be compared. A Region of Interest (ROI) is assigned a value and depending on the increase or decrease in that ROI the pixel can include but not restricted to be amplified, remain the same, diminished or modulated by a mathematical model in relationship to but not restricted to the present, future or the past images or the adjacent pixels or data 42 sets.

One embodiment can include but is not restricted to a radioactivity 9 correction method where the thyroid 2 will increase in activity 9 after the first few seconds to minutes and this can then be used to create a region that is designated as thyroid 2. Over time the normal thyroid 2 radioactivity 9 will then diminish. One embodiment can include but is not restricted to a method where the removal of all radioactivity 9 in the thyroid 2 neck region that is diminishing at a given threshold rate or at a given time interval or period is assumed to be thyroid 2 activity 9. One embodiment can include but is not restricted to a method where all or most of the diminishing activity 9 can then be added or subtracted from the image in a manner to include but not restricted to all or a portion of the activity 9 in a manner to include but not restricted to the data 42 being altered using a mathematical model that modulates the data 42 by a method to include but not restricted to a linear or nonlinear or a variable or non-variable manner. In some embodiments the abnormal parathyroid 4 activity 9, which increases over time either in an absolute or relative manner relative to the thyroid 2 activity 9 can then be better imaged after deducing the thyroid 2 activity 9. One embodiment can include but is not restricted to a method where all increasing absolute or relative activity 9 can also be amplified after a specific target threshold time in conjunction with subtracting or reducing all diminishing activity 9, which is assumed in this model to be thyroid 2 activity 9. In this embodiment the amplification of increasing activity 9 the parathyroid 4 will become more conspicuous compared to the decreasing thyroid 2 activity 9 which will become less conspicuous. One embodiment can include but is not restricted to a method where the relative levels at which the values amplified or diminished can be adjusted or modulated upward or downward by filters that are absolute or relative and can have variable curves to include but are not restricted to non linear, linear or Gaussian or exponential curve filters or any combination of filters Amplification and reduction levels in some embodiments may range from 2 to 10 times the raw data 42 value but are not restricted to these ranges.

In some embodiments, washout can be used to facilitate detection of the parathyroid. Washout can include but is not restricted to a stabilization or a decrease in radioactivity in a target organ 7 that can include but is not restricted to the parathyroid 4 or thyroid gland 2. For the parathyroid 4 a substance can be administered to reduce radioactivity uptake to include but not restricted to non-radioactive labeled sestamibi, calcium, calcium channel blockers or sensipar (cinacalcet). After the administration of the washout substance the washout rate and imaging and activity can be measured in the parathyroid 4. The areas of washout can be compared to the areas of increasing uptake prior to administering of the washout substance. If an area of increasing uptake matches the pre-washout substance administration, then this helps confirm the probability that the structure that follows this pattern has a high probability of being a representation of the parathyroid gland 7. A final diagnosis of the location of the parathyroid adenoma may be based on multiple factors and can include the accumulation of isotopes to include but not restricted to Sestamibi Tc99m activity in the parathyroid relative to background and to the thyroid activity. Increasing the conspicuity between the parathyroid and the thyroid assists in this process. Other methods for diagnosing a parathyroid adenoma are based on location of the parathyroid. Changes in the expected outline of the thyroid or activity located asymmetric, atypically or eccentrically or aberrant relative to the thyroid can include but are not restricted to being located lateral or superior or inferior or posterior or anterior or medial or ectopically. A computer aided modeling program can be used to predict thyroid location and can include changes in the smooth outline of the thyroid, projection of the thyroid in an asymmetric or eccentric or atypically or aberrant position, or can be combined with another imaging modality to include but not restricted to CT, MRI, PET and PET-CT, PET_MR or ultrasound or thermography to predict and define whether the eccentric or asymmetric or atypically or aberrant activity is likely parathyroid activity. This same locator modeling can be applied to other body organs to include but not restricted to adrenal glands, thyroid nodules, bleeding sites and tumors and can utilize Sestamibi Tc 99m and isotopes other than Sestamibi Tc 99m.

Some embodiments can include, but are not restricted to, a localization method where the alignment 1 of the thyroid 2 and the parathyroid 4 can be improved by registering 1 body structures 7 that take up and transmit 50 the Tc Sestamibi, or some other detectability-enhancing substance, to include but not restricted to the radioactive 9 body 7 parts, to include but not restricted to one or more of salivary 5 glands, the heart 37, the liver 38, and external 8 active radioactive 9 markers 32. These body 7 structures are distributed at different locations 66 within the body 7 and have a three-dimensional relationship in the body 7. These localizing structures can be chosen to include but are not restricted to body 7 structures that do not significantly change their relative position in the body 7 during the course of the scan. Even though the localizing structures 7, 8 radioactivity 9 may vary during the scan, the absolute or relative radioactivity 9 is not the issue and it is the location 66 of the structure and of its activity 9 that is most pertinent to aligning 1 the body 7 parts using a method to include but not restricted to two dimensional (2-D) or three dimensional (3-D) modeling 24 or a combination of both 2-D and 3-D modeling 24. By aligning 1 these localizing structures a patient can thus move 22 around or even be removed from the scanner and the image can still be aligned 1 even if the patient moves 22 between scans. One embodiment can include but is not restricted to a method where the data 42 is realigned using a mathematical correction for positioning utilizing the expected 3-D location 66 which is then transmuted into a 2-D location 66 of the structures to compensate for misalignment 1 between scans. This process can be performed once or more than once to fine-tune or adjust the static target locations 66. This method can be combined with other methods that provide for image alignment 1 or re-alignment 1.

One embodiment can include but is not restricted to a method where the alignment 1 can be augmented using three-dimensional mathematical modeling 24 of either the target organs 7, to include but not restricted to the thyroid 2 and parathyroid 4 or the non-target organs 7 to include but not restricted to the thyroid 2 glands, the heart 37, and the liver 38 or active nuclear radioactive 9 markers 32.

Another embodiment can include but is not restricted to a method where the radioactivity 9 of the non-target organs 7 can be standardized and correctional computations performed based on an increase or decrease in radioactive activity 9 over time and then compare this increase or decrease in radioactivity 9 to but not restricted to the target organ 7 (e.g. thyroid 2 and parathyroid 4 glands).

Another method can use but is not restricted to the use of external 8 radioactive 9 markers 32, which can be standardized and the rate of decay measured and used to correct for target and non-target organ 7 corrections or location and activity 9.

Another method can use but is not restricted to the use of external 8 radioactive 9 markers 32, which can be used as localizing markers 32 by which alignment 1 can be augmented or achieved and can be combined with other alignment 1 methods to include but not restricted to alignment 1 of the target and non-target organ 7 corrections or location and activity 9.

One embodiment can include but is not restricted to a method where the radioactivity 9 is acquired in a continuous or discontinuous method or a combination of continuous or discontinuous.

One embodiment can include but is not restricted to a method where the radioactivity 9 correction method, the localization method or a combination of the radioactivity 9 correction method and the localization method and other currently utilized methods that can use and include but is not restricted to CT, MRI, Thermography or other imaging techniques One embodiment can include but is not restricted to a method where the localization is performed with electro-magnetic radiation to include but not restricted to near infra-red, infra-red, ultraviolet and thermographic imaging device. In one embodiment the patient can be repositioned on the table in the same position by using a method that includes but is not restricted to thermography, heat or near infra-red, infra-red imaging or a combination of the above.

In another embodiment the heat sensitive method for localization can be applied using a superimposed thermographic acquisition or image and the nuclear medicine radioactivity 9 image can be corrected using a method to include but not restricted to mathematical correction, filter correction, position correction.

In another embodiment the electro-magnetic sensitive method for localization can be applied using but not restricted to a superimposed thermographic acquisition or image and the nuclear medicine radioactivity 9 image can be corrected using a combination of methods to include but not restricted to mathematical correction, filter correction, position correction and the embodiment where the patient can be repositioned on the table in the same position by using a method that includes but is not restricted to thermography, heat or near infra-red, infra-red imaging or a combination of the above.

In another embodiment a heat sensitive method to include but not restricted to thermography or near infra-red, infra-red detection can be applied for localizing abnormal parathyroid 4 glands. Heat sensitive methods are based on the fact that pathological parathyroid 4 glands have a high blood flow rate and an increased metabolism that produces increased heat which can be detected by instruments that include but are not restricted to thermographic or near infra-red, infra-red sensitive detection devices. These thermographic or infra-red methods and detectors can be used alone or in combinations with other imaging detection or localizing devices to be used to include but not restricted to identify the location 66 of an abnormal dysfunctioning parathyroid 4 or thyroid 2 gland, assist in registration and alignment 1 of body 7 structure, treatment of abnormal thyroid 2 or parathyroid 4 structures or any combination of these organs 7 or techniques or methods.

In another embodiment a calcium detection method to include but not restricted to NMR, Functional magnetic resonance, or magnetic resonance imaging spectroscopy detection can be applied for localizing abnormal parathyroid 4 glands. The calcium sensitive methods are based on the fact that pathological parathyroid 4 glands have a high blood flow rate and an increased calcium detection or binding or metabolism that produces calcium localization which is absolute or relative to surrounding tissue which can be detected by instruments that include but are not restricted to NMR, Functional magnetic resonance, or magnetic resonance imaging spectroscopy detection sensitive detection devices. These NMR, Functional magnetic resonance, or magnetic resonance imaging spectroscopy detection methods and detectors can be used alone or in combinations with other imaging detection or localizing devices to be used to include but not restricted to identify the location 66 of an abnormal dysfunctioning parathyroid 4 or thyroid 2 gland, assist in registration and alignment 1 of body 7 structure, treatment of abnormal parathyroid 4 or thyroid 2 or structures or any combination of these organs 7 or techniques or methods.

One embodiment can include but is not restricted to a method where the localization and positioning of the patient is performed with a Global Positioning Satellite Tracking Device (GPS 14). The GPS 14 can be positioned onto the patient in one or more locations 66. In one embodiment the GPS 14 device can be affixed directly to the body 7 using various methods to include but not restricted to adhesive, tapes, elastic, cloth, can be injected or implanted and Velcro In another method the GPS 14 device can be affixed indirectly to the body 7 using a method to include but not restricted to a garment, a mask, a frame 10, a helmet, or an apparatus designed to mold to a body 7 part. The direct and the indirect methods can be used alone or in combinations.

One embodiment the GPS 14 device can be used but is not restricted assist in patient positioning. This method can be used to include but not restricted to assist radioactivity 9 and thermography correction and localization methods by more precisely superimposing the body 7 structures and providing for more accurate image correction. The GPS 14 can be used for correction methods and for localization method or a combination of the correction method and localization method. The GPS 14 method can be used with currently utilized methods for image creation and quantitative and qualitative methods that can include but not restricted to CT and PET or correct quantitation to include but not restricted to Gaussian, linear or exponential curve filters.

Local Positioning System/Locators/Device 16.

One embodiment can include but is not restricted to a method where the localization and positioning of the patient is performed with a Local Positioning Tracking Device (LPS 16).

A mobile or fixed coordinate 30 location device 12 replaces the in space satellites. The coordinate 30 location 66 similar to ones used in a satellite position is set by the position of the transmitter 12, 50 and or receiver 12,51.

An LPS 16 device calculates its position by precisely timing the signals sent by LPS 16 devices strategically placed around the target which can include but is not restricted to the patient being imaged. Each LPS 16 device continually or periodically, transmits 50 messages that include, the time the message was transmitted 50 and the precise positional information of the LPS 16 device that substitutes for the ephemeris-like behavior in a GPS 14 device. The LPS 16 receiver or receivers 12, 51 and transmitter or transmitter 12, 50, which are positioned relative to the target that can include but is not restricted to the patient's body 7 or a body 7 part of the patient uses the signals it receives to determine the transit time of each signal and computes the distance from each LPS 16 device. These distances along with the LPS 16 devices locations 66 are calculated using an algorithm to include but not restricted triangulation, trilateration, depending on which algorithm is used, to compute the position of the transmitter 12, 50 and receiver device 12, 51. The position to include but not restricted to the body 7 or body 7 part is then displayed on a display that can include but is not restricted to a body 7 profile, a schematic of the body 7, a moving map, a Cartesian map, a display with latitude and longitude and elevation, a display with cranial caudal and anterior-posterior position, The display can include but is not restricted to displaying animated information, an x-ray, CT, PET scan, Nuclear Medicine, Ultrasound, Photo Acoustic Imaging, Thermographic image and that image can display information to include but not restricted to anatomic information, physiologic 67 information, radioactivity 9, instrumentation information, human information to include but not restricted to receivers 12, 51 or transmitter 12, 50 on the hands, fingers, surgical tools and the information displayed can include but is not restricted to movement, speed, direction, and change in position.

In the some embodiment six LPS 16 devices are optimal but the number of LPS 16 devices can be more than or fewer than four LPS 16 transmission devices. Fewer than four LPS 16 devices can be used if the LPS 16 device knows its position to include but not restricted to 1-D, 2-d or 3-D or 4-D (temporal dimension included), which can include but is not restricted to a fixed receiver 12, 51 on or in the body 7 or body 7 part that serves as an absolute or relative position in reference to the body 7.

One embodiment, can include but is not restricted to determining a location 66 using a mathematical method such as lateralization using the LPD devices that can be on the body 7 in the body 7, external 8 to the body 7 or any combination of on the body 7 in the body 7, and external 8 to the body 7.

In one embodiment a method is used for correcting for the speed of light which is a large value to include but not restricted to a method using an atomic clock that is as accurate as can be manufactured. In another method a solution for correcting for clock error can include but are not restricted to using additional antenna or transmitter 12, 50 whose spheres or signals intersect to include but are not restricted to a control signal or sphere or surface or computational or constructed fixed coordinate 30 or coordinates 30.

In another embodiment, the receiver 12, 51 can be constructed to exceed standard bit speeds of 4,800 bit/sec and can use protocols that do not require large ranges but can focus on small areas. By not utilizing standard GPS 14 this would provide a method that was in compliance with US Government controls. Also by placing the transmitter 12, 50 below the ionosphere one of the major causes of delay can be bypassed.

Another embodiment can include but is not restricted to one or multiple LPS 16 devices. Another embodiment can include but is not restricted to one or multiple GPS 14 devices. Another embodiment can include but is not restricted to a combination of one or multiple LPS 16 and GPS 14 devices.

Another embodiment can include a method for correcting for error if a GPS 14 device is used. An error can occur secondary to delay in signal transmission through the ionosphere. More than one transmitting 50 frequency can be used to correct for ionosphere error by comparing capture rates for each frequency.

Another embodiment can include but is not restricted to using a more precise method called Carrier-Phase Enhancement (CPGPS), which correct for any incongruity between the phase and can use an additional clock using a method to include but not restricted to the L1 carrier wave which can correct for non-instantaneous imperfect correlation of transmitter 50-receiver 51 correlation.

Another embodiment can include a method for precision that can include but is not restricted to Relative Kinematic Positioning (RKP).

Another embodiment can include a method for precision that can include but is not restricted to using a clock that is not synchronized to Coordinated Universal Time (UTC), a method that is synchronized to GPS 14 time, a method that is independent of GPS 14 time and UTC (Non-UTC and non-GPS 14; independent coordinated time (ITC); International Atomic Time (TAT) or any combination of TAI, UTC and GPS 14 and ITC.

In one embodiment ITC can be a time that is set independent of all standards and is used only for the local LPS 16.

Another embodiment can include a method for precision that can include but is not restricted to knowing the precise distance between the transmitter 12, 50, receivers 12, 51 or a combination of transmitter 12, 50 and receivers. This precise distance can be determined using methods to include but not restricted to lasers, ultrasound, and electromagnetic measuring devices and other methods for measurement to include but not restricted to kinetic physical measuring techniques to include but not restricted to rulers.

Knowledge of the fixed distance between transmitter 12, 50, receivers or combination of transmitter 12, 50 and receivers 12, 51 can be used to set the clock or distance or precision of location 66 more precisely and can be used to eliminate or reduce errors to include but not restricted to the partial wavelength, wavelength off-set, time incongruence, mathematical assumptions or any combination of these errors.

Another embodiment to include but not restricted to synchronizing the receiver 51 and the transmitter 50 clocks using methods to include but not restricted to one or multiple wavelength sampling and correlation and comparing these wavelengths, tuning the clocks using a method to include but not restricted to using the known distance between the fixed receivers 12, 51 and transmitter 12, 50 to synchronize and correlate time and distance using one or multiple wavelengths, lasers, or other electromagnetic or non-electromagnetic measuring tools. Some embodiments may include but is not restricted to triple differencing which subtracts the receiver differences from Time A compared to that of Time B. In one embodiment the triple difference method can use three independent time pairs to solve for a receivers location 66 position.

In one embodiment a mobile or fixed LPS 16 can be positioned onto the patient in one or more locations 66. In one embodiment the LPS 16 device can be affixed directly to the body 7 using various methods to include but not restricted to adhesive, tapes, elastic, cloth and Velcro, In another method the GPS 14 device can be affixed indirectly to the body 7 using a method to include but not restricted to a garment, a mask, a helmet, or an apparatus designed to mold to a body 7 part. The direct and the indirect methods can be used alone or in combinations.

One embodiment the LPS 16 device can be used but is not restricted assist in patient positioning. This method can be used to include but not restricted to assist radioactivity 9 and thermography correction and localization methods by more precisely superimposing the body 7 structures and providing for more accurate image correction. The LPS 16 can be used for correction methods and for localization method or a combination of the correction method and localization method. The LPS 16 method can be used with currently utilized methods for image creation and quantitative and qualitative methods that can include but not restricted to CT and PET or correct quantization to include but not restricted to Gaussian, linear or exponential curve filters In another embodiment the methods for localization described above can be applied to an organ 7 or structures other than the parathyroid 4 or thyroid 2 and can include but is not restricted to the musculoskeletal system to include but not restricted to an ACL 70 graft placement, hardware 26 surgical placement of the 19 and surgery to other body 7 parts (not depicted) to include but not restricted to the kidney, heart 37, neural structures, glands, muscles, endocrine and neuro-endocrine tissue and tissue of ectodermal, endodermal and mesodermal origin and can include but is not restricted to normal and abnormal tissue to include tumors and non-tumor tissue and hyper-functioning and abnormal functioning tissue as well as normal functioning tissue and the techniques can be used for but not restricted to diagnosis and treatment.

In another embodiment the distance between the locators 12 and the receptors 20 can be calculated and incorporate using electromagnetic wavelength to include but not restricted to lasers and ultrasound.

Locator 12 and sensors 20 can be used to both transmit 50 and receive 51 signal or any combination of transmit 50 and receive 51.

In another embodiment the methods for image correction can be to an organ 7 or structures other than the parathyroid 4 or thyroid 2 and can include but is not restricted to the musculoskeletal system to include but not restricted to an ACL 70 graft placement, hardware 26 surgical placement of the knee 19 and surgery to other body 7 parts to include but not restricted to the kidney, heart 37, neural structures, glands, muscles, endocrine and neuro-endocrine tissue and tissue of ectodermal, endodermal and mesodermal origin and can include but is not restricted to normal and abnormal tissue to include tumors and non-tumor tissue and hyper-functioning and abnormal functioning tissue as well as normal functioning tissue and the techniques can be used for but not restricted to diagnosis and treatment. The hardware 26 can also contain transmission 50 and receiver 51 devices 20 to insure proper positioning in the body 7.

FIG. 5 depicts a sensor, detection or diagnostic or treatment assistance device 20 that can utilize include but is not restricted to an electro-magnetic, kinetic/mechanical or heat energy or any combinations of these energies as the energy being detected. These can include but are not restricted to electromagnetic, ionizing radiation, cold, heat, thermography, ultraviolet, infra-red, nuclear energy, ultrasound, sound, color, light, or movement. In one of the embodiments thermography can be used alone or in combination with one or more of the other energy detection or imaging devices 20 to identify, image or localize the parathyroid 4 and the thyroid 2.

Another embodiment can include using a sensing device 20 to identify the parathyroid 4 and thyroid 2 as well as other body parts 7. The sensor can include but is not restricted to a heat sensing parathyroid 4 identification method that is used to include but not restricted to mechanical and electromagnetic, photonic or optical readings more sensitive than the human eye can detect, thermography, heat sensitivity and near infra-red, infra-red detection or imaging or a combination of imaging and detection where these methods can be used to identify and diagnose the location 66 of the abnormal parathyroid 4 gland which is more vascular and exudes more heat than other less vascular thyroid 2. This can be used for diagnosis or treatment or a combination of diagnosis and treatment to include but not restricted to the use of near infra-red, infrared other electromagnetic wavelength analysis. An embodiment can include but is not restricted to a heat sensing parathyroid 4 identification method where the thyroid 2 tissue is suppressed and the vascularity reduced, which reduces the heat generated by the thyroid 2 and provides greater conspicuity between the parathyroid 4 and the thyroid 2 and allows the parathyroid 4 to be more easily detected. One method for reducing thyroid 2 activity 9 can include but is not restricted to propylthiouracil and methimazole (Tapazole) and thiourea and thiouracil and their derivatives or other thyroid 2 reducing or increasing agent that can include but are not restricted to antibodies or peptides or other organic or inorganic compounds or elements that can include but are not restricted to thyroid 2 stimulating hormone (TSH) or thyroid 2 releasing hormone (TRH) or agents that block TSH or TRH that can include but are not restricted to antibodies or immune mediated receptor or transmitted structures.

Another embodiment can include but is not restricted to a heat sensing parathyroid 4 identification method where the parathyroid 4 gland is hyper-stimulated using methods to include but not restricted to the administration of thiazide derivatives such as hydrochlorothiazide, or inorganic phosphates. The stimulation of the abnormal parathyroid 4 increases the heat production and blood flow of the parathyroid 4 gland thyroid and provides greater conspicuity between the parathyroid 4 and the thyroid 2 and allows the parathyroid 4 to be more easily detected.

One embodiment can include but is not restricted to a method where the standard Tc-99 Sestimibi is used in conjunction with a method where the thyroid 2 tissue is suppressed and the vascularity reduced which reduces the radioactive 9 uptake by the thyroid 2 or increases the uptake by the parathyroid 4. This can provide greater conspicuity between the parathyroid 4 and the thyroid 2 and allows the abnormal parathyroid 4 gland to be more easily detected. One method for reducing thyroid 2 activity 9 can include but is not restricted to propylthiouracil and methimazole (Tapazole) and thiourea and thiouracil and their derivatives or other thyroid 2 reducing or increasing agent that can include but are not restricted to antibodies or peptides or other organic or inorganic compounds or elements that can include but are not restricted to thyroid 2 stimulating hormone (TSH) or thyroid 2 releasing hormone (TRH) or agents that block TSH or TRH that can include but are not restricted to antibodies or immune mediated receptor or transmitted structures. This represents a new uses for these thyroid 2 suppression medications. This can be given prior to the Tc-99 Sestimibi injection and imaging.

Another embodiment can include but is not restricted to a method where the standard Tc-99 Sestimibi is used for detection and localization of the abnormal parathyroid 4 gland in conjunction with a method where the parathyroid 4 gland is hyper-stimulated. The stimulation of the abnormal parathyroid 4 increases the uptake and radioactivity 9 of the parathyroid 4 gland and provides greater conspicuity between the parathyroid 4 and the thyroid and allows the abnormal parathyroid 4 gland to be more easily detected. One method for hyper-stimulating the parathyroid 4 gland can include bit is not restricted to the administration of thiazide derivatives such as hydrochlorothiazide, or inorganic phosphates. In another embodiment parathyroid 4 modulating medications can be used to improve the treatment or identification or localization of the parathyroid 4 hormone and can include but are not restricted to sinacalcet, or a calcium channel agonist, a calcium channel antagonistic or an agonist or antagonist or the parathyroid 4 hormone or a variation on the Parathyroid 4 hormone (PTH) amino acid polypeptide to include but not include the active component of the parathyroid 4 hormone or a variation on the active component or the intact or non-intact parathyroid 4 hormone. These medications can be administered prior to during or after the imaging or treatment or procedure or combination of the procedures for both for the localization, diagnosis and/or treatment of parathyroid function and dysfunction or metabolism.

In some embodiments, detectability of the parathyroid 4 may be affected by administering an agent that alters the sensitivity of the sensing receptors in the parathyroid, such agents can include agents that act on calcium to include but not restricted to cinacalet and other elements or substances to include but not restricted to phosphous, magnesium, manganese and bisphosphonates to include but not restricted to alendronate, ibandronate, risedronate and zoledronic acid.

Detectability of the parathyroid may be affected by administering Sensipar (cinacalcet), which is a calcimimetic agent that increases the sensitivity of the calcium-sensing receptor to activation by extracellular calcium. Sensipar (cinacalcet) tablets contain the hydrochloride salt of cinacalcet. Its empirical formula is $C_{22}H_{22}F_3N.HCl$ with a molecular weight of 393.9 g/mol (hydrochloride salt) and 357.4 g/mol (free base). It has one chiral center having an R-absolute configuration. The R-enantiomer is the more potent enantiomer and has been shown to be responsible for pharmacodynamic activity.

One embodiment can include a method where the electromagnetic light spectrum is used to localize or stimulate or repress an organ 7 to include but not restricted to a parathyroid 4 gland or hyperplasia or an adenoma. A parathyroid 4 adenoma because of its unique cellular make-up and its blood supply is orange-red. Using a method where a specific wavelength in the electromagnetic spectrum is assigned to the parathyroid 4 to include but not restricted to a central range approximating 590 to 625 nm the reflection, translucence, transducing capacity or the absorption of this wavelength can be used to detect and localize a parathyroid 4 adenoma. Depending on the size and vascularity of the parathyroid 4 adenoma the specific wavelength may vary from this range. The method can be used to distinguish the parathyroid 4 tissue from the adjacent supportive tissue and the thyroid 2, which have a reflection, translucence, trans- ducing capacity or the absorption of this wavelength different from the parathyroid 4 adenoma. Other specific electromagnetic wavelengths can be used to identify other organs 7 or body 7 tissues. This method can include but is not restricted to photospectroscopy.

The target body 7 organ can be interrogated before or after or while being excited by an internal (not depicted) or external 8 energy method or source 74 to include but not restricted to electromagnetic, kinetic, heat, mechanical and ultrasound 25. In another embodiment the local tissue 7 can measured for heat absorption or heat sumps. In another embodiment the heat sumps or reduction in heat or the heat increases can be measured when an external or internal heating source is applied to the tissue being interegated for diagnostic or therapeutic purposes and the heat addition or reduction/dissipation is measured by a sensor or imaging method 20 to include but not restricted to x-ray, CT, PET scan, Nuclear Medicine, Ultrasound 25 (depicted), Thermographic imaging and in one embodiment is studying and relating to blood flow and heat sump calculations in the tissue body 7 region being interrogated.

FIG. 6 depicts on example of a frame 10 that can be used to maintain or fix a body part 7 relative to the body 7 or the target organ 7 or structure 12 or body 7. In some embodiments, the target organ 7 is the thyroid 2 and the parathyroid 4. In another embodiment frames or frame 10—like devices can be used to but are not excluded to being used to fix in place the radioactive 9 sources, the positioning devices, surgery and surgical assistance devices, and to fix a structure in a fixed or relatively fixed mechanical position and can include a garment, a mask, a helmet, or an apparatus designed to mold to a body 7 part to include but not restricted to caps, frames 10, bands, garments. An external 8 source can also be attached to the body 7 using methods of attachment to include but not restricted to adhesives, bandages, membranes, injections into the skin 60, sutures in the skin 60, bands and Velcro and straps, earrings, tattoos, and skin 60-piercings or internal and external 8 methods can be used and combined to include but not restricted to swallowed, inhaled, injected, place onto, into or through the skin 60 or mucosa 60 or an orifice. The marker or fixation 10 device can be composed of but is not restricted to a gel that can also serve as a marker for other imaging devices to include but not restricted to MRI, CT, thermography, or ultrasound.

Figure 7:
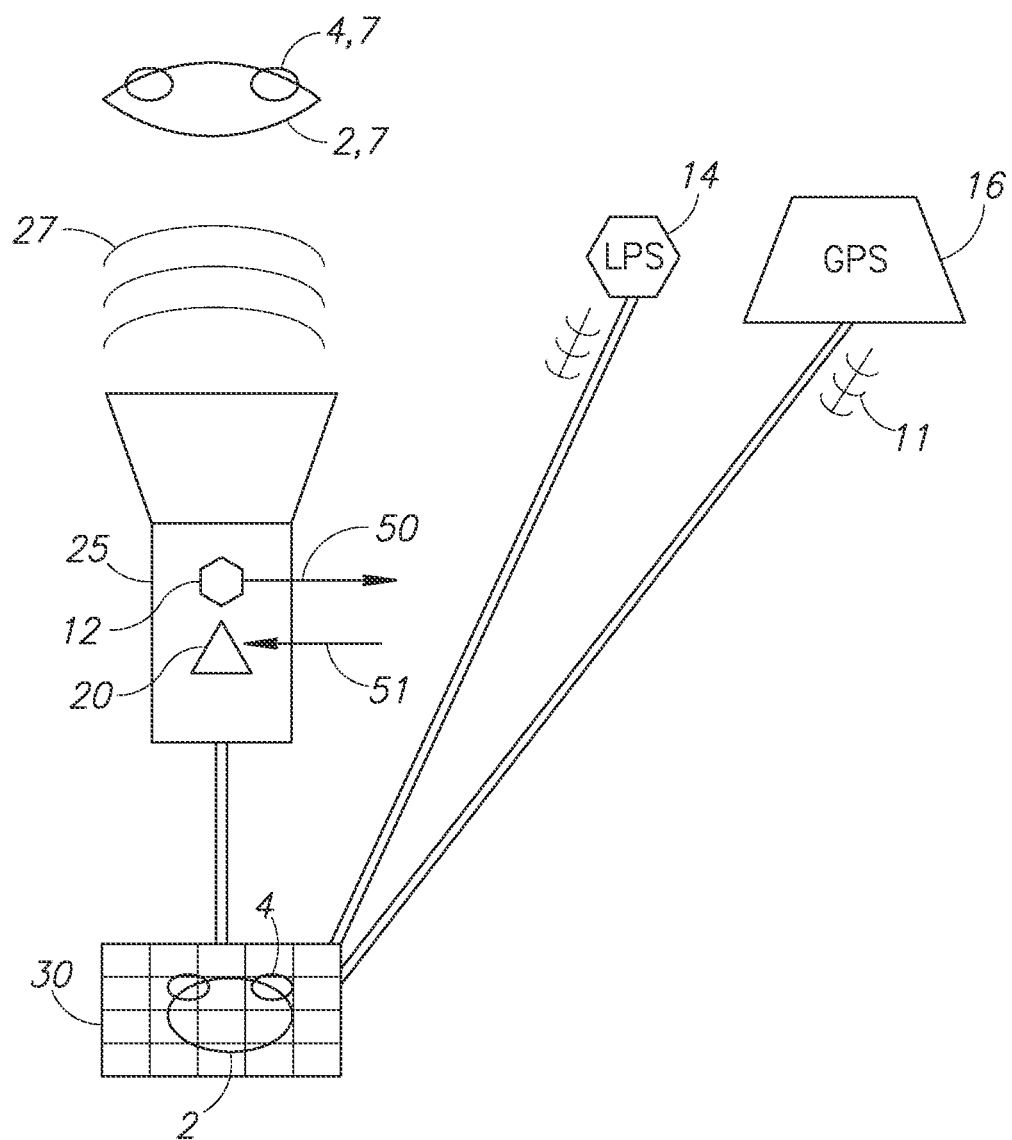
FIG. 7 is an ultrasound transducer, which incorporates a positioning or location/locator device that can transmit and receive signals that can be identified and recorded within the coordinates of the GPS or LPS or other coordinate system.

FIG. 7 is an imaging device which can be but is not restricted to an ultrasound transducer with a corresponding imaging technique 27, which incorporates a positioning device or locator 12 that can transmit 50 and receive 51 signals that can be identified and recorded within the coordinates 30 of the GPS 14 or LPS 16 coordinate 30 system or a sensing device 20. The transmitter 12, 50 and receiver 12, 51 that can be incorporated into the transducer can be measured in real-time and the outline of the thyroid 2 can be temporally mapped such that when the transducer is moved to outline a structure to include but not restricted to the thyroid 2 or parathyroid 4 then that outline of the body part 7 can be transmitted to the coordinate 30 system such that the body part 7 including but not restricted to the thyroid 2 and parathyroid 4 can be designated and located in space using the GPS 14 or LPS 16 coordinate 30 system.

Figure 8:
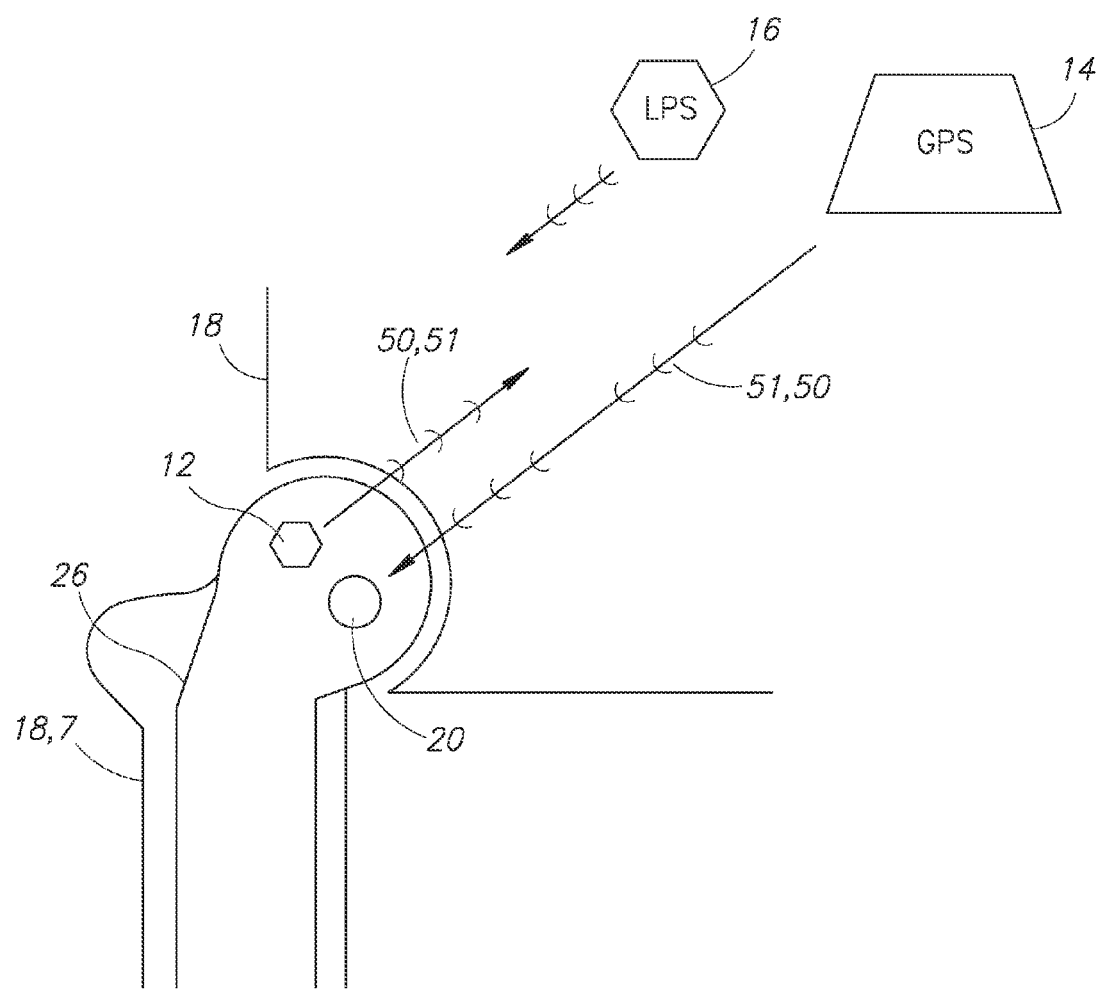
FIG. 8 is a prosthesis or medical hardware or implants or device that can incorporate one or more positioning or locator devices that can transmit and receive signals that can be identified and recorded and coordinated with the coordinates of the GPS or LPS coordinate system.

FIG. 8 is a prosthesis or medical hardware 26 or implant 26 or implanted device 26 into the body in this case a hip 18 that can be referred to as hardware 26 that can incorporate one or more positioning or locator 12 devices or sensor 20 that can transmit 50 and 12, 51 signals that can be identified and recorded and coordinated with the coordinates 30 of the GPS 14 or LPS 16 coordinate 30 system.

Figure 9:
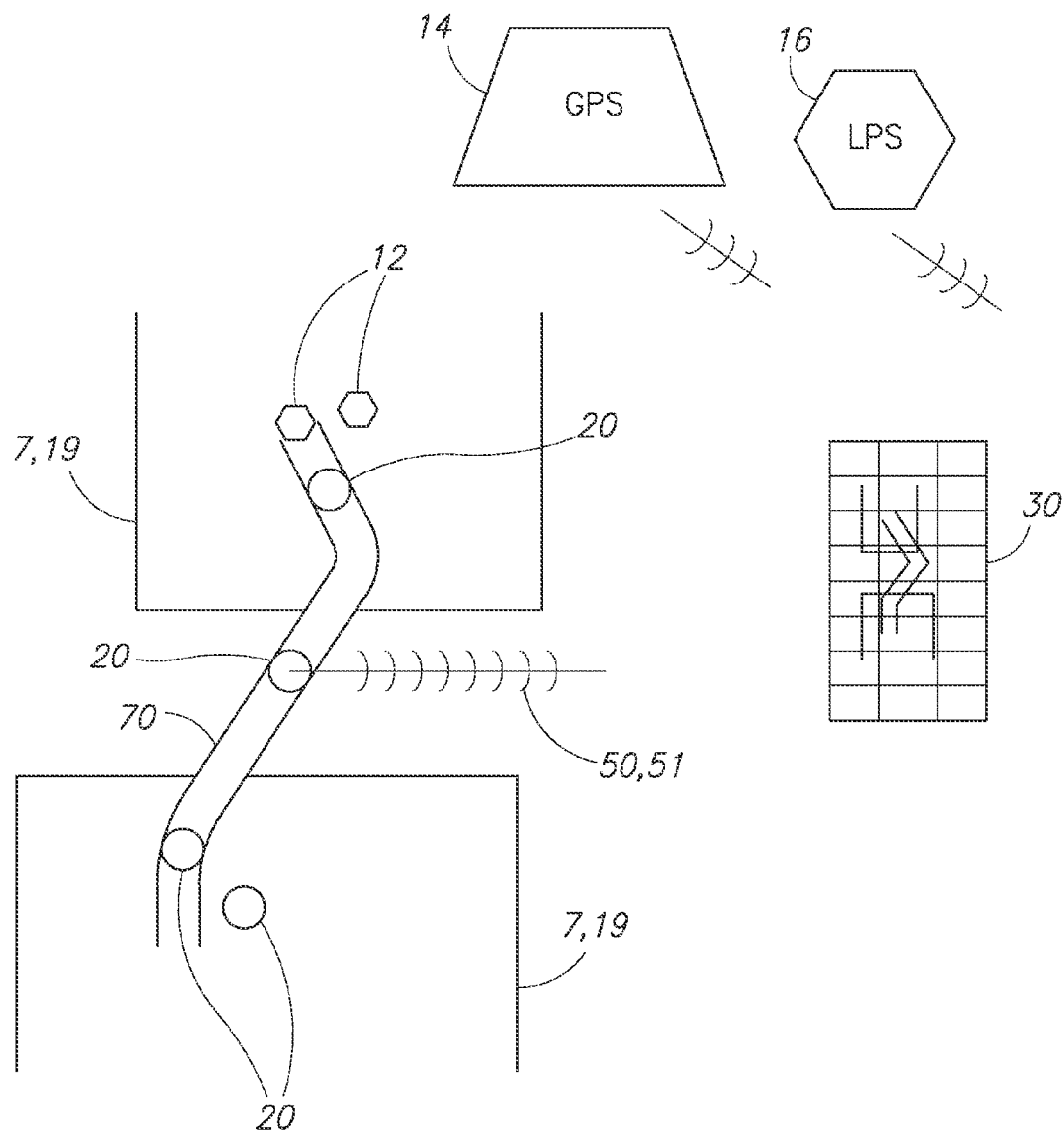
FIG. 9 is a prosthesis or medical hardware or implants or device that can incorporate one or more positioning or locator devices that can transmit and receive signals that can be identified and recorded and coordinated with the coordinates of the GPS or LPS 16 coordinate system and is viewed in relationship to a body part in this case a knee 19.

In FIG. 8 and FIG. 9 the transmitter 12, 50 and receiver 12, 51 of the locator 12 or sensor 20 can be incorporated into the hardware 26 and can be incorporated in the body part 7 and can be measured in real-time and their relationship can be measured and they can be temporally mapped such that when the hardware 26 is moved or positioned 22 or permanently placed in position it can be located and monitored and positioned relative to the remainder of the coordinates 30 and most importantly relative to other body 7 parts can be transmitted to the coordinate 30 system such that the hardware 26 and the body part 7 can be designated and located in space using the GPS 14 or LPS 16 coordinate 30 system. The application of these methods and embodiments can include but is not restricted to integrating these methods and processes and embodiments with or into a Computer Assisted/Aided Device (CAD) or platform or program or GPS 14 or LPS 16 and can be used with an imaging device 25 to include but not restricted to CT, MRI or Ultrasound. One of the challenges of prosthetic and hardware 26 stability is laxity and instability and movement. The sensors 20 and locator 12 can include positioning such that the prosthesis and the native body part 7 both contain one or more sensors 20 or a locators 12 such that when there is separation from the native body 7 structure this can be determined and measured for motion and separation and stability of the prosthesis or implant or hardware 26 or device 26 relative to the native body 7 part. Thus this embodiments use can include but is not restricted to plan, implant and monitor the implant or prosthesis or medical device 26 both prior to during and after the placement of the implant or prosthesis or medical device 26 relative to the body 7 part. This coordinate system can be used with GPS 14 and LPS 16 alone or in conjunction with other imaging methods including but not restricted to Computed Tomography (CT), Ultrasound (US), Magnetic Resonance Imaging (MRI), Thermography, or other imaging and/or positioning techniques.

An implantable device to which one or more sensors 20, locators 12, and markers 32 can be affixed to or implanted can include but is not restricted to a prostheses, a delivery device, a locator, a transmitter, a receiver, a sensing device, hardware to include but not restricted to medical hardware, screws, nails, rods, plates, imaging modules or apparatuses, parts of or complete artificial joints, organs, muscles, ligaments, tendons and other body part replacements, native and non-native, xenograft and allograft and homograft, identical and non identical donor material or body part, machines, sensors, flow devices, and electromagnetic and kinetic and heat and ultrasound and mechanical energy devices, endoscopes, transducers and treatment apparatuses. One or more locators can be positioned or placed inside or outside of the body and relative or absolute measurements can be obtained to determine the relationship of one locator relative to the other one or more locators and these measurements can include but are not restricted to distance, angulation, orientation, The locators can be associated with but not restricted to one or more probes or scalpels that can be associated with or have affixed or incorporate the one or more than one first locators that can but is not restricted to contain a compass, altimeter, accelerometer or protractor, ruler or other measuring device that can be digital or analog or mechanical in nature and can inform the user of measurements that can include but are not restricted to axies, distance, angulation, or orientation of the one or more than one locators or probe or scalpel and can be related to a body part or the one or more than one second location or locators.

In one preferred embodiment, the body part can be the knee and the implanted device can be an ACL graft. The graft can contain one or more locators which in the preferred embodiment can be at the opposite ends of a portion of the graft. Additional locators can be positioned on or near the tibia and fibula where the graft tunnels are to be drilled with a surgical instrument to include a bone drill. The drill or drill bit can include locators or sensors that can include but is not restricted to contain a compass, altimeter, accelerometer or protractor, ruler or other measuring device that can be digital or analog or mechanical in nature and can inform the user of measurements that can include but are not restricted to axies, distance, anglulation, or orientation of the one or more than one locators or probe or scalpel that can relate the graft to the body parts to include the tibia and fibula bone. The information from the locators of the graft or locators of or near the tibia and fibula or the surgical instruments or probes can communicate to a computer which can include but is not restricted to a CAD program or a 2-D or 3-D map of the graft and bones body parts being surgically repaired. Feedback from the analysis devices and computers or the locators can then be analyzed and the measurements that can include but are not restricted to the axies, distance, anglulation, or orientation can be determined and corrected such that the drill bit and the subsequent tunnels for the graft in the tibia and fibula can be determined and the graft can be placed in its proper orientation relative to the tibia and fibula. This same method or system can be used for other body parts. This method and system can be combined other imaging methods and can be combined with or performed by robotic surgery.

FIG. 9 is a prosthesis or medical hardware 26 or implants or device 26 that can incorporate one or more positioning or locator devices 12 or sensors 20 that can transmit 50 and receive 51 signals that can be identified and recorded and coordinated with the coordinates 30, 66 of the GPS 14 or LPS 16 coordinate system 30 or a sensory feedback units and is viewed in relationship to a body part 7 in this case a knee 19. FIG. 9 is a depiction of a knee 19 with a locator 12 that can position an ACL graft 70 or Knee 19 prosthesis 26 in the correct position and angle in the bones of the knee 19 to include the femur tibia and fibula. The ACL 70 graft can also contain a sensor 20 that can monitor the integrity of the ACL 70 in real-time and measure stresses on the ACL 70 and can measure integrity of the ACL graft 70 prior, during and after implantation. In this depiction the sensor 20 can include but are not restricted to measure tensile strength, stretch, thickness, heat, blood flow, specific blood particles such as red and white blood cells and position relative to other locators 12 implanted in the body 7 part which in this embodiment include the femur and tibia. This same or similar methods and devices and applications can be applied to other body parts 7 or implants/hardware 26.

Figure 10:
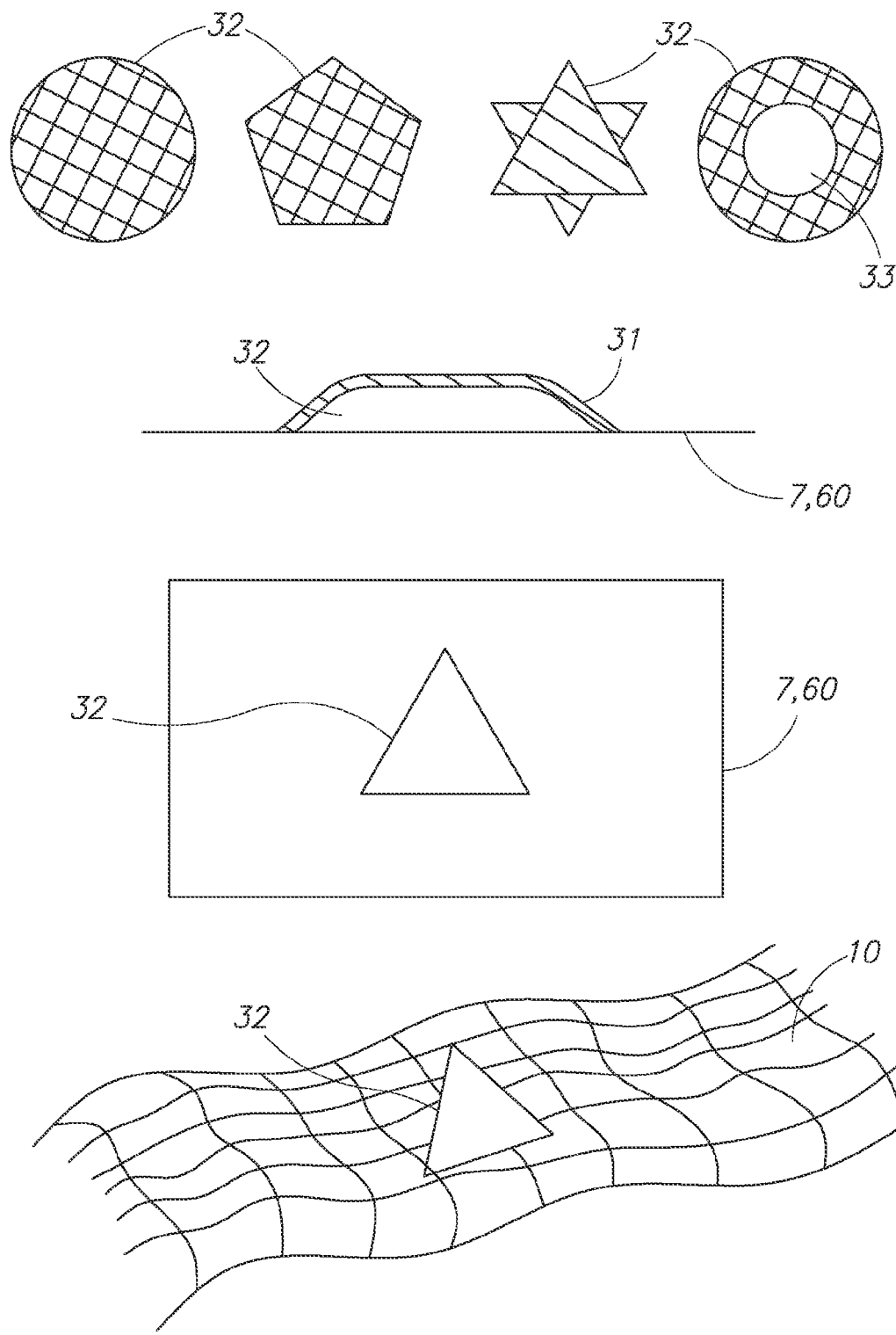
In FIG. 10, is an elastomeric gel marker of variable thicknesses and shapes including an annular marker with an area that can serve as a conduit through which a needle or object can be passed.

FIG. 10 depicts an elastomeric gel MRI marker that utilizes a block copolymer with lipophillic, lipid, oil or fat-like material and a hydrophillic or water-like material and elastomeric gel marker which can include and be constricted to include variable thicknesses and shapes including an annular marker with an area that can serve as a conduit 33 through which a needle or object can be passed.

Although these gels can be manufactured with all possible combinations of polymers depending on the T1 and T2 weighted imaging characteristics desired, some embodiments can employ a triblock copolymer composed of 25 to 75% lipophillic, fatty materials or oils but can include percentages of lipophillic, oil or fat material that are less than 25% fatty materials or oils or greater than 75% fatty materials or oils and can include all combinations of oil and fatty materials and water or hydrophillic materials. In the current embodiment the gel can include but is not restricted to be encapsulated fully or partially with a membrane or coating that can include but is not restricted to a firm or flexible or plastic or wax covering. The gel markers 32 can be produced with no membrane or the gel marker can have no coating or membrane 31 that can include but is not restricted to a plastic-like material, cloth material, or other organic or inorganic materials.

The gel markers 32 can be attached, associated or incorporated to a rigid or flexible frame 10 that can but is not restricted to conforming to a body 7 part.

The gel markers 32 can be tacky or not tacky. The gel markers 32 can include but are not restricted to include adhesives, velcro or other methods to fasten the marker to the body 7. One embodiment can include a gel marker that is attached, associated or incorporated to a rigid or flexible frame 10 or a material that can fix the marker to one or more body 7 parts and is a material that can be but is not restricted to a stretchable material that is made of an elastomeric gel, a cloth-like material, a stretchable cloth material such as but not restricted to COBAN©, a plastic or a fiber optic or a silicon based material or an organic or synthetic material.

Figure 11:
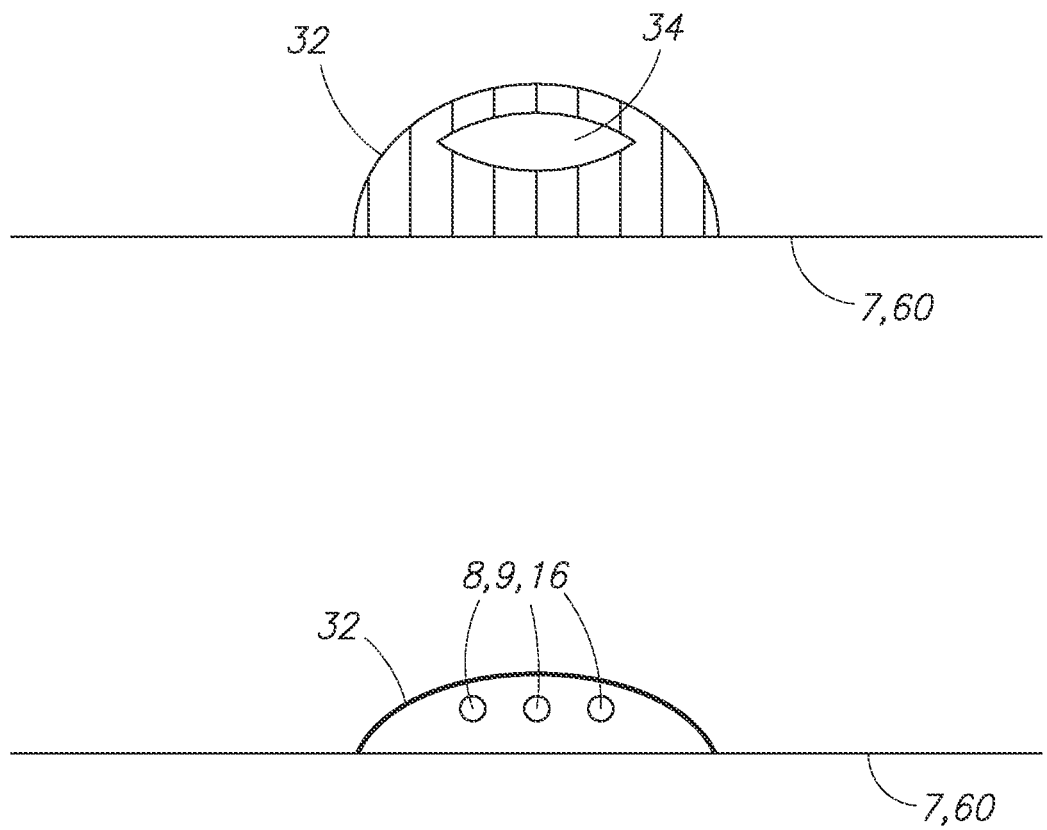
In FIG. 11, is a gel markers that can include but are not restricted to include a reservoir for radioactivity, or have a sensor device integrated into the gel and can include adhesives and fastening substances or a frame (not depicted) and can be used with and serve as markers for other imaging methods such as MRI and CT and ultrasound.

FIG. 11 depicts a gel markers 32 that can be solid or hollow and can include but are not restricted to include a reservoir 34 and/or a conduit and can be filled prior to, during or after the manufacturing or the imaging procedure. The gel marker can contain or be incorporated into or associated with a sensor or a locator that can include but is not restricted to a computer chip, a transmitter 50 or receiver 51 locator 12, radioactive 9 material, a crystal, or an organic or non-organic material that can be used as but not restricted to a sensor or locator that can detect, or convert, heat, kinetic, electromagnetic, ultrasound, odors, visible, auditory, gustatorytaste and sensorytouch signals input into an output that can be converted to but not restricted to a quantified or qualified signal to be used to assess input or used for another output.

FIGS. 10 and 11 depict the gel markers 32 can contain or incorporate one or more than one CT and X-ray dense materials, that can include but are not restricted to ferromagnetic and non-ferromagnetic materials that can include but are not restricted to radioactive 9 materials, gadolinium, iodine, lead, iron, copper, proteins, waxes, water, gas, vacuums and oils as well as other solids and liquids and gases.

The gel markers 32 can contain or incorporate one or more than one MR hypointense, isointense or hyperintense materials, that can include ferro-magnetic and non-ferro-magnetic materials that can include but are not restricted to radioactive 9 materials, gadolinium, iodine, lead, iron, copper, proteins, waxes, water, oxygen and carbon dioxide and nitrous oxide gas, vacuums and oils as well as other solids and liquids and gases.

The gel markers 32 can contain or incorporate one or more than one Ultrasound highly reflective or poorly reflective or hyperechoic, isoechoic or hyporechoic materials, that can include but are not restricted to radioactive 9 materials, gadolinium, iodine, lead, iron, copper, proteins, waxes, water, oxygen and carbon dioxide and nitrous oxide gas, vacuums and oils as well as other solids and liquids and gases.

The gel markers 32 can contain or incorporate one or more than one radioactive 9 materials or radioactive absorbing or blocking materials that can include can include radioactive 9-magnetic and non-radioactive 9 materials that can include but are not restricted to radioactive 9 technecium, iodine, and can include but are not restricted to other materials such as gadolinium, iodine, lead, iron, copper, proteins, waxes, water, oxygen and carbon dioxide and nitrous oxide gas, vacuums and oils as well as other solids and liquids and gases.

The gel markers 32 can contain or incorporate one or more than one thermophillic or thermophobic or thermoabsorbtive materials, that can include but are not restricted to radioactive 9 materials, asbestos, zeolite, fiberglass, gadolinium, iodine, lead, iron, copper, proteins, waxes, water, oxygen and carbon dioxide and nitrous oxide gas, vacuums and oils as well as other solids and liquids and gases.

The gel markers 32 can contain or incorporate one or more materials 16 that can include one or more solid or liquid or gel or gas materials that can include and can utilize electromagnetic absorbing or reflecting materials that can be specifically used for but not restricted to visible wavelength or ultraviolet or infrared wavelength materials that can include but are not restricted to radioactive 9 materials, asbestos, zeolite, fiberglass, gadolinium, iodine, lead, iron, copper, proteins, waxes, water, oxygen and carbon dioxide and nitrous oxide gas, vacuums and oils as well as other solids and liquids and gases.

The gel markers 32 can be cut or created or formed or shaped to include different geometric configurations to include but not restricted to ellipse, circle, rectangle, square or triangles and polygons and variable thicknesses to include but not restricted to one embodiment of 1 to 10 mm but can be greater or less than 1 to 10 mm. In some embodiments, the shape will be a shape that is not confused with anatomic shaped objects to include but not restricted to acute and obtuse angled structures and perfect circular objects. Markers 32 can be annular or non-annular. The markers 32 can include but not restricted to conformation to the body, or being thin enough yet still definable enough to be identified as a marker 32. The markers 32 can contain a central area void of gel that can serve as conduit to include but not restricted to needle placement for biopsies and for the passage of objects to include solids and liquids and gels and gases and these solid objects can be placed onto, into or through the skin 60 or adventitia or fascia or body 7 part.

T1 weighted compounds for this application are considered and include but are not restricted to fatty acids, fats and oil. T2 weighted compounds for this application are considered and include but are not restricted to water and hydrophillic compounds. As a reference using a 'true' spin echo sequence a T1 or fat or oil compound will be hyperintense or 'bright' on T1 with a TR of 500 and a TE of 12 and a T2 or water or hydrophillic compound will be hyperintense or 'bright' on T2 with a TR of 3000 and a TE of 80.

In some embodiments the marker 32 includes a first material having a hyperintense T1 value for a repetition time (TR) of 400 TO 600 and an echo time (TE) of 8 TO 14 and a second material having a hyperintense T2 value for a TR of 2500 TO 4000 and an echo time (TE) of 70 TO 110 using a 1.5 Tesla magnet.

MRI utilizes many techniques and physical properties of substances for imaging and for physiologic identification and this is defined and determined by subjecting the substance to different MR sequences. Two of the most common sequences or mechanisms for defining a substance are T-1 weighting and T-2 weighting. In general a T-1 weighted sequence results in body fat and can include but is not restricted to human subcutaneous fat, a non human fat, or oil-like or lipophilic substance appearing bright or more intense than human water to include but not restricted to Cerebrospinal fluid (CSF), water or hydrophilic substance.

Whereas, in general a T-2 weighted sequence results in human water to include but not restricted to Cerebrospinal fluid (CSF), a water or hydrophilic substance appearing bright or more intense than body fat and can include but is not restricted to human subcutaneous fat, fat or oil-like or lipophilic substance.

T-1 sequences utilize Spin-Lattice relaxation time. Spin-lattice relaxation is the mechanism by which the z component of the magnetization vector comes into thermodynamic equilibrium with its surroundings (the "lattice") in nuclear magnetic resonance (NMR) and magnetic resonance imaging (MRI). It is characterized by the spin-lattice relaxation time, a time constant known as $T_1$. It is named in contrast to $T_2$, the spin-spin echo relaxation time. The spin spin relaxation is the mechanism by which $M_{xy}$, the transverse component of the magnetization vector, exponentially decays towards its equilibrium value of zero, in nuclear magnetic resonance (NMR) and magnetic resonance imaging (MRI). It is characterized by the spin-spin relaxation time, known as $T_2$, a time constant characterizing the signal decay. It is named in contrast to $T_1$, the spin-lattice relaxation time. It is the time it takes for the magnetic resonance signal to reach 37% (1/e) of its initial value after its generation by tipping the longitudinal magnetization towards the magnetic transverse plane. $T_2$ relaxation generally proceeds more rapidly than $T_1$ recovery, and different samples and different biological tissues have different $T_2$. For example, fluids have the longest $T_2$s (in the order of seconds for protons), and water based tissues are in the 40-200 ms range, while fat based tissues are in the 10-100 ms range. Amorphous solids have $T_2$s in the range of milliseconds, while the transverse magnetization of crystalline samples decays in around 120 ms. $T_2$-weighted scans are another basic type. Like the $T_1$-weighted scan, fat is differentiated from water, but in this case fat shows darker, and water lighter. For example, in the case of cerebral and spinal study, the CSF (cerebrospinal fluid) will be brighter or lighter or more intense in $T_2$-weighted images. These scans are therefore particularly well suited to imaging edema, with long $T_E$ and long $T_R$ times.

MRI sequences that can be viewed using the elastomeric marker 32 can include but are not restricted to T-1 spin echo, T-2 spin echo, Gradient echo, turbo spin echo sequences, spectroscopy and inversion recovery sequences including fluid attenuated inversion recovery (FLAIR) and Short T-1 Inversion Recovery (STIR) imaging.

Various embodiments of the gel marker can include but are not restricted to variable combinations of T1 and T2 weighted materials. These combinations can be innate to the materials composing the gels and can include hydrophillic to include but not restricted to water abundant and can be lipophillic materials to include but not restricted to oil and fat abundant materials; or the materials can be interlaced or embedded into the gel to include but not restricted to being located within layers of the gel or can be separate from the gel to include but not restricted to a reservoir 34.

In some embodiments the shape has a configuration such that it is not a natural biologic structure and can include structures such as triangles, squares, circles, ellipses, pentagons, and other polygons, especially ones that have acute and obtuse angles and one or more non-anatomic angles. In some embodiments, the elastomeric gel MRI marker may have three unique and important characteristics that when combined produce an excellent MRI marker. First, the marker may be composed of an admixture of fatty oils (T1 shortening) and water elements (T2 shortening) that coexist. Second, the marker may be appropriately sized to the anatomy being interrogated. Third, because the material is an elastomeric gel it may be configured to readily conform to superficial structures without significant anatomic compression or distortion. The gel MRI marker may provide reliable visualization on a plurality of appropriate sequences, have an absence of artifacts, have a variety of sizes and shapes appropriate for the multiple anatomic sites and the various application being investigated, impose minimal to no distortion of the local anatomy, have the ability to conform to the contours of the local anatomy, have a nonanatomic shape so it will not be confused with biological structures, be easy to use and adhere to skin 60, be biologically safe and non-toxic with MRI use, preferably not use a liquid which can spill, be inexpensive to produce, and be highly detectable multiple non-visual imaging modalities to include but not restricted to MR, CT and Ultrasound.

The elastomeric markers 32 can have both T1 and T2 characteristics. The T1 characteristics can vary greatly. The contrast resolution between T1 and T2, or fat containing and water containing or lipophilic and hydrophilic tissues can be differentiated in similar organ's tissue, as is the case but not restricted to the difference between scalp fat and brain white matter, grey matter and cerebrospinal fluid (CSF). On the T1 sequence the signal intensity on a T1 weighted sequence is greatest within the scalp fat followed by the white matter. The grey matter is less intense than the white matter but more intense than the CSF. On T2 weighted sequences the CSF is most intense followed grey matter, then white matter then scalp fat in decreasing intensity. The MRI marker 32 can be constricted to be generic or specific to the tissue to which it lies adjacent. In one embodiment, if the marker 32 is adjacent to the scalp fat it will need to be distinguishable from scalp fat and the skin on both T1 and T2 sequences. If the marker 32 is adjacent to the CSF or a water-containing cyst in the scalp it will need to be distinguishable from the CSF or the water-containing cyst of the scalp, therefore the optimal T1 and T2 characteristics of the marker 32 can and may even need to or at least benefit from varying from a single generic one-fits-all marker 32. It is recognized that a generic marker 32 can be beneficial in many cases but not in many or in all cases. Therefore the marker 32 can vary widely in its T1 and T2 characteristics and still be effective. Therefore specific and optimal marker 32 T1 and T2 characteristics vary depending on the adjacent tissue and secondarily on the sequences being utilized and the primary principal is that the marker 32 can be distinguished on T1 and T2 weighted sequences and their derivative sequences to include but not restricted to spin echo, STIR, FLAIR, Diffusion, turbo-spin echo, and gradient echo and even flow sequences. In this embodiment most if not all sequences can be derived from T1 and T2 weighted sequences.

The marker 32 if used in x-ray and x-ray related imaging to include but not restricted to CT will need to vary in density relative to the absorptive property of the x-ray beam that is utilized and can be dependent upon but is not restricted to the KV (kilovolt) and Ma (milliamps) that are more typically used in these forms of x-ray imaging. The marker 32s density can be created by but not restricted to the density of the gel or the gel can contain ferromagnetic or non-ferromagnetic particles. In one of the preferred embodiments that contains particles, the particles can include but are not restricted to organic or inorganic materials, to include but not restricted to gels, plastics, elements that are ferromagnetic such as iron and nickel or cobalt or can be paramagnetic such as barium calcium, aluminum, magnesium and platinum or can be non-ferromagnetic such as or non-such as copper, lead, and silver.

If the marker 32 is used in nuclear medicine then its absorption of nuclear energy and the particles and energy released by differing forms of decay need to be considered and include but are not restricted to alpha, beta and gamma radiation. If the marker 32 is used in ultrasound then the acoustic properties need to be considered and include but are not restricted to altering the acoustic signal using solids, liquids, gels or gases or any combination or mixture of these structures. The tendency to conduct or induce a current needs to also be considered if the marker 32 is to be used in MR and can include but is not restricted to iron and needs to consider the effect of RF on the materials being used to prevent heating or the induction of currents.

Depending on the materials used then the shape of the marker 32 may be pertinent and can include but is not restricted to circles and spirals especially if these are repeating or overlapping in structure. In one embodiment a gel marker 32 can be impregnated with particles that are weakly paramagnet or non Ferro-magnetic or paramagnetic and weakly Radiofrequency (RF) reactive such as but not restricted to plastics and elements such as Barium or gadolinium. The particle sizes can vary and in the embodiment are in the Pico-meter to nanometer to micrometer size.

For the purpose of this application the terms activity and intensity may be used interchangeably and can refer to data derived from the living creature or target or can be processed data from a computer or imaging or collecting or display device.

Variations in the chemical quantitative composition of the marker 32, which are known to the MR interpreter, can be used as standards to assess chemical composition of body structures using various known standards. This can be applied to body composition and physiology and health to include but not restricted to bone marrow composition, fatty and fibrotic liver, osteoporosis, diabetes and pancreatic fatty replacement, distinguishing adenomas form aggressive tumors, general body fat calculations, metabolic replacement diseases and tumors.

In one embodiment a series of marker 32 standards can be place on or near the surface of the living creatures body which can include but is not restricted to the marker 32s neatly affixed within a housing or frame or structure. The standards can include one or more than one standard. In one embodiment the optimal number of standards can include but is not restricted to be an odd number of standards with one or more standards being in the normal range and one or more standards lying outside of the normal range for that specific organ. The organ can include but is not restricted to include the liver, the bone marrow, the pancreas. In the case of the liver the standards the first substance can be composed of a lipophilic or fat and the second substance or the more than the second substance being a non-fat material preferably but not restricted to a water or hydrophilic substance. The percentage of the first and the not-first second substance can be varied to simulate normal and abnormal relationships or ratio of fat and non-fat substances. The same principles can be applies to other organs including but not restricted to the pancreas. For other organs such as bone there can be fat and one or more than one non-fat substance which in some embodiments the more than one non-fat substance can include but is not restricted to calcium-hydroxyapatite and water based substances to simulate the bone structure. In some embodiments these substances can but are not restricted to be combined to simulate normal bone at variable ages, to simulate changes in the normal architecture of bone crystals to include but not restricted to normal bones, osteopenic and osteoporotic bones and bones that are more dense than normal and these can include but are not restricted to include both the density and the architecture of the bones, and the marrow and fact content of these bones.

Although in some embodiments these standards will be used with MRI these standards are not restricted to MR and can be used with CT and ultrasound and nuclear medicine. Although in some embodiments these standards will be elastomeric or gel compounds, these marker 32s are not restricted to elastomeric compounds and can include non-elastomeric and non gel substances such as other solids and liquids and gases. Variations in the chemical quantitative composition of the marker, which are known to the MR interpreter, can be used as standards to assess chemical composition of body structures using various known standards. This can be applied to body composition and physiology and health to include but not restricted to bone marrow composition, fatty and fibrotic liver, osteoporosis, diabetes and pancreatic fatty replacement, distinguishing adenomas form aggressive tumors, general body fat calculations, metabolic replacement diseases and tumors.

The application of these methods and embodiments can include but is not restricted to integrating these methods and processes and embodiments with or into treatment of parathyroid 4 gland dysfunction and function and other body part 7 functions and dysfunctions. Surgical and non-surgical and robotic approaches to parathyroid 4 and other body part 7 functions and dysfunctions treatment can benefit from precise localization of the abnormal parathyroid gland 4 and localization techniques described in this patent can be combined with surgical and invasive, minimally invasive, tightly targeted minimally invasive and non-invasive treatment techniques to include but not restricted to energetic or mechanical/kinetic, or biologic that can include but is not restricted to Radiofrequency ablation (RF) and microwave (MW) and laser (L), Cryotherapy (CryT), High Intensity Focused Ultrasound (HIFU), Radioactive 9 Therapy (Brachytherapy: BrT), Irreversible, Electroporation (IRE), Electrical Current Therapies, Electrocautery, Magnetic Resonance (MR), Ultrasound, (US), Thermal energies both heat and cold and mechanical or kinetic energies and with adjuvant combinations that can include but are not restricted to medication delivery, Medication packets, blood flow reduction, Chemical and Medication Ablation, Activation and Deactivation and Modulation Therapy, Adhesives and Glues and Molecular Crystal and Lattice therapies, Target Tissue Delivery Device Therapies, Peptide and Biological Conversion Therapies, MR and RF and Magnetic External 8 Heating Therapies, Hyperthermia with Adjuvant Therapy, Hypothermia with Adjuvant Therapy, Local protective therapy in the Vicinity of the Target Organ 7 Therapy, Suction and Expansion Therapy, Positive Pressure and Expansion Therapy, Mechanical Ablation Therapy and Combinations and biologic and nonbiological procedures that can include immune suppressive, repressive or advuvant, antibody elemental and chemical compounds to include but not restricted to calcium or magnesium barium, strontium, barium, and beryllium, fluorine chlorine bromine, astatine, iodine, oxygen, nitrous oxide or other inhaled or ingested or vascular injected compounds that alter metabolism, PTH 4 hormone or variations on the hormone or their repressors or stimulators, thyroid 2 hormone or their repressors or stimulators.

These methods can be combined with other methods that provide for image alignment 1 or re-alignment 1, including but not restricted to Computed Tomography (CT), Ultrasound (US), Magnetic Resonance Imaging (MRI), Thermography, or other imaging and/or positioning techniques.

The methods described above can include but are not restricted to the parathyroid 4, thyroid 2 and can be used for other body 7 parts. The methods and uses and devices described in this embodiment can be used on living creatures to include but not restricted to humans.

For purposes of this application, imaging devices and imaging modalities can include but are not restricted to external and internal imaging devices as related to the living creature and can include but are not restricted to computer tomography (CT), magnetic resonance imaging (MRI), positron emission tomography (PET), Nuclear Medicine (NM), single photon emission computed tomography (SPECT) NM, ultrasound and ultrasound transducers, x-rays, fluoroscopy, endoscopes, and thermography.

For purposes of this disclosure, nuclear medicine is the application of radioactive substances to include but not restricted to the diagnosis and treatment of diseases. Radionuclides can be combined with but not restricted to other elements or compounds, or molecules to form radiopharmaceuticals, which can be used to image the body and its physiology. Nuclear Medicine can include the use of radioactive substances that can include but are not restricted to elements and compounds and molecules that can undergo transformation through processes to include but not restricted to radioactive decay and radioactive state changes and can include a nucleus of an unstable atom loses energy by emitting particles of ionizing radiation and is considered radioactive. Methods for imaging using radioactive materials include but are not restricted to Positron Emission Tomography (PET), standard nuclear medicine scintigraphy and single photon emission tomography (SPECT). In medical imaging these can be used alone combined with other imaging modalities to include but are not restricted to Computerized Tomography (CT), magnetic resonance imaging (MRI), routine x-rays, ultrasound and thermography. In some embodiments, a single isotope can be used but nuclear imaging and assessment can include but is not restricted to utilize and one or multiple isotopes. Isotopes can for measurement and imaging can include all radioactive isotopes and associated ligands or pharmaceutical compounds which in some embodiments include but are not restricted to Technecium 99m, Iodine 123, Iodine 131, Sestamibi Tc 99m, Flourodeoxyglucose (FDG), Flourine 18, Tc 99-HM-PAO (hexamethylpropylene amine oxime), thallium-201, xenon-133, indium 111, nitrogen-13, rubidium-82, krypton-81m, and C11-Cholineand Tc99 mMIBI and Tc99m pertechnetate. Dual isotope for parathyroid is most often I-123 or Tc99m pertectnetate and Sestamibi tc 99m but can be any combination of isotopes.

For purposes of this application, temporal variations include but are not restricted to changes in parameters within a given temporal frame that can include but are not restricted to changes in physical location or position, changes in radiation including but not restricted to decay and attenuation and increases and decreases in activity, and changes in dose administration and uptake and egress and ingress of radioactivity into and out of the field of view.

For purposes of this application, a non-visual imaging modality or imaging modality other than in the human-visible spectrum refer to imaging modalities capable of detecting wavelengths and frequencies that are outside the usual human visible wavelengths from about 390 to 700 nm, such as frequencies in the vicinity of 430-790 THz, ultraviolet, infrared, x-rays, gamma rays, and radioactive energy. Non-visual imaging modalities and imaging modalities other than in the human-visible spectrum may also refer to additional methods for identifying a structure or imaging a structure including but not restricted to other methods that utilize electromagnetic energy other than light in the human visible spectrum, thermography, kinetic energy, ultrasound, lasers, vibrational energy or radioactive energy. In some embodiments, non visual modalities may additionally or alternatively include the wavelengths within the usual human visible wavelengths features but the wavelengths being interrogated cannot be distinguished normally, readily or reproducibly by the human eye in a general population and require advanced spectral analysis or advanced visual technology for the wavelengths to be distinguished and separated.

LPS can be housed in a space that can be mobile or non-mobile and can include man-made and non-man-made structures and can include container structure that can include but is not restricted to a room, a container, a box, a helmet, an incubator, a surgical suite, a mobile unit to include but not restricted to an ambulance, a transportation vehicle, car, truck, helicopter, airplane, or water structure such as a boat.

The markers or locators of the LPS and GPS system can include but are not restricted to receive, or transmit and can both transmit and receive and can include but is not restricted to a transceiver, transponder, MIMO (multiple input, multiple output), service set identifier (SSID), SMS Spam (cell phone spam or short message service spam, infra-red ireless, radiofrequency e spam), MISO (multiple input, single output), lasers, ultrasound and other electromagnetic, and mechanical measuring and signaling units.

An object can lie within a body that can include but not restricted to lie beneath the skin, within an orifice to include but not restricted to the nostrils, the mouth, the orbit, the alimentary canal, the external auditory canal or the respiratory system and can be embedded, implanted, introduced, surgically inserted, pierced through or placed into an organ, a hollow viscous, the ectodermal, endodermal and mesodermal tissue and it derivatives.

Figure 12:
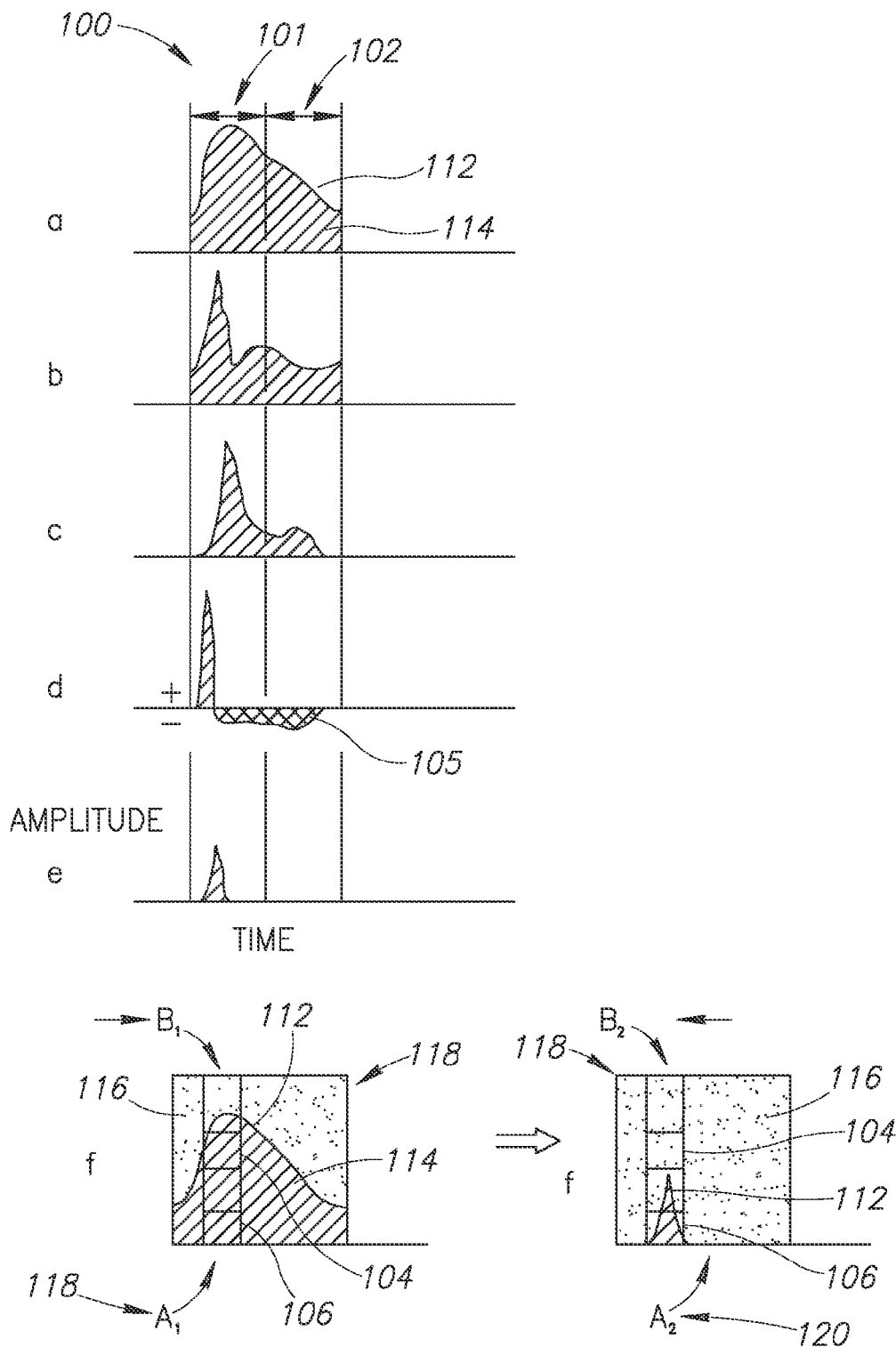
FIG. 12 is a depiction of a series of arterial waveform changes in or near a tissue bed which in this depiction is the corpora cavernosum of the penis.

FIG. 12 is a depiction of a series of arterial waveform changes in or near the tissue of the organ. In one embodiment the effectiveness of blood flow can be determined by calculating the area under the curve of the waveform. The wavelength can be separated into segments and the area under the curve for each of those segments can be calculated. The height of systolic and diastolic velocities and amplitudes can be measured and can include but is not restricted to the time needed to reach peak amplitudes and velocities, the time to reach one-half peak or other measurements of time to attain measurements to include but not restricted to flow measurements and velocity or amplitude or duration of the waveform or force or blood pressure or calculations to include but not restricted to resistivity index and peak systolic flow, peak diastolic flow, aberrations in the waveform, measurement to resistance to blood flow or pulsatility or pulsatility index or measurements of acceleration.

By combining these standard flow measurements with the segmental analysis of the waveform and the segmental and total area under the segments of the flow curve and the total waveform or one or more waveforms a signature can be developed for that waveform that can determine elements of the blood vessel and the tissue surrounding the blood vessel to include but not restricted to the flow in the vessel, the environment of the distal capillary system, the environment in which the blood vessel resides, the health and quality of the blood vessel, the elasticity of the blood vessel, the disease in the blood vessel, the health and disease if the tissue fed by and surrounding the blood vessel and the inflow and outflow of the blood vessel including but not restricted to elements such as the heart and feeding or supplying blood vessels and elements such as the distal blood vessels or the health or damage of the tissue and the pressure or resistance in the distal tissue. The segmental and the combined and total segment or averaged analysis of the individual segments of the waveform and the area calculations of the waveform and the shape of the waveform provide insights into blood flow and tissue and biological function that are not provided by the standard calculation of blood flow such as Resistivity index and Pulsatility index and Peak Systolic and Diastolic velocities that are the current standards of blood flow analysis.

In one embodiment penile blood flow can be measures within or adjacent to the corpora cavernosum of the penis. In a healthy blood vessel the segmental area under the systolic component of the curve and the segmental area of the diastolic component are robust during the early erectile phases and the systolic and diastolic areas under the waveform demonstrate that the blood vessel has large quantities of flow during both systole and diastole and indicate good inflow of blood and indicate that the capillary bed is still engorging and has mild or little resistance with an internal pressure in the sinusoids that is subdiastolic pressure or less than 60 to 90 mmHg Later in the erectile cycle the corpora cavernosum engorges and the sinusoids close and the pressure in the corpora cavernosum rises to diastolic levels. This results in the diminishment of inflow of blood during the diastolic phase and the area under the waveform diminishes and will approach zero inflow and this can be identified early by measuring the area under the diastolic component of the waveform.

As the pressure in the corpora cavernosum continues to increase the to supra-diastolic pressures, greater than 60 to 90 mmHg the systolic waveform begins to alter its shape and properties. The peak systolic velocity can even artificially elevate giving a false sense that there is increased blood flow but the area under the systolic curve diminishes indicating that in reality the inflow of blood during the systolic phase is actually diminishing not increasing as might be falsely surmised by the increasing systolic peak velocities. When the area under the diastolic curve is measured it also indicates diminished flow. When the corpora cavernosal pressure approaches or equals r even exceeds systolic pressures of between 100 to 140 mmHg the systolic waveform transforms and the area under the systolic curve diminishes. These same waveform area transformations can be seen in other blood vessel and tissue environments of the body to include but not restricted to the brain, kidney, heart, transplanted tissue, the skin, and other bodily organs or transplanted tissue or prostheses.

The waveform and waveform characteristics can be divided into segments such that the segments can include partial areas within a specific region of the waveform and these segments can be analyzed at a given point in time and a given temporal frame and then be analyzed in other points in time and other temporal sequences such that the change in spectral value or waveform or area under the curve or blood flow can be assessed and compared as a series or can be compared between one frame and another given frame and that information can be used to determine but not restricted to changes in blood flow and changes in the resistance around the vessel and in the distal outflow tissue and in the inflow sources. The absolute and the relative values of the quantitative and qualitative information derived from but not restricted to the waveform morphology, the waveform area and morphology changes can be analyzed over a point in time and a temporal sequence and the area outside or the waveform and within a given reference area or can include the inverse of the waveform or its area to yield additional blood flow and tissue characteristics.

These patterns can be applied to but not restricted to arterial flow, venous flow or capillary bed flow. These patterns can be used in the penis but are not restricted to the penis and can include tissue of the body that can include but are not restricted to the brain, the skin, to transplanted tissue, to skin flaps, to organs to include but not restricted to the heart or kidney, or liver. Signatures of these patterns of waveform characteristics of these changing patterns can be used to assess both general and specific blood vessel and non-blood vessel body tissue or a combination of these elements for health and diminished health or disease.

And can be used to determine tissue and blood vessel health and viability and morphology and disease states.

FIG. 12 depict arterial waveforms 112 with varying degrees of arterial inflow and increasing resistance within the vascular bed/environment.

In FIG. 12A the artery is at maximal inflow and the vascular bed is at minimal resistance. In this example the arterial systolic 100 pressure is 120 mmHg maximally, and diastolic 102 is 80 mmHg maximally and the vascular bed has a minimal pressure of less than 40 mmHg. The total area under the curve 112 in systole 100 and diastole 102 is greater than the waveform 112 area 114 throughout the remainder of the waveform 112 cycle of FIG. 12A through FIG. 12E. In FIG. 12B the arterial flow is subjected to an increase in the vascular capillary and vessel environment. The pressure in that environment approaches diastolic pressure 102 at 80 mmHg. In FIG. 12C the arterial flow is subjected to increasing environmental and capillary resistance and the pressure approaches supra-diastolic 102 and increasing systolic 100 pressure approaching 100 mmHg. In FIG. 12D the pressure in the capillary and vascular bed approach systolic pressure of 120 and reverse 105 flow is found in the diastolic 102 area. In FIG. 12E the pressure is supra-systolic 100 and the arterial systolic 100 flow continues to decrease and the diastolic 102 is zero or negative/reversed (not depicted). Over the course of the waveform's 112 evolution the area 110 under the waveform curves 112 diminishes in response to the approximation of inflow to the increase in distal arterial outflow within the receiving arterial or capillary bed. The midway point 101 between systole 100 and diastole 102 can be an arbitrary reference point 101.

In FIG. 12F the waveform 112 area can be calculated but the waveform 112 can be divided into regions 104,106 of the waveform 112 and waveform 112 area 114. The waveform 112 and the waveform 112 area 114 can be interrogated over time intervals including but not restricted to A1 118 and A2 120. The designated region 116 outside of the waveform curve 112 but within the designated 118 region or area 114, which can include but is not restricted to a rectangular region of interest 118. In this embodiment the region 118 is bordered by the initiation of systole 100 and the termination of diastole 102.

Enhanced detectability as used in this application includes but is not restricted to a marker or signal that is able to be differentiated or visible, or obvious or measurable or evident or demonstrable or noticeable from the environment in which the marker or signal is located. For a marker to have enhanced detectability or perceptibility in the existence of tissue or a body part or implant adjacent or in the vicinity of the marker, in some embodiments, it must include but is not restricted to a distinguishable and detectable difference relative to the adjacent or surrounding tissue in the vicinity of the marker in an intensity or precessional spin or relaxation time in MRI, an echo pattern or accoustical signature in Ultrasound, an activity level or particle or energy decay in Nuclear Medicine applications, thermal output or temperature in thermography, density in x-ray and CT, mechanical distance or movement in kinetic or mechanical measurements, frequency or amplitude in RF and wavelength in the visible or UV or Ultraviolet or electrical or other electromagnetic energy spectra or outputs. The detectability of a marker or locator is dependent on multiple factors including but not restricted to the sensitivity for the human or non-human receiver to detect differences each of these modalities inputs, the precision of the output signal that is sent to the observing unit or person and the composition of the environment in which the marker or locator is being distinguished or detected. Marker ranges are relative and can range from differences of less than 1% to greater than 100%. The optimal marker being dependent on the conspicuity between the environment and the marer is therefore also dependent on any artifacts generated around the marker or into the tissue being examined. In one embodiment a small difference of signals of 10 to 50% may be effective to reduce artifact whereas a larger difference may begin to generate artifacts as can be the case of acoustical differences in tissue in Ultrasound. Large differences of signal can generate artifacts in one modality but not another such a the difference between Air or Bone adjacent to brain tissue in some MRI sequences to include but not restricted to gradient echo or diffusion sequences whereas in CT, so long as the CT is properly calibrated, the difference between air and bone and brain tissue are detectable despite their density differences that can be great and even greater than 100% as measured in Hounsfield Units.

In some embodiments, the first material has a T-1 weighted sequence result having an intensity at least as great as fat of the living body and the second material has a T-2 weighted sequence result at least 25% as great as that of cerebrospinal fluid of the living body. In some embodiments, the second material has a T-2 weighted sequence result that is one of 10% as great, 25% as great, 50% as great, 75% as great, 90% as great, and 100 percent of that of cerebrospinal fluid of the living body. In another embodiment such as CT a difference can include but is not restricted to a difference of 10 to 50 or greater Hounsfield units can be sufficiently detected. In ultrasound the echo pattern or accoustical signature can be but is not restricted to only 10 to 50% more hyperechoic or hypoechoic relative to the tissue examined or adjacent and in one example air be utilized as a marker where if the air is in the form of a microbubble or nanodrop which can measure but is not restricted to 10 nm and 10 µm the air particle can be detected whereas if the air is free in an abscess and measures 2 mm it creates an artifact and distorts local tissue. In thermography the temperature differences can include but are not restricted to 1 or less than 1 degree. In nuclear medicine the activity can include differences in energy decay such as gamma of 1-131 of 364 KeV and 1-123 gamma decay of 159 KeV and Technecium or 140 KeV in energy level emitted and as relate to as low a 25 to 500 to 5000 microcuries as related to intensity of energy emitted and its relationship to the markers or locators background. In electromagnetic or wavelength and frequency and amplitude differences can be but are not restricted to differences of less than or greater than 1 to 10% of the portion of the electromagnetic spectrum being observed which can include but is not restricted to if frequency is measured in Hertz (Hz) can include 1 Hz. While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

In one embodiment there can be two mobile or non-fixed locators. The locators can have send and receive and both send and receive communication capacities. Communication in this invention can mean to send or transmit a signal, receive or accept a signal or can perform both functions and communication can mean to exchange information, a message, or provide access or send out or receive information or signals and can also include standard definitions of communication. In one embodiment one or more locaters referred to as the first locator can be affixed or be placed on or into the body and the second or more than one second locator can be used to locate or identify the first locator. In one embodiment, the first and second locators can be performed with or separate from the fixed locators that are used to find the location within the body. In another embodiment the first locator once placed can be considered or treated as a fixed locator and the second locator can be mobile and used to find or locate the first locator through various methods including but not restricted to visual mapping, imaging, sensory signals to include but not restricted to auditory, visual or kinetic touch or warmth or vibrational feedback or signals to inform the user of the second locator that they are moving closer or further from the first locator. In one preferred embodiment, the first locator can be inserted into a parathyroid gland using a percutaneous needle insertion method. The second locator can be affixed or integrated into but not restricted to a probe, surgical device, endoscope, fiber optic device, an imaging device, or needle such that as the first and second locator approach or diverge from each other the parameters can be determined as to distance and orientation from each other. In one embodiment the first locator that was inserted in the parathyroid can be measured as a distance 30 mm from the second locator, which was paced into the parathyroid under ultrasonic guidance and in this embodiment the surgeon can use a probe or scalpel which houses a second locator. As the probe or scalpel approached the parathyroid containing the first locator a 2-dimensional or 3-dimensional compass, altimeter, accelerometer or axis can inform the user that the probe or scalpel with the second locator is approaching or diverging from the first locator. Feedback signals or correction can be used to direct the surgeon to the parathyroid containing the first locator. This technique can be used for but not restricted to other body tissue and for implants, which can be biological or non-biological or organic or non-organic in nature. Locators or sensors can be or can include or incorporate devices to include compass, axis adjustment, accelerometer and altimeter.

EXEMPLARY EMBODIMENTS

1. A method for imaging comprising:
   receiving, by a computer system, a plurality of image frames, the plurality of image frames representing received nuclear radiation from a region of interest within a living body at a series of time points;
   receiving, by the computer system, for each frame of at least a portion of the plurality of image frames, a secondary measurement of the living body corresponding to the each frame; and
   generating, by the computer system, a plurality of adjusted frames based on the plurality of image frames by transforming at least a portion of the plurality of image frames according to the secondary measurements of the living body corresponding to the at least a portion of the plurality of image frames.

2. The method of claim 1, further comprising:
evaluating, by the computer system, temporal variation among the plurality of adjusted frames;
generating, by the computer system, an enhanced frame corresponding to an original frame of the plurality of image frames according to the evaluation of temporal variation of the plurality of adjusted frames, the enhanced frame having an enhanced representation of one or more target features relative to the one or more target features in the original frame; and
transmitting, by the computer system, the enhanced frame for display 3. The method of claim 2, wherein generating, by the computer system, the enhanced frame according to the evaluation of temporal variation among the plurality of adjusted frames further comprises:
adjusting in a first manner one or more first portions of the enhanced frame having a first temporal variation pattern in the plurality of adjusted frames; and
adjusting in a second manner one or more second portions of the enhanced frame having a second temporal variation pattern in the plurality of adjusted frames.

4. The method of claim 3, wherein the one or more first portions correspond to parathyroid glands of the living body and the one or more second portions correspond to a thyroid gland of the living body.

5. The method of claim 1, wherein transforming the at least a portion of the plurality of image frames according to the secondary measurements further comprises, for each frame of the at least a portion of the plurality of image frames:
identifying one or more first reference measurements from the secondary measurement corresponding to the each frame;
identifying one or more second reference measurements from the secondary measurement corresponding to a frame other than the each frame in the plurality of image frames; and
generating the adjusted frame of the plurality of adjusted frames corresponding to the each frame based on the first and second reference measurements.

6. The method of claim 1, wherein receiving, by the computer system, for the each frame of the at least a portion of the plurality of image frames, the secondary measurement of the living body corresponding to the each frame further comprises:
receiving one or more position measurements from one or more global positioning system receivers affixed to the living body.

7. The method of claim 1, wherein receiving, by the computer system, for the each frame of the at least a portion of the plurality of image frames, the secondary measurement of the living body corresponding to the each frame further comprises:
receiving one or more position measurements from one or more local positioning system receivers affixed to the living body.

8. The method of claim 1, wherein receiving, by the computer system, for the each frame of the at least a portion of the plurality of image frames, the secondary measurement of the living body corresponding to the each frame further comprises:
receiving an image from a camera having the living body in a field of view thereof.

9. The method of claim 1, wherein receiving, by the computer system, for the each frame of the at least a portion of the plurality of image frames, the secondary measurement of the living body corresponding to the each frame further comprises:
receiving a thermographic image from a thermographic camera having the living body in a field of view thereof.

10. The method of claim 1, wherein receiving, by the computer system, for the each frame of the at least a portion of the plurality of image frames, the secondary measurement of the living body corresponding to the each frame further comprises:
receiving measurements of translucence of the living body in a predetermined wavelength range.

11. The method of claim 1, wherein receiving, by the computer system, for the each frame of the at least a portion of the plurality of image frames, the secondary measurement of the living body corresponding to the each frame further comprises:
receiving measurements of the living body from a mechanical measuring means.

12. The method of claim 1, wherein receiving, by the computer system, for the each frame of the at least a portion of the plurality of image frames, the secondary measurement of the living body corresponding to the each frame further comprises:
receiving measurements of the living body from a magnetic resonance imaging system.

13. The method of claim 1, wherein receiving, by the computer system, for the each frame of the at least a portion of the plurality of image frames, the secondary measurement of the living body corresponding to the each frame further comprises receiving measurements of the living body from an ultrasound imaging system.

14. The method of claim 1, wherein receiving, by the computer system, for each frame of the at least a portion of the plurality of image frames, the secondary measurement of the living body corresponding to the each frame further comprises:
receiving measurements of the living body from at least one of an X-ray imaging system and a computed tomography imaging system.

15. The method of claim 1, wherein the received radiation from the region of interest is in response to administration of Tc99m-estamibi to the living body.

16. The method of claim 1, wherein the received radiation from the region of interest is in response to administration of a substance suitable for at least one of positron emission tomography and single-photon emission computed tomography.

17. A system for imaging comprising:
a radiation sensing system operable to detect radiation from a living body;
a secondary measurement system operable to detect a position of the living body; and
a computer system operably coupled to the radiation sensing system and the secondary measurement system, the computer system comprising one or more processors and one or more memory devices operably coupled to the one or more processors, the one or more memory devices storing executable and operational data effective to cause the one or more processors to receive a plurality of image frames from the radiation sensing system, receive, for each frame of at least a portion of the plurality of image frames, a secondary measurement of the living body corresponding to the each frame from the secondary measurement system, and generate a plurality of adjusted frames based on the plurality of image frames by transforming at least a portion of the plurality of image frames according to the secondary measurements of the living body corresponding to the at least a portion of the plurality of image frames.

18. The system of claim 17, wherein the executable and operational data are further effective to cause the one or more processors to:

evaluate temporal variation among the plurality of adjusted frames;

generate an enhanced frame corresponding to an original frame of the plurality of image frames according to the evaluation of temporal variation of the plurality of adjusted frames, the enhanced frame having an enhanced representation of one or more target features relative to the one or more target features in the original frame; and transmit the enhanced frame for display 19. The system of claim 18, wherein the executable and operational data are further effective to cause the one or more processors to generate the enhanced frame according to the evaluation of temporal variation among the plurality of adjusted frames by performing at least one of:

adjusting in a first manner one or more first portions of the enhanced frame having a first temporal variation pattern in the plurality of adjusted frames; and adjusting in a second manner one or more second portions of the enhanced frame having a second temporal variation pattern in the plurality of adjusted frames.

20. The system of claim 19, wherein the one or more first portions correspond to parathyroid glands of the living body and the one or more second portions correspond to a thyroid gland of the living body.

21. The system of claim 17, wherein the executable and operational data are further effective to cause the one or more processors to transform the at least a portion of the plurality of image frames according to the secondary measurements by, for each frame of the at least a portion of the plurality of image frames:

identifying one or more first reference measurements from the secondary measurement corresponding to the each frame;

identifying one or more second reference measurements from the secondary measurement corresponding to a frame in the plurality of image frames other than the each frame; and generating the adjusted frame of the plurality of adjusted frames corresponding to the each frame based on the first and second reference measurements.

22. The system of claim 17, wherein the secondary measurement system is one or more of global positioning system receivers coupled to the living body;

one or more local positioning system receivers affixed to the living body;

a thermographic camera having the living body in a field of view thereof;

a magnetic resonance imaging system;

an X-ray imaging system;

a computed tomography system;

a positron emission tomography system;

a single photon emission tomography system;

an ultrasound imaging system; and a mechanical measuring means.

23. A method for imaging comprising:

receiving, by a computer system, a plurality of image frames, the plurality of image frames representing received radiation from a region of interest within a living body at a series of time points;

evaluating, by the computer system, temporal variation among the plurality of image frames;

generating, by the computer system, an enhanced frame according to the evaluation of temporal variation by modifying an original frame of the plurality of image frames effective to enhance visibility of one or more target features of the one or more features in the enhanced frame; and transmitting, by the computer system, the enhanced frame for display 24. The method of claim 23, wherein modifying the original frame effective to enhance visibility of one or more target features further comprises:

adjusting in a first manner one or more first portions of the original frame having a first temporal variation pattern relative to a reference intensity; and adjusting in a second manner one or more second portions of the original frame having a second temporal variation pattern relative to the reference intensity.

25. The method of claim 24, wherein adjusting the one or more first portions in the first manner and adjusting the one or more second portions in the second manner comprises applying a temporal filter to the plurality of image frames.

26. The method of claim 25, wherein the temporal filter includes one or more of a linear filter, non-linear filter, Gaussian filter, and exponential curve filter.

27. The method of claim 24, wherein the one or more first portions correspond to parathyroid glands of the living body and the one or more second portions correspond to a thyroid gland of the living body.

28. The method of claim 23, wherein generating, by the computer system, the enhanced frame according to the evaluation of temporal variation further comprises:

modifying the original frame according to application of a mathematical model to the plurality of image frames.

29. The method of claim 23, wherein generating, by the computer system, the enhanced frame according to the evaluation of temporal variation further comprises:

modifying the original frame according to temporal variation of a reference feature in the plurality of image frames.

30. The method of claim 29, wherein the reference feature comprises a representation of radiation emitted by an artificial structure affixed to the living body.

31. The method of claim 30, wherein the artificial structure has a known decay rate and wherein modifying the original frame according to temporal variation of the reference feature of the one or more features further comprises:

correcting measured activity for one or more portions of the original frame according to measured activity for the artificial structure and the known decay rate.

32. The method of claim 23, further comprising identifying, by the computer system, a representation of a thyroid of the living body in the plurality of image frames by identifying in the plurality of image frames portions having an initial increase in activity relative to reference activity apparent in the plurality of image frames followed by a decrease in activity meeting a threshold condition with respect to the reference activity; and wherein generating, by the computer system, the enhanced frame according to the evaluation of temporal variation comprises altering the representation of the thyroid in the enhanced frame.

33. The method of claim 23, further comprising adjusting one or more of the plurality of image frames to compensate for movement of the living body across the series of time points.

34. The method of claim 33, wherein adjusting one or more adjusted frames of the plurality of image frames to compensate for movement of the living body across the series of time points further comprises:
identifying, by the computer system, a location of one or more features in the plurality of image frames; and
adjusting the one or more adjusted frames according to the identified locations of the one or more features in the plurality of image frames.

35. A method for imaging comprising:
administering a radioisotope to a living body;
receiving, by a computer system from a detector, a plurality of image frames, the plurality of image frames representing received radiation from a region of interest within the living body at a series of time points subsequent to administration of the radioisotope;
evaluating, by the computer system, temporal variation of the plurality of image frames;
generating, by the computer system, an enhanced frame according to the evaluation of the temporal variation effective to enhance conspicuity of one or more representations of one or more parathyroid glands of the living body in the enhanced frame; and
transmitting, by the computer system, the enhanced frame for display; and 36. The method of claim 35, wherein evaluating temporal variation of the plurality of image frames further comprises:
identifying, by the computer system, representations of a thyroid gland in the plurality of image frames according to temporal variation of the representations of the thyroid gland in the plurality of image frames; and
wherein generating the enhanced frame further comprises adjusting a representation of the thyroid gland in the enhanced frame effective to enhance the conspicuity of the one or more representations of the one or more parathyroid glands.

37. The method of claim 36, wherein identifying, by the computer system, the representations of the thyroid gland in the plurality of image frames according to the temporal variation of the representations of the thyroid gland in the plurality of image frames further comprises identifying in the plurality of image frames an initial increase in activity of the representations of the thyroid gland relative to reference activity apparent in the plurality of image frames followed by a decrease in activity meeting a threshold condition.

38. The method of claim 35, further comprising identifying the one or more representations of the one or more parathyroid glands in the plurality of image frames according to temporal variation of the one or more representations of the one or more parathyroid glands in the plurality of image frames.

39. The method of claim 38, wherein generating the enhanced frame further comprises adjusting the representations of the one or more parathyroid glands in the selected frame to enhance conspicuity of the representations of the one or more parathyroid glands.

40. The method of claim 38, wherein identifying the representation of the one or more parathyroid glands in the plurality of image frames according to the temporal variation of the representations of the one or more parathyroid glands in the plurality of image frames further comprises:
identifying the representations of the one or more parathyroid glands according to increasing activity of the representations one or more parathyroid glands relative to reference activity represented in the plurality of image frames.

41. The method of claim 35, further comprising adjusting one or more of the plurality of image frames to compensate for movement of the living body across the series of time points.

42. The method of claim 35, further comprising:
identifying, by the computer system, representations of one or more other organs exclusive of the thyroid gland of the living body; and
adjusting one or more of the plurality of image frames according to locations of the representations of the one or more other organs to compensate for movement of the living body across the series of time points.

43. The method of claim 35, wherein the radioisotope is the radioisotope is Tc99m-sestamibi.

44. The method of claim 35, further comprising:
identifying, by the computer system, the one or more representations of the one or more parathyroid glands in the enhanced frame;
identifying, by the computer system, a representation of the thyroid gland in the enhanced frame;
evaluating, by the computer system, one or more locations of the one or more representations of the one or more parathyroid glands relative to the representation of the thyroid in the enhanced frame; and
characterizing, by the computer system, health of the one or more parathyroid glands according to the evaluation of the locations of the one or more parathyroid gland.

45. The method of claim 44, wherein evaluating the one or more locations of the one or more representations of the one or more parathyroid glands further comprises evaluating at least one of:
asymmetry of the one or more locations of the one or more representations of the one or more parathyroid glands relative to the thyroid;
atypical positioning of the one or more locations of the one or more representations of the one or more parathyroid glands relative to the thyroid; and
eccentric positioning of the one or more locations of the one or more representations of the one or more parathyroid glands relative to the thyroid;

46. A method for imaging comprising:
administering a radioisotope to a living body;
receiving, by a computer system from a detector, an original frame, the original image representing received radiation from a region of interest within the living body subsequent to administration of the radioisotope;
administering a first treatment to the living body subsequent to administering the radioisotope, the first treatment effective to reduce activity in one or more parathyroid glands of the living body;
receiving, by the computer system from the detector, a confirmation frame, the confirmation frame representing received radiation from the region of interest within the living body subsequent to administering the first treatment;
comparing the confirmation frame to the original frame; and
identifying as one or more representations of the one or more parathyroid glands those portions of the original frame that have high apparent activity and for which corresponding portions in the confirmation frame have reduced apparent activity.

47. The method of claim 46, wherein the first treatment is at least one of non-radioactively labeled sestamibi, calcium, a calcium channel blocker, and an agent that alters the sensitivity of sensing receptors in the parathyroid.

48. A method for imaging comprising:
administering a first treatment to a living body, the first treatment operable to alter functioning of a first organ of the living body; and
generating an image of at least a portion of the living body including the first organ using a first imaging modality;
wherein the first treatment is effective to enhance conspicuity of a target portion of the living body due to the altering of the functioning of the first organ.

49. The method of claim 48, wherein the target portion is a second organ of the living body.

50. The method of claim 48, wherein the target portion is the first organ.

51. The method of claim 48, wherein the first organ is a parathyroid gland of the living body.

52. The method of claim 51, wherein the first treatment is effective to increase blood flow in the parathyroid gland.

53. The method of claim 51, wherein the first treatment is at least one of hydrochlorothiazide, calcium, calcium channel blocker, an inorganic phosphate, and an agent that alters the sensitivity of the sensing receptors in the parathyroid.

54. The method of claim 48, wherein the organ is a thyroid gland of the living body and the target portion is at least one parathyroid gland of the living body.

55. The method of claim 54, wherein the first treatment is effective to reduce blood flow to the thyroid gland.

56. The method of claim 55, wherein the first treatment is at least one of propylthiouracil, methimazole (Tapazole), thiourea, thiouracil, and a derivative of at least one of propylthiouracil, methimazole (Tapazole), thiourea, iodine, and thiouracil 57. The method of claim 48, further comprising administering a first substance to the living body, the first substance detectable according to the first imaging modality;
wherein the first treatment affects uptake by the first organ of the first substance.

58. The method of claim 57, wherein the first organ is a thyroid gland of the body, the first substance is Tc-99 Sestamibi, and first treatment is at least one of:
a thyroid agent including at least one of propylthiouracil, methimazole (Tapazole), thiourea, thiouracil, iodine, a thyroid 2 stimulating hormone (TSH), a thyroid 2 releasing hormone (TRH), a TSH blocking agent, a TRH blocking agent; and
and a derivative of the thyroid agent.

59. The method of claim 48, further comprising:
receiving, by a computer system, a plurality of first image frames, the plurality of first image frames representing received nuclear radiation from a region of interest within the living body at a series of time points;
receiving, by the computer system, for each frame of at least a portion of the plurality of image frames, a plurality of second image frames of the living body corresponding to the each frame, the second image frames obtained using the first imaging modality; and
generating, by the computer system, a plurality of adjusted frames based on the plurality of first image frames by transforming at least a portion of the plurality of first image frames according to the plurality of second image frames corresponding to the at least a portion of the plurality of first image frames.

60. The method of claim 59, further comprising:
evaluating, by the computer system, temporal variation among the plurality of adjusted frames;
generating, by the computer system, an enhanced frame corresponding to an original frame of the plurality of image frames according to the evaluation of temporal variation of the plurality of adjusted frames, the enhanced frame having an enhanced representation of one or more target features relative to the one or more target features in the original frame; and
transmitting, by the computer system, the enhanced frame for display 61. The method of claim 60, wherein generating, by the computer system, the enhanced frame according to the evaluation of temporal variation among the plurality of adjusted frames further comprises:
adjusting in a first manner one or more first portions of the enhanced frame having a first temporal activity pattern in the plurality of adjusted frames; and
attenuating in a second manner one or more second portions of the enhanced frame having a second temporal activity pattern in the plurality of adjusted frames.

62. The method of claim 48, wherein the first treatment is effective to affect calcium uptake by the first organ.

63. The method of claim 48, wherein the first treatment is one of adding and withdrawing energy from the organ.

64. A method for imaging comprising:
administering a first treatment to a living body, the first treatment operable to alter functioning of at least one of a thyroid gland and a parathyroid gland of the living body; and
generating an image of at least a portion of the living body including the parathyroid gland using a first imaging modality;
wherein the first substance is effective to enhance conspicuity of the parathyroid gland.

65. The method of claim 64, wherein the first treatment is effective to affect at least one of blood flow and uptake of a first substance by at least one of the thyroid gland and the parathyroid gland.

66. The method of claim 65, wherein the first substance is Tc-99 Sestamibi.

67. The method of claim 66, wherein the first treatment is effective to at least one of increase uptake of Tc-99 Sestamibi by the parathyroid gland and decrease uptake of Tc-99 Sestamibi by the thyroid gland.

68. A marker for imaging applications, the marker comprising:
a flexible structure conformable to a part of a living body, the flexible structure formed of a gelatinous elastomer; and
wherein the flexible structure further includes one or more materials effective to provide enhanced detectability in a plurality of imaging modalities in addition to the human visible spectrum.

69. The marker of claim 68, wherein at least one surface of the flexible structure at least one of is tackified and has an adhesive material secured thereto.

70. The marker of claim 68, wherein the flexible structure is secured to a rigid frame, the frame having at least one surface configured to conform to a portion of the living body.

71. The marker of claim 68, wherein the flexible structure is secured to a wearable item configured to fit over a portion of the living body.

72. The marker of claim 68, wherein the flexible structure secures to a portion of a hook-and-loop fastening system.

73. The marker of claim 68, wherein the one or more materials each have a signature in the plurality of imaging modalities that is distinguishable from tissue adjacent the flexible structure in the living body.

74. The marker of claim 68, wherein the plurality of imaging modalities include at least two of:
ultrasound;
x-rays;
computer tomography;
magnetic resonance imaging; and
nuclear medicine imaging.

75. The marker of claim 68, wherein at least one of the one or more materials is substantially homogeneously incorporated into the flexible structure.

76. The marker of claim 68, wherein the flexible structure defines a cavity and at least one of the one or more materials is positioned within the cavity.

77. The marker of claim 68, wherein the flexible structure defines a cavity and an electronic device is positioned within the cavity.

78. The marker of claim 77, wherein the electronic device comprises:
at least one sensor operable to detect at least one of an environmental factor and a biological process of the living body; and
a transmitter coupled to the sensor and operable to transmit a representation of at least one output of the at least one sensor.

79. The marker of claim 68, wherein the marker includes a radiation exposure sensor 80. The marker of claim 68, wherein the flexible structure has a non-natural perimeter shape.

81. The marker of claim 80, wherein the non-natural perimeter shape is at least one of a circle, triangle, square, and ellipse.

82. The marker of claim 68, wherein the flexible structure defines an annular shape having a void providing accessibility to skin of the living body to which the marker is secured.

83. The marker of claim 68, wherein the gelatinous elastomer is resiliently deformable.

84. The marker of claim 68, wherein the plurality of imaging modalities include at least two magnetic resonance imaging sequences selected from: T-1 spin echo, T-2 spin echo, gradient echo, turbo spin echo, spectroscopy and inversion recovery, fluid attenuated inversion recovery, and short T-1 inversion recovery.

85. A marker for imaging applications, the marker comprising:
a flexible structure conformable to a part of a living body;
a first material incorporated into the flexible structure, the first material being at least one of a hydrophilic and a water-like material at least one of a lipophilic material, lipid, oil, and fat-like material; and
a second material incorporated into the flexible structure, the second material being at least one of a hydrophilic and a water-like material.

86. The marker of claim 85, wherein the first and second materials are mixed together.

87. The marker of claim 86, wherein the first and second materials are homogeneously mixed.

88. The marker of claim 85, wherein the flexible structure includes a gelatinous elastomer.

89. The marker of claim 88, wherein the flexible structure is resiliently deformable.

90. The marker of claim 88, wherein the gelatinous elastomer incorporates the first material and second material in a block copolymer.

91. The marker of claim 85, wherein the first material has a T-1 weighted sequence result having an intensity at least as great as fat of the living body and the second material has a T-2 weighted sequence result at least 25% as great as that of cerebrospinal fluid of the living body.

92. The marker of claim 85, wherein the flexible structure has enhanced detectability in an imaging modality other than the human visible spectrum, the imaging modality including at least one of:
ultrasound;
x-rays;
computer tomography; and
nuclear medicine imaging.

93. The marker of claim 85, wherein the flexible structure has a non-natural perimeter shape.

94. The marker of claim 85, wherein the non-natural perimeter shape is at least one of a circle, triangle, square, and ellipse.

95. A method for diagnosing a condition comprising:
applying one or more markers to a living body, each of the one or more markers having a different marker signature in a first imaging modality;
generating an image of at least a portion of the living body including the one or more markers using the first imaging modality;
comparing a tissue signature of a representation of tissue in the living body in the image to the marker signatures of a representation of the one or more markers in the image; and
diagnosing a condition of the tissue according to the comparison.

96. The method of claim 95, wherein the steps of comparing and diagnosing are performed by a computer system.

97. The method of claim 95, wherein the one or more markers include a plurality of markers each having a different combination of T-1 weighted compounds and T-2 weighted compounds.

98. The method of claim 95, wherein diagnosing the condition of the tissue according to the comparison comprises determining at least one of bone marrow composition, extent of fatty liver condition, extent of fibrotic liver condition, extent of osteoporosis, presence of diabetes, degree of pancreatic fatty replacement, presence of adenomas, presence of tumors, presence of aggressive tumors, body fat calculations, and presence of metabolic replacement diseases.

99. The method of claim 95, wherein the one or more markers include a radiation exposure sensor.

100. A method for imaging comprising:
receiving, by a computer system, a plurality of image frames, the plurality of image frames representing received radiation from a region of interest within a living body at a series of time points;
identifying, by the computer system, representations of one or more organs and locations thereof in the plurality of image frames;
generating, by the computer system, a plurality of adjusted frames based on the image frames wherein one or more of the adjusted frames have been transformed relative to corresponding image frames of the plurality of image frames according to the locations of the representations of the one or more organs in the corresponding image frames.

101. The method of claim 100, further comprising:
    evaluating, by the computer system, temporal variation among the plurality of adjusted frames;
    generating, by the computer system, an enhanced frame corresponding to an original frame of the plurality of image frames according to the evaluation of temporal variation of the plurality of adjusted frames, the enhanced frame having an enhanced representation of one or more target features relative to the one or more target features in the original frame; and
    transmitting, by the computer system, the enhanced frame for display 102. The method of claim 101, wherein generating, by the computer system, the enhanced frame according to the evaluation of temporal variation among the plurality of adjusted frames further comprises:
    adjusting in a first manner one or more first portions of the enhanced frame having a first temporal variation pattern in the plurality of adjusted frames; and
    adjusting in a second manner one or more second portions of the enhanced frame having a second temporal variation pattern in the plurality of adjusted frames.

103. The method of claim 102, wherein the one or more first portions correspond to parathyroid glands of the living body and the one or more second portions correspond to a thyroid gland of the living body.

104. The method of claim 100, wherein generating, by the computer system, the plurality of adjusted frames based on the plurality of image frames further comprises:
    identifying expected three-dimensional locations of the one or more organs based on the plurality of image frames; and
    calculating two-dimensional locations for the one or more organs in the plurality of adjusted image frames based on the expected three-dimensional locations.

105. The method of claim 100, wherein, wherein generating, by the computer system, the plurality of adjusted frames based on the plurality of image frames further comprises, for each frame of at least a portion of the plurality of image frames:
    identifying first locations of the representations of the one or more organs in the each frame;
    identifying second locations of the representations of the one or more organs in a frame other than the each frame in the plurality of image frames; and
    generating the adjusted frame of the plurality of adjusted frames corresponding to the each frame according to a transformation based on the first locations and the second locations.

106. The method of claim 100, wherein the one or more organs perform uptake of a radioisotope.

107. The method of claim 100, wherein the one or more organs have a fixed location within the living body.

108. The method of claim 100, wherein the one or more organs include one or more of the salivary glands, nasal mucosa, heart, liver, and spleen of the living body.

109. The method of claim 100, wherein the received radiation from the region of interest is in response to administration of Tc99m-sestamibi to the living body.

110. A method for imaging comprising:
    administering a radioisotope to a living body;
    affixing one or more radioactive markers relative to the living body;
    receiving, by a computer system, a plurality of image frames, the plurality of image frames representing received radiation from the radioactive markers and from within the living body at a series of time points;
    identifying, by the computer system, one or more reference features and the locations thereof in the plurality of image frames, the one or more reference features corresponding to the radioactive markers;
    generating, by the computer system, a plurality of adjusted frames based on the image frames wherein one or more of the adjusted frames have been transformed relative to corresponding image frames of the plurality of image frames according to the locations of the one or more reference features in the corresponding image frames.

111. The method of claim 110, further comprising identifying, by the computer system, representations of one or more organs and locations thereof in the plurality of image frames;
    wherein generating the plurality of adjusted frames based on the image frames further comprises generating the plurality of adjusted frames by transforming corresponding image frames of the plurality of image frames based on both the locations of the reference features and the locations of the representations of the one or more organs in the corresponding image frames.

112. The method of claim 111, wherein the one or more organs include one or more of the salivary glands, nasal mucosa, heart, liver, and spleen of the living body.

113. The method of claim 110, wherein, wherein generating, by the computer system, the plurality of adjusted frames based on the plurality of image frames further comprises, for each frame of at least a portion of the plurality of image frames:
    identifying first locations of the representations of the one or more organs in the each frame;
    identifying second locations of the representations of the one or more organs in a frame other than the each frame in the plurality of image frames; and
    generating the adjusted frame of the plurality of adjusted frames corresponding to the each frame according to a transformation based on the first locations and the second locations.

114. The method of claim 110, further comprising:
    evaluating, by the computer system, temporal variation among the plurality of adjusted frames;
    generating, by the computer system, an enhanced frame corresponding to an original frame of the plurality of image frames according to the evaluation of temporal variation of the plurality of adjusted frames, the enhanced frame having an enhanced representation of one or more target features relative to the one or more target features in the original frame; and
    transmitting, by the computer system, the enhanced frame for display 115. The method of claim 114 wherein generating, by the computer system, the enhanced frame according to the evaluation of temporal variation among the plurality of adjusted frames further comprises:
    adjusting in a first manner one or more first portions of the enhanced frame having a first temporal variation pattern in the plurality of adjusted frames; and
    adjusting in a second manner one or more second portions of the enhanced frame having a second temporal variation pattern in the plurality of adjusted frames.

116. The method of claim 115, wherein the one or more first portions correspond to parathyroid glands of the living body and the one or more second portions correspond to a thyroid gland of the living body.

117. The method of claim 110, wherein affixing one or more radioactive markers relative to the living body comprises affixing the one or more radioactive markers to skin of the living body.

118. The method of claim 110, wherein affixing one or more radioactive markers relative to the living body comprises placing the radioactive markers internal to the living body.

119. The method of claim 109, wherein the radioisotope is Tc99m-sestamibi.

The embodiments of the invention in which an exclusive property or privilege is claimed are defined as follows:

1. A local positioning system (LPS) comprising:
a plurality of local position tracking devices with at least two of the local position tracking devices comprising components adapted to be distributed in different locations about a living body and at least one of the local position tracking devices comprising a further component adapted to be paired with the living body, each local position tracking device further comprising a transmitter and receiver with which to continually communicate in a message a time that the message was transmitted from the local position tracking device and a distance of the local position tracking device from each of the other local position tracking devices;
a master transmitter and receiver communicatively interfaceable to the local position tracking devices and configured to create a temporally-changing coordinate map and to continually revise the temporally-changing coordinate map using the positional coordinates of each local position tracking device within the temporally-changing coordinate map where the temporally-changing coordinate map is based on at least one of the times in the messages continually communicated from each of the local position tracking devices and from the local position tracking devices' distances in the messages continually communicated from each of the other local position tracking devices;
an imaging display configured to continually output the temporally-changing coordinate map prior to creation and registration of any image visualization of the living body; and
a barrier adapted to physically surround both the living body, the master transmitter and receiver and the plurality of local position tracking devices and defining an isolated space that is shielded from electromagnetic energy interference.

2. An LPS in accordance with claim 1, further comprising:
a biologically-safe physical marker comprised within the further component.

3. An LPS in accordance with claim 2, wherein a mechanism for the placement of the physical marker comprises one or more of adhesive, tapes, elastic, cloth, hook and loop fastener, a garment, a mask, a helmet, an apparatus designed to mold to a body part, membrane, injection into the skin, sutures in the skin, bands, straps, earrings, tattoos, and skin-piercings.

4. An LPS in accordance with claim 2, wherein at least two such further components are adapted to be positioned on structure of the living body.

5. An LPS in accordance with claim 4, further comprising:
a measurement component configured to monitor a position of the structure relative to the distances of the at least two such further components from each of the other local position tracking devices subsequent to the positioning on the structure of the at least two such further components based on the positional coordinates of the at least two such further components within the temporally-changing coordinate map.

6. An LPS in accordance with claim 1, further comprising:
a biologically-safe sensor comprised within the further component.

7. An LPS in accordance with claim 1, wherein the barrier comprises a faraday cage.

8. An LPS in accordance with claim 7, wherein the barrier comprises a helmet that conforms to a head of the living body.

9. An LPS in accordance with claim 7, wherein the barrier comprises a structure that is coextensive with a plurality of walls of a room.

10. An LPS in accordance with claim 1, further comprising:
the imaging display comprising the temporally-changing coordinate map as continually output by the master transmitter and receiver and an image visualization of the living body with the positional coordinates of the local position tracking devices superimposed.

11. An LPS in accordance with claim 10, further comprising:
a location marker superimposed on the image visualization based on the positional coordinates of the local position tracking devices.

12. An LPS in accordance with claim 10, further comprising:
a non-visual medical imaging modality that operates in a spectrum falling outside of wavelengths and frequencies visible to a naked human eye; and
the imaging display further comprising an enhanced image visualization of the living body as detected by the non-visual medical imaging modality.

13. An LPS in accordance with claim 12, wherein the non-visual medical imaging modality comprises one or more of magnetic resonance imaging, ultrasound, photo-acoustic imaging, X-ray, computed tomography, positron emission tomography, single-photon emission computed tomography, thermography, and nuclear medicine.

14. An LPS in accordance with claim 12, further comprising:
at least one further non-visual medical imaging modality that operates in a spectrum falling outside of wavelengths and frequencies visible to a naked human eye; and
the display further comprising the enhanced image visualization of the living body as detected by the at least one further non-visual medical imaging modality.

15. An LPS in accordance with claim 12, wherein the imaging display comprises an aligned image visualization of the image visualization of the temporally-changing coordinate map as continually output by the master transmitter and receiver and of the living body and the enhanced image visualization of the living body as detected by the non-visual medical imaging modality.

16. An LPS in accordance with claim 10, further comprising:
a visual medical imaging modality that operates in a spectrum falling within wavelengths and frequencies visible to a naked human eye; and
the imaging display further comprising an enhanced image visualization of the living body as detected by the visual medical imaging modality.

17. An LPS in accordance with claim 16, wherein the visual medical imaging modality comprises one or more of a miniature camera, eyepiece, microscope, magnifying device, fiber optic scope, and an endoscope.

18. An LPS in accordance with claim 16, wherein the imaging display comprises an aligned image visualization of the image visualization of the temporally-changing coordinate map as continually output by the master transmitter and receiver and of the living body and the enhanced image visualization of the living body as detected by the visual medical imaging modality.

19. An LPS in accordance with claim 10, wherein the image visualization comprises at least one of a two-dimensional map and a three-dimensional map.

20. An LPS in accordance with claim 1, further comprising:
a physiologic sensor suitable for placement into or onto the living body with which the further component is paired.

21. An LPS in accordance with claim 1, further comprising:
a robotic mechanism comprised with a medical implement with which the further component is comprised and operatively controllable based on the distance of the further component from each of the other local position tracking devices.

22. An LPS in accordance with claim 1, further comprising:
a prosthesis suitable for implant into or onto the living body with which the further component is paired.

23. An LPS in accordance with claim 22, the prosthesis further comprising:
at least one engagement point at which the prosthesis engages with the living body and around which one or more such further components are positioned.

24. An LPS in accordance with claim 23, further comprising:
a measurement component configured to monitor a position of the prosthesis relative to the at least one engagement point subsequent to embedding of the prosthesis in the living body based on the positional coordinates of the one or more such further components within the temporally-changing coordinate map.

25. An LPS in accordance with claim 1, wherein the barrier comprises structural elements selected from the group comprising conductive material, conductive mesh, subterranean enclosure, concrete encasement, electromagnetic shielding, electromagnetic energy shielding, radio frequency shielding, physical space containment or shielding, and mu-metal.

26. An LPS in accordance with claim 1, further comprising at least one of:
medical instrumentation within which the further component is comprised and adapted to be operable upon the living body; and
medical hardware within which the further component is comprised and adapted to be used within, upon, against, or around the living body.

27. An LPS in accordance with claim 1, further comprising a medical implement within which the further component is comprised that comprises one or more of a delivery device, locator, transmitter, receiver, sensing device, screws, nails, rods, plates, imaging modules or apparatuses, parts of or complete artificial joints, organs, muscles, ligaments, tendons and other body part replacements, native and non-native, xenograft and allograft and homograft, identical and non-identical donor material or body part, machines, sensors, flow devices, electromagnetic energy devices, kinetic energy devices, heat energy devices, ultrasound energy devices, mechanical energy devices, endoscopes, transducers, treatment apparatuses, surgical probes, scalpels, compass, altimeter, accelerometer, protractor, ruler, analog measuring device, analog measuring device, mechanical measuring device, ultrasound transducer, trocar, and a sponge.

* * * * *